United States Patent
Van Der Veen et al.

(10) Patent No.: US 8,288,379 B2
(45) Date of Patent: *Oct. 16, 2012

(54) THIA-TRIAZA-CYCLOPENTAZULENES

(75) Inventors: Lars Van Der Veen, Vienna (AT); Maria Impagnatiello, Vienna (AT); Darryl McConnell, Vienna (AT); Siegfried Schneider, Vienna (AT); Tobias Wunberg, Hinterbruehl (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 84 days.

This patent is subject to a terminal disclaimer.

(21) Appl. No.: 12/763,537

(22) Filed: Apr. 20, 2010

(65) Prior Publication Data

US 2011/0112087 A1     May 12, 2011

(30) Foreign Application Priority Data

Apr. 22, 2009    (EP) ..................................... 09158493

(51) Int. Cl.
*A61K 31/535* (2006.01)
*C07D 513/00* (2006.01)
(52) U.S. Cl. ...................... 514/232.8; 514/338; 548/151
(58) Field of Classification Search ............... 514/232.8, 514/338; 548/151
See application file for complete search history.

(56) References Cited

U.S. PATENT DOCUMENTS

2009/0156554 A1*   6/2009   Breitfelder et al. ............. 514/63

FOREIGN PATENT DOCUMENTS

| CA | 2579288 A1 | 4/2006 |
| WO | 2006040279 A1 | 4/2006 |
| WO | 2006040281 A1 | 4/2006 |
| WO | WO2006/040279 | * 4/2006 |

OTHER PUBLICATIONS

Breitfelder et al. CAS: 144:412499, 2006.*

* cited by examiner

*Primary Examiner* — Rei-tsang Shiao
(74) *Attorney, Agent, or Firm* — Michael P. Morris; Edward S. Lazer

(57) ABSTRACT

The present invention encompasses compounds of general formula (1)

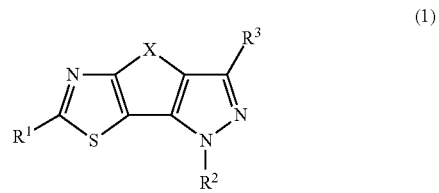

wherein
$R^1$ to $R^3$ and X are defined as in claim 1, which are suitable for the treatment of diseases characterized by excessive or abnormal cell proliferation, and the use thereof for preparing a medicament having the above-mentioned properties.

8 Claims, No Drawings

THIA-TRIAZA-CYCLOPENTAZULENES

The present invention relates to new thia-triaza-cyclopentazulenes of general formula (1)

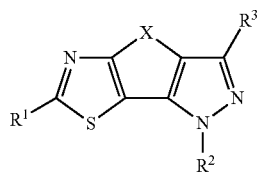
(1)

wherein the groups $R^1$ to $R^3$ and X have the meanings given in the claims and specification, the isomers thereof, processes for preparing these thia-triaza-cyclopentazulenes and their use as medicaments.

BACKGROUND OF THE INVENTION

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

Phosphatidylinositol-3-kinases (PI3-kinases) are a subfamily of the lipid kinases which catalyze the transfer of a phosphate group to the 3'-position of the inositol ring of phosphoinositides.

The phosphoinositide 3-kinase (PI3K) pathway is activated in a broad spectrum of human cancers. This may occur either via mutation of PI3K resulting in activation of the kinase, or indirectly via inactivation of the phosphatase and tensin homologue (PTEN) suppressor. In both cases, an activation of the signalling cascade is induced that promotes transformation of cells both in vitro and in vivo. Within the cascade, the Pi3K family of enzymes and the kinase mTOR play a pivotal role. The PI3K family comprises ca. 15 lipid kinases with distinct substrate specificities, expression pattern and modes of regulation. They play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories. The mammalian target of rapamycin (mTOR) is a serine/threonine kinase related to the lipid kinases of the PI3-kinase family. It exists in two complexes, mTORC1 and mTORC2, which are differentially regulated, have distinct substrate specificities, and are differentially sensitive to rapamycin. The central role of mTOR in controlling key cellular growth and survival pathways has sparked interest in discovering mTOR inhibitors that bind to the ATP site and therefore target both mTORC2 and mTORC1. As a consequence, inhibition of the PI3K pathway, particularly mediated via Pi3Kα and mTOR, has emerged as an attractive target for cancer therapeutics.

Thiazolyl-dihydro-indazoles are described for example as kinases inhibiting compounds in WO2006040279 and WO2006040281.

DETAILED DESCRIPTION OF THE INVENTION

It has now surprisingly been found that compounds of general formula (1), wherein the groups $R^1$ to $R^3$ and X have the meanings given below, act as inhibitors of specific kinases. Thus, the compounds according to the invention may be used for example for the treatment of diseases connected with the activity of specific kinases and characterised by excessive or abnormal cell proliferation.

The present invention relates to compounds of general formula (1)

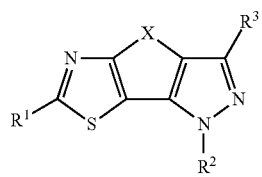
(1)

wherein
X is an optionally substituted C3 alkylidene chain wherein optionally one or two methylene units are independently from one another replaced by O, C(O), $NR^gC(O)$, S, SO, $SO_2$, $NR^gSO_2$, or $NR^g$; and wherein the substituents are independently from one another selected from $R^f$ and $R^g$; and
$R^1$ denotes hydrogen or $R^4$; and
$R^2$ denotes hydrogen or $R^5$; and
$R^3$ denotes hydrogen or $R^6$; and
each $R^4$, $R^5$ and $R^6$ independently of one another denotes a group selected from among $R^a$, $R^b$ and $R^a$ substituted by one or more identical or different $R^b$ and/or $R^c$; and
each $R^a$ independently of one another denotes a group optionally substituted by one or more identical or different $R^b$ and/or $R^c$, selected from among $C_{2-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each $R^b$ denotes a suitable group and is selected independently of one another from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^cOR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$, —$N(R^g)C(NR^g)NR^cR^c$, —N=$R^cR^c$ and —N=$C(R^g)NR^cR^c$ and
each $R^c$ independently of one another denotes hydrogen or a group optionally substituted by one or more identical or different R<sup>d</sup> and/or R<sup>e</sup>, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$-aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each R<sup>d</sup> denotes a suitable group and is selected independently of one another from among =O, —OR<sup>e</sup>, $C_{1-3}$haloalkyloxy, —OCF<sub>3</sub>, =S, —SR<sup>e</sup>, =NR<sup>e</sup>, =NOR<sup>e</sup>, =NNR<sup>e</sup>R<sup>e</sup>, =NN(R<sup>g</sup>)C(O)NR<sup>e</sup>R<sup>e</sup>, —NR<sup>e</sup>R<sup>e</sup>, —ONR<sup>e</sup>R<sup>e</sup>, —N(R<sup>g</sup>)NR<sup>e</sup>R<sup>e</sup>, halogen, —CF<sub>3</sub>, —CN, —NC, —OCN, —SCN, —NO, —NO<sub>2</sub>, =N<sub>2</sub>, —N<sub>3</sub>, —S(O)R<sup>e</sup>, —S(O)OR<sup>e</sup>, —S(O)<sub>2</sub>R<sup>e</sup>, —S(O)<sub>2</sub>OR<sup>e</sup>, —S(O)NR<sup>e</sup>R<sup>e</sup>, —S(O)<sub>2</sub>NR<sup>e</sup>R<sup>e</sup>, —OS(O)R<sup>e</sup>, —OS(O)<sub>2</sub>R<sup>e</sup>, —OS(O)<sub>2</sub>OR<sup>e</sup>, —OS(O)NR<sup>e</sup>R<sup>e</sup>, —OS(O)<sub>2</sub>NR<sup>e</sup>R<sup>e</sup>, —C(O)R<sup>e</sup>, —C(O)OR<sup>e</sup>, —C(O)SR<sup>e</sup>, —C(O)NR<sup>e</sup>R<sup>e</sup>, —C(O)N(R<sup>g</sup>)NR<sup>e</sup>R<sup>e</sup>, —C(O)N(R<sup>g</sup>)OR<sup>e</sup>, —C(NR<sup>g</sup>)NR<sup>e</sup>R<sup>e</sup>, —C(NOH)R<sup>e</sup>, —C(NOH)NR<sup>e</sup>R<sup>e</sup>, —OC(O)R<sup>e</sup>, —OC(O)OR<sup>e</sup>, —OC(O)SR<sup>e</sup>, —OC(O)NR<sup>e</sup>R<sup>e</sup>, —OC(NR<sup>g</sup>)NR<sup>e</sup>R<sup>e</sup>, —SC(O)R<sup>e</sup>, —SC(O)OR<sup>e</sup>, —SC(O)NR<sup>e</sup>R<sup>e</sup>, —SC(NR<sup>g</sup>)NR<sup>e</sup>R<sup>e</sup>, —N(R<sup>g</sup>)C(O)R<sup>e</sup>, —N[C(O)R<sup>e</sup>]<sub>2</sub>, —N(OR<sup>g</sup>)C(O)R<sup>e</sup>, —N(R<sup>g</sup>)C(NR<sup>g</sup>)R<sup>e</sup>, —N(R<sup>g</sup>)N(R<sup>g</sup>)C(O)R<sup>e</sup>, —N[C(O)R<sup>e</sup>]NR<sup>e</sup>R<sup>e</sup>, —N(R<sup>g</sup>)C(S)R<sup>e</sup>, —N(R<sup>g</sup>)S(O)R<sup>e</sup>, —N(R<sup>g</sup>)S(O)OR<sup>e</sup>—N(R<sup>g</sup>)S(O)<sub>2</sub>R<sup>e</sup>, —N[S(O)<sub>2</sub>R<sup>e</sup>]<sub>2</sub>, —N(R<sup>g</sup>)S(O)<sub>2</sub>OR<sup>e</sup>, —N(R<sup>g</sup>)S(O)<sub>2</sub>NR<sup>e</sup>R<sup>e</sup>, —N(R<sup>g</sup>)[S(O)<sub>2</sub>]<sub>2</sub>R<sup>e</sup>, —N(R<sup>g</sup>)C(O)OR<sup>e</sup>, —N(R<sup>g</sup>)C(O)SR<sup>e</sup>, —N(R<sup>g</sup>)C(O)NR<sup>e</sup>R<sup>e</sup>, —N(R<sup>g</sup>)C(O)NR<sup>e</sup>OR<sup>e</sup>, —N(R<sup>g</sup>)C(O)NR<sup>g</sup>NR<sup>e</sup>R<sup>e</sup>, —N(R<sup>g</sup>)N(R<sup>g</sup>)C(O)NR<sup>e</sup>R<sup>e</sup>, —N(R<sup>g</sup>)C(S)NR<sup>e</sup>R<sup>e</sup>, —[N(R<sup>g</sup>)C(O)]<sub>2</sub>R<sup>e</sup>, —N(R<sup>g</sup>)[C(O)]<sub>2</sub>R<sup>e</sup>, —N{[C(O)]<sub>2</sub>R<sup>e</sup>}<sub>2</sub>, —N(R<sup>g</sup>)[C(O)]<sub>2</sub>OR<sup>e</sup>, —N(R<sup>g</sup>)[C(O)]<sub>2</sub>NR<sup>e</sup>R<sup>e</sup>, —N{[C(O)]<sub>2</sub>OR<sup>e</sup>}<sub>2</sub>, —N{[C(O)]<sub>2</sub>NR<sup>e</sup>R<sup>e</sup>}<sub>2</sub>, —[N(R<sup>g</sup>)C(O)]<sub>2</sub>OR<sup>e</sup>, —N(R<sup>g</sup>)C(NR<sup>g</sup>)OR<sup>e</sup>, —N(R<sup>g</sup>)C(NOH)R<sup>e</sup>, —N(R<sup>g</sup>)C(NR<sup>g</sup>)SR<sup>e</sup>, —N(R<sup>g</sup>)C(NR<sup>g</sup>)NR<sup>e</sup>R<sup>e</sup>, —N=R<sup>e</sup>R<sup>e</sup> and —N=C(R<sup>g</sup>)NR<sup>e</sup>R<sup>e</sup> each R<sup>e</sup> independently of one another denotes hydrogen or a group optionally substituted by one or more identical or different R<sup>f</sup> and/or R<sup>a</sup>, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$-aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each R<sup>f</sup> denotes a suitable group and in each case is selected independently of one another from among =O, —OR<sup>g</sup>, $C_{1-3}$haloalkyloxy, —OCF<sub>3</sub>, =S, —SR<sup>g</sup>, =NR<sup>g</sup>, =NOR<sup>g</sup>, =NNR<sup>g</sup>R<sup>g</sup>, =NN(R<sup>h</sup>)C(O)NR<sup>g</sup>R<sup>g</sup>, —NR<sup>g</sup>R<sup>g</sup>, —ONR<sup>g</sup>R<sup>g</sup>, —N(R<sup>h</sup>)NR<sup>g</sup>R<sup>g</sup>, halogen, —CF<sub>3</sub>, —CN, —NC, —OCN, —SCN, —NO, —NO<sub>2</sub>, =N<sub>2</sub>, —N<sub>3</sub>, —S(O)R<sup>g</sup>, —S(O)OR<sup>g</sup>, —S(O)<sub>2</sub>R<sup>g</sup>, —S(O)<sub>2</sub>OR<sup>g</sup>, —S(O)NR<sup>g</sup>R<sup>g</sup>, —S(O)<sub>2</sub>NR<sup>g</sup>R<sup>g</sup>, —OS(O)R<sup>g</sup>, —OS(O)<sub>2</sub>R<sup>g</sup>, —OS(O)<sub>2</sub>OR<sup>g</sup>, —OS(O)NR<sup>g</sup>R<sup>g</sup>, —OS(O)<sub>2</sub>NR<sup>g</sup>R<sup>g</sup>, —C(O)R<sup>g</sup>, —C(O)OR<sup>g</sup>, —C(O)SR<sup>g</sup>, —C(O)NR<sup>g</sup>R<sup>g</sup>, —C(O)N(R<sup>h</sup>)NR<sup>g</sup>R<sup>g</sup>, —C(O)N(R<sup>h</sup>)OR<sup>g</sup>, —C(NR<sup>h</sup>)NR<sup>g</sup>R<sup>g</sup>, —C(NOH)R<sup>g</sup>, —C(NOH)NR<sup>g</sup>R<sup>g</sup>, —OC(O)R<sup>g</sup>, —OC(O)OR<sup>g</sup>, —OC(O)SR<sup>g</sup>, —OC(O)NR<sup>g</sup>R<sup>g</sup>, —OC(NR<sup>h</sup>)NR<sup>g</sup>R<sup>g</sup>, —SC(O)R<sup>g</sup>, —SC(O)OR<sup>g</sup>, —SC(O)NR<sup>g</sup>R<sup>g</sup>, —SC(NR<sup>h</sup>)NR<sup>g</sup>R<sup>g</sup>, —N(R<sup>h</sup>)C(O)R<sup>g</sup>, —N[C(O)R<sup>g</sup>]<sub>2</sub>, —N(OR<sup>h</sup>)C(O)R<sup>g</sup>, —N(R<sup>h</sup>)C(NR<sup>h</sup>)R<sup>g</sup>, —N(R<sup>h</sup>)N(R<sup>h</sup>)C(O)R<sup>g</sup>, —N[C(O)R<sup>g</sup>]NR<sup>g</sup>R<sup>g</sup>, —N(R<sup>h</sup>)C(S)R<sup>g</sup>, —N(R<sup>h</sup>)S(O)R<sup>g</sup>, —N(R<sup>h</sup>)S(O)OR<sup>g</sup>, —N(R<sup>h</sup>)S(O)<sub>2</sub>R<sup>g</sup>, —N[S(O)<sub>2</sub>R<sup>g</sup>]<sub>2</sub>, —N(R<sup>h</sup>)S(O)<sub>2</sub>OR<sup>g</sup>, —N(R<sup>h</sup>)S(O)<sub>2</sub>NR<sup>g</sup>R<sup>g</sup>, —N(R<sup>h</sup>)[S(O)<sub>2</sub>]<sub>2</sub>R<sup>g</sup>, —N(R<sup>h</sup>)C(O)OR<sup>g</sup>, —N(R<sup>h</sup>)C(O)SR<sup>g</sup>, —N(R<sup>h</sup>)C(O)NR<sup>g</sup>R<sup>g</sup>, —N(R<sup>h</sup>)C(O)NR<sup>g</sup>OR<sup>g</sup>, —N(R<sup>h</sup>)C(O)NR<sup>h</sup>NR<sup>g</sup>R<sup>g</sup>, —N(R<sup>h</sup>)N(R<sup>h</sup>)C(O)NR<sup>g</sup>R<sup>g</sup>, —N(R<sup>h</sup>)C(S)NR<sup>g</sup>R<sup>g</sup>, —[N(R<sup>h</sup>)C(O)]<sub>2</sub>R<sup>g</sup>, —N(R<sup>h</sup>)[C(O)]<sub>2</sub>R<sup>g</sup>, —N{[C(O)]<sub>2</sub>R<sup>g</sup>}<sub>2</sub>, —N(R<sup>h</sup>)[C(O)]<sub>2</sub>OR<sup>g</sup>, —N(R<sup>h</sup>)[C(O)]<sub>2</sub>NR<sup>g</sup>R<sup>g</sup>, —N{[C(O)]<sub>2</sub>OR<sup>g</sup>}<sub>2</sub>, —N{[C(O)]<sub>2</sub>NR<sup>g</sup>R<sup>g</sup>}<sub>2</sub>, —[N(R<sup>h</sup>)C(O)]<sub>2</sub>OR<sup>g</sup>, —N(R<sup>h</sup>)C(NR<sup>h</sup>)OR<sup>g</sup>, —N(R<sup>h</sup>)C(NOH)R<sup>g</sup>, —N(R<sup>h</sup>)C(NR<sup>h</sup>)SR<sup>g</sup>, —N(R<sup>h</sup>)C(NR<sup>h</sup>)NR<sup>g</sup>R<sup>g</sup>, —N=R<sup>g</sup>R<sup>h</sup> and —N=C(R<sup>h</sup>)NR<sup>h</sup>R<sup>h</sup>; and each R<sup>g</sup> independently of one another denotes hydrogen or a group optionally substituted by one or more identical or different R<sup>h</sup>, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero aryl, 6-18 membered heteroarylalkyl, 3-14 membered heterocycloalkyl and 4-14 membered heterocycloalkylalkyl; and each R<sup>h</sup> is selected independently of one another from among hydrogen, $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$-aryl, $C_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the prodrugs, the tautomers, the racemates, the enantiomers, the diastereomers, the prodrugs and the mixtures thereof, and optionally the pharmacologically acceptable salts thereof; with the proviso that N-[1-(4-methoxy-phenyl)-1,4,5,6-tetrahydro-9-thia-1,2,7-triaza-cyclopenta[e]azulen-8yl]-acetamide is not encompassed.

One aspect of the invention are compounds of general formula (1), wherein R<sup>3</sup> is a radical selected from the group consisting of imidazolyl, pyrazolyl, triazolyl, furyl, oxazolyl, pyridyl, pyrazinyl, pyrimidinyl and pyridazinyl, optionally substituted by one or more R<sup>6</sup>.

A further aspect of the invention are compounds of general formula (1), wherein R<sup>3</sup> is pyridyl, optionally substituted by one or more R<sup>6</sup>.

A further aspect of the invention are compounds of general formula (1), wherein R<sup>1</sup> is selected from among —NHR<sup>c</sup>, —NHC(O)R<sup>c</sup>, —NHC(O)OR<sup>c</sup>, —NHC(O)NR<sup>c</sup>R<sup>c</sup> and —NHC(O)N(R<sup>g</sup>)OR<sup>c</sup>.

A further aspect of the invention are compounds of general formula (1), wherein R<sup>2</sup> is selected from among $C_{1-6}$alkyl, $C_{1-6}$alkenyl, $C_{1-6}$alkynyl, $C_{3-10}$cycloalkyl, $C_{6-10}$aryl, 5-12 membered heteroaryl and 3-14 membered heterocycloalkyl, optionally substituted by one or more R<sup>5</sup>.

A further aspect of the invention are compounds of general formula (1), wherein X is an unsubstituted C3 alkylidene chain.

A further aspect of the invention are compounds of general formula (1A)

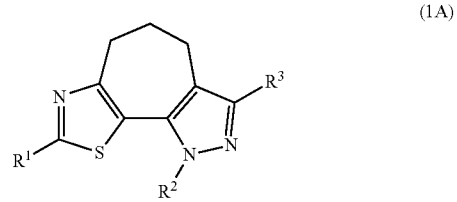

(1A)

wherein
R<sup>1</sup> denotes hydrogen or R<sup>4</sup> and
R<sup>2</sup> denotes hydrogen or R<sup>5</sup> and
R<sup>3</sup> denotes hydrogen or R<sup>6</sup>, and
each R<sup>4</sup>, R<sup>5</sup> and R<sup>6</sup> independently of one another denotes a group selected from among R<sup>a</sup>, R<sup>b</sup> and R<sup>a</sup> substituted by one or more identical or different R<sup>b</sup> and/or R<sup>c</sup>; and
each R<sup>a</sup> independently of one another denotes a group optionally substituted by one or more identical or different R<sup>b</sup> and/or R<sup>c</sup>, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is selected independently of one another from among =O, —OR$^c$, $C_{1-3}$haloalkyloxy, —OCF$_3$, =S, —SR$^c$, =NR$^c$, =NOR$^c$, =NN R$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O) R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N (R$^g$)OR$^c$, —C(NR$^g$)NR$^c$R$^c$, —C(NOH)R$^c$, —C(NOH) NR$^c$R$^c$, —OC(O)R$^c$, —OC(O)OR$^c$, —OC(O)SR$^c$, —OC(O) NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S) R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^c$OR$^c$, —N(R$^g$)C(O) NR$^g$NR$^c$R$^c$, —N(R$^g$)N(R$^g$)C(O)NR$^c$R$^c$, —N(R$^g$)C(S) NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$, —N(R$^g$)C(NR$^g$)NR$^c$R$^c$, —N=R$^c$R$^c$ and —N=C(R$^g$)NR$^c$R$^c$ and each $R^c$ independently of one another denotes hydrogen or a group optionally substituted by one or more identical or different R$^d$ and/or R$^e$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each $R^d$ denotes a suitable group and is selected independently of one another from among =O, —OR$^e$, $C_{1-3}$haloalkyloxy, —OCF$_3$, =S, —SR$^e$, =NR$^e$, =NOR$^e$, =NN R$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O) R$^e$, N[C(O)R$^e$]NR$^e$R$^e$, —N(R$^g$)C(S)R$^e$, —N(R$^g$)S(O)R$^e$, —N(R$^g$)S(O)OR$^e$—N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^e$OR$^e$, —N(R$^g$)C(O)NR$^g$ NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$, —N(R$^g$)C(NR$^g$)NR$^e$R$^e$, —N=R$^e$R$^e$ and —N=C(R$^g$)NR$^e$R$^e$ each $R^e$ independently of one another denotes hydrogen or a group optionally substituted by one or more identical or different R$^f$ and/or R$^a$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each $R^f$ denotes a suitable group and in each case is selected independently of one another from among =O, —OR$^g$, $C_{1-3}$haloalkyloxy, —OCF$_3$, =S, —SR$^g$, =NR$^g$, =NOR$^g$, =NNR$^g$R$^g$, =NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, =N$_2$, —N$_3$, —S(O)R$^g$, —S(O)OR$^g$, —S(O)$_2$R$^g$, —S(O)$_2$OR$^g$, —S(O)NR$^g$R$^g$, —S(O)$_2$NR$^g$R$^g$, —OS(O)R$^g$, —OS(O)$_2$R$^g$, —OS(O)$_2$OR$^g$, —OS(O)NR$^g$R$^g$, —OS(O)$_2$NR$^g$R$^g$, —C(O)R$^g$, —C(O)OR$^g$, —C(O)SR$^g$, —C(O)NR$^g$R$^g$, —C(O)N(R$^h$)NR$^g$R$^g$, —C(O)N(R$^h$)OR$^g$, —C(NR$^h$)NR$^g$R$^g$, —C(NOH)R$^g$, —C(NOH)NR$^g$R$^g$, —OC(O)R$^g$, —OC(O)OR$^g$, —OC(O)SR$^g$, —OC(O)NR$^g$R$^g$, —OC(NR$^h$)NR$^g$R$^g$, —SC(O)R$^g$, —SC(O)OR$^g$, —SC(O)NR$^g$R$^g$, —SC(NR$^h$)NR$^g$R$^g$, —N(R$^h$)C(O)R$^g$, —N[C(O)R$^g$]$_2$, —N(OR$^h$)C(O)R$^g$, —N(R$^h$)C(NR$^h$)R$^g$, —N(R$^h$)N(R$^h$)C(O) R$^g$, —N[C(O)R$^g$]NR$^g$R$^g$, —N(R$^h$)C(S)R$^g$, —N(R$^h$)S(O)R$^g$, —N(R$^h$)S(O)OR$^g$, —N(R$^h$)S(O)$_2$R$^g$, —N[S(O)$_2$R$^g$]$_2$, —N(R$^h$)S(O)$_2$OR$^g$, —N(R$^h$)S(O)$_2$NR$^g$R$^g$, —N(RNS(O)$_2$]$_2$R$^g$, —N(R$^h$)C(O)OR$^g$, —N(R$^h$)C(O)SR$^g$, —N(R$^h$)C(O)NR$^g$R$^g$, —N(R$^h$)C(O)NR$^g$OR$^g$, —N(R$^h$)C(O)NR$^h$ NR$^g$R$^g$, —N(R$^h$)N(R$^h$)C(O)NR$^g$R$^g$, —N(R$^h$)C(S)NR$^g$R$^g$, —[N(R$^h$)C(O)]$_2$R$^g$, —N(R$^h$)[C(O)]$_2$R$^g$, —N{[C(O)]$_2$R$^g$}$_2$, —N(R$^h$)[C(O)]$_2$OR$^g$, —N(R$^h$)[C(O)]$_2$NR$^g$R$^g$, —N{[C(O)]$_2$OR$^g$}$_2$, —N{[C(O)]$_2$NR$^g$R$^g$}$_2$, —[N(R$^h$)C(O)]$_2$OR$^g$, —N(R$^h$)C(NR$^h$)OR$^g$, —N(R$^h$)C(NOH)R$^g$, —N(R$^h$)C(NR$^h$)SR$^g$, —N(R$^h$)C(NR$^h$)NR$^g$R$^g$, —N=R$^h$R$^h$ and —N=C(R$^h$)NR$^h$R$^h$; and each $R^a$ independently of one another denotes hydrogen or a group optionally substituted by one or more identical or different R$^h$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero aryl, 6-18 membered heteroarylalkyl, 3-14 membered heterocycloalkyl and 4-14 membered heterocycloalkylalkyl; and each $R^h$ is selected independently of one another from among hydrogen, $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the prodrugs, the tautomers, the racemates, the enantiomers, the diastereomers, the prodrugs and the mixtures thereof, and optionally the pharmacologically acceptable salts thereof, with the proviso that N-[1-(4-methoxy-phenyl)-1,4,5,6-tetrahydro-9-thia-1,2,7-triaza-cyclopenta[e]azulen-8yl]-acetamide is not encompassed.

A further aspect of the invention are compounds of general formula (1A), wherein $R^3$ is a radical selected from the group consisting of imidazolyl, pyrazolyl, triazolyl, furyl, oxazolyl, pyridyl, pyrazinyl, pyrimidinyl and pyridazinyl, optionally substituted by one or more R$^6$.

A further aspect of the invention are compounds of general formula (1A), wherein $R^1$ is selected from among —NHR$^c$, —NHC(O)R$^c$, —NHC(O)OR$^c$, —NHC(O)NR$^c$R$^c$ and —NHC(O)N(R$^g$)OR$^c$.

A further aspect of the invention are compounds of general formula (1A), wherein $R^2$ is selected from among $C_{1-6}$alkyl, $C_{1-6}$alkenyl, $C_{1-6}$alkynyl, $C_{3-10}$cycloalkyl, $C_{6-10}$aryl, 5-12 membered Heteroaryl and 3-14 membered heterocycloalkyl, optionally substituted by one or more $R^5$.

A further aspect of the invention are compounds of general formula (1) or (1A), wherein $R^1$ is selected from the group consisting of: hydrogen, —$NH_2$,

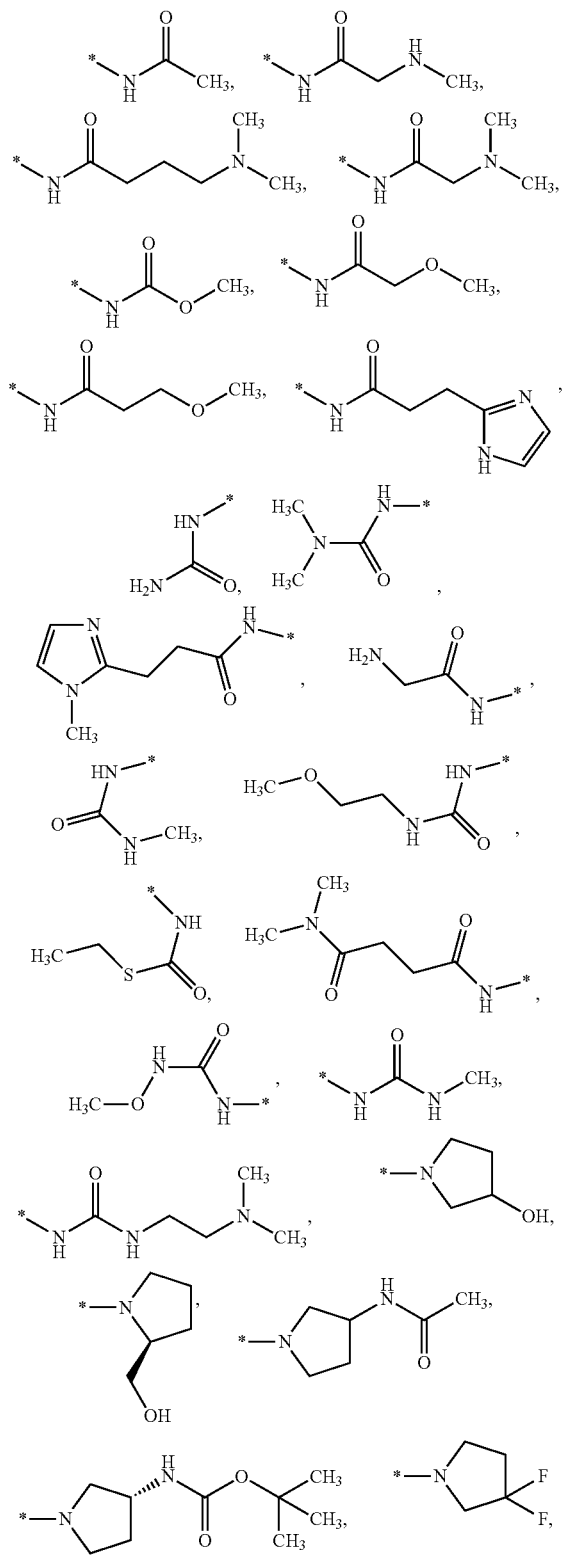

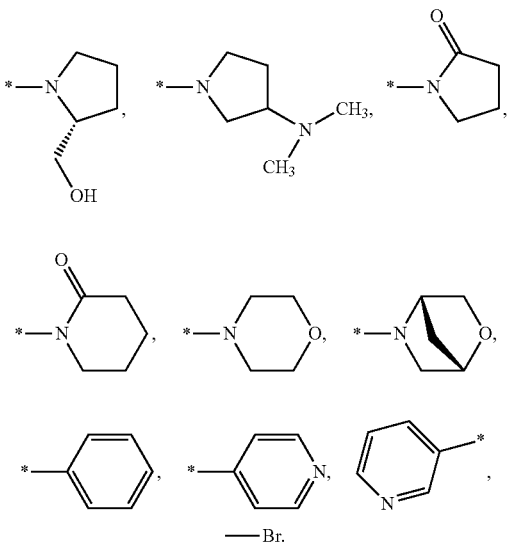

A further aspect of the invention are compounds of general formula (1) or (1A), wherein $R^2$ is selected from the group consisting of: —$CH_3$,

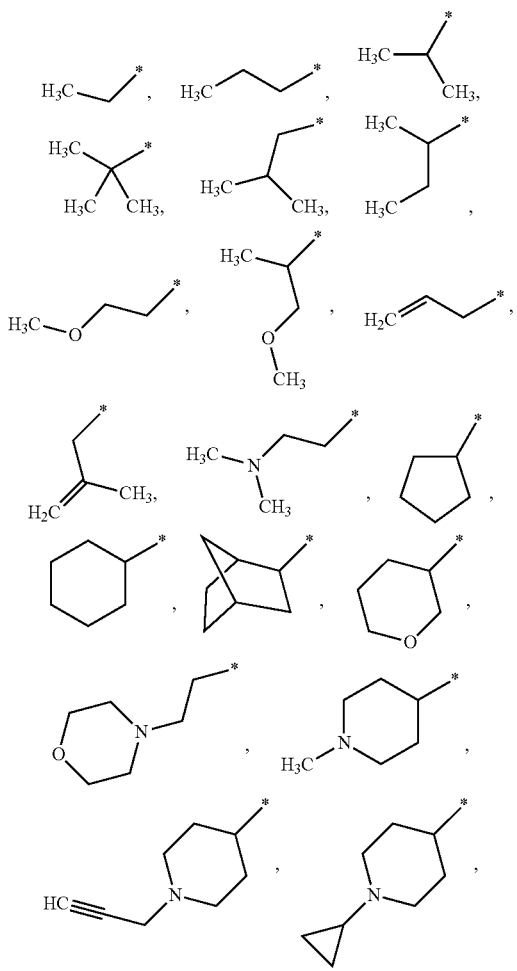

9
-continued

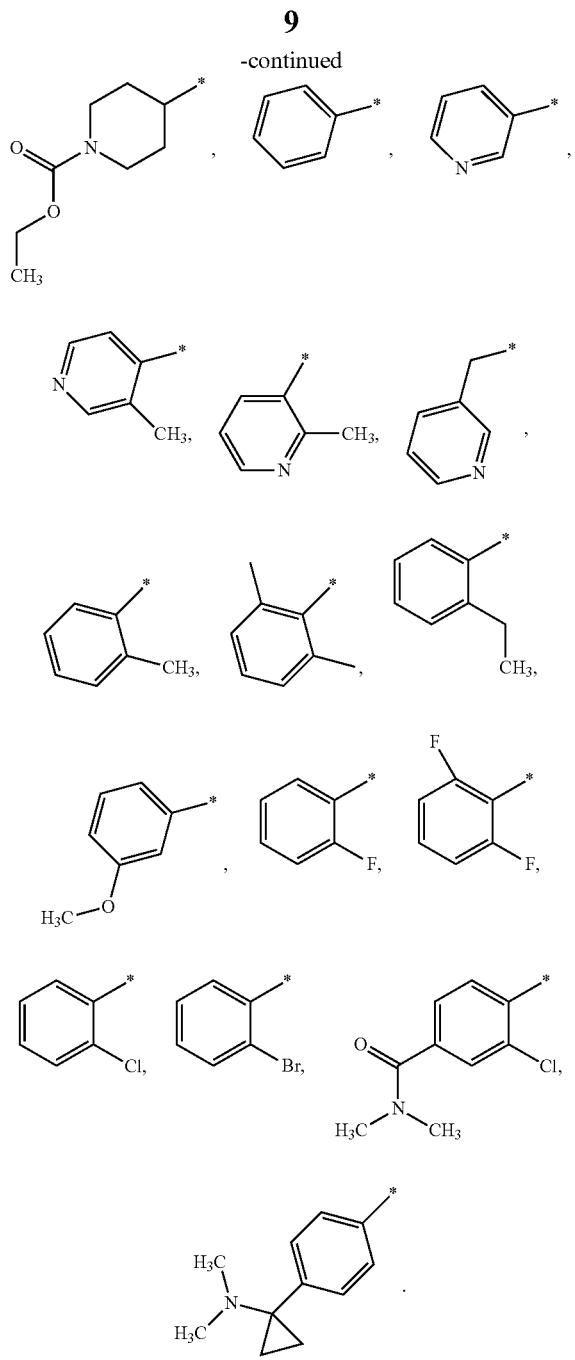

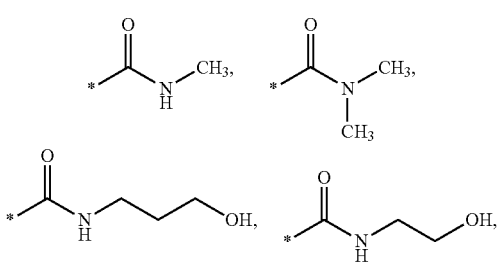

A further aspect of the invention are compounds of general formula (1) or (1A), wherein R³ is selected from the group consisting of: Hydrogen, —CH₃, —C(O)OH, 10
-continued

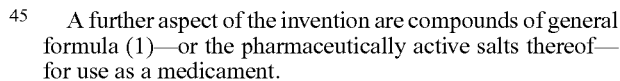

A further aspect of the invention are compounds of general formula (1)—or the pharmaceutically active salts thereof—for use as a medicament.

A further aspect of the invention are compounds of general formula (1)—or the pharmacologically effective salts thereof, for preparing a medicament with an antiproliferative activity.

A further aspect of the invention is a pharmaceutical preparation, containing as active substance one or more compounds of general formula (1) or the physiologically acceptable salts thereof optionally in conjunction with conventional excipients and/or carriers.

A further aspect of the invention is the use of a compound of general formula (1) for preparing a pharmaceutical composition for the treatment and/or prevention of cancer, infections, inflammatory and autoimmune diseases.

A further aspect of the invention is a pharmaceutical preparation comprising a compound of general formula (1) and at least one other cytostatic or cytotoxic active substance, different from formula (1), optionally in the form of the tautomers, the racemates, the enantiomers, the diastereomers and the mixtures thereof, and optionally the pharmacologically acceptable acid addition salts thereof.

The following Examples illustrate the present invention without restricting its scope.

Intermediates A

General Procedure A1: Formation of 1,3-Diketones from Acid Chlorides.

Under inert atmosphere the monoketone is added to dry THF and the reaction mixture is cooled to −78° C. LiHMDS (3 eq) is slowly added to the reaction mixture so that the reaction temperature is kept below −60° C. After completion of the addition, a solution of the acid chloride (1-2 eq) in dry THF is added slowly. The reaction mixture is stirred overnight allowing it to warm to RT. For the work-up the mixture is cooled to −20° C. and the reaction is quenched with diluted hydrochloric acid and phosphate buffer (consisting of 22 g NaH$_2$PO$_4$ and 87 g Na$_2$HPO$_4$ in 530 mL H$_2$O) resulting in a final pH of about 6. Ethyl acetate is added and the organic layer is separated. The aqueous phase is extracted with ethyl acetate, the combined organic phases are dried over MgSO$_4$, filtered and the solvent is removed under reduced pressure. The remaining solids are triturated with MTBE or EtOH. The product may be used without further purification.

General Procedure A2: Formation of 1,3-Diketones from Active Esters.

a) Formation of the Active Ester

Carboxylic acid is dissolved in DCM or DCE, CDI (1-3 eq) is added and the reaction mixture is stirred at RT overnight. The reaction mixture is washed ones with an aqueous 50% saturated NaCl solution, the organic phase is dried over MgSO$_4$ and concentrated under reduced pressure. The crude product is used without further purification.

b) Formation of the Diketone

A 1 M solution of LiHMDS (3 eq) in THF is diluted with THF and the resulting solution is cooled to −10° C. under inert atmosphere. The monoketone is added in small portions so that the reaction temperature is kept below −10° C. After stirring one additional hour at −10° C., a solution of the active ester (1-2 eq) in THF is added slowly. The reaction mixture is stirred overnight allowing it to warm to RT. The reaction is quenched with an aqueous saturated ammonium chloride solution and the aqueous phase is extracted twice with DCM. The combined organic layers are dried over MgSO$_4$, filtered and the solvent is removed under reduced pressure. The remaining solids are triturated with MTBE or EtOH. The product may be used without further purification.

General Procedure A3: Formation of Diketones from Esters

The monoketone (1.0 eq) is dissolved in DMSO or DMF and sodium tert-butoxide or sodium tert-pentoxide (3 eq) is added. The reaction mixture is stirred for 30 min at room temperature before the ester (1.1 eq) is added slowly. After completion of the addition of the ester the mixture is stirred for 4-16 h at RT, poured on ice and neutralized with saturated ammonium chloride solution or 1 M aqueous hydrochloric acid. The precipitate is filtered off, washed with water dried under vacuum at 40° C. overnight.

General Procedure A4: Nucleophilic Aromatic Substitution of O-Fluoropyridines

The o-fluoropyridine and an excess of the amine are dissolved in EtOH or iPrOH/THF (0.1-0.2 M) and the mixture is heated in the microwave at 100° C. for 30-60 min or alternatively the mixture is stirred at RT for 1-16 h. After completion of the reaction the solvent is removed under reduced pressure and the product is either purified by chromatography (NP with MeOH/DCM or RP with ACN/H$_2$O) or used as such.

A-01) 2-Amino-4,5,6,7-tetrahydro-cycloheptathiazol-8-one

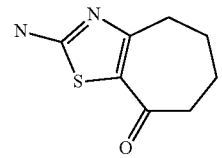

Cycloheptane-1,3-dione (20.0 g, 159 mmol) [prepared according to Organic Process Research & Development 1998, 2, 379] is taken up in 200 mL acetic acid and sodium acetate (14.3 g, 174 mmol) is added. The reaction mixture is stirred for 10 min, cooled to 10° C. and than bromine (8.99 mL, 174 mmol) is added dropwise over a period of 20 min. The reaction mixture is allowed to come to RT and stirred for 2 h. Thiourea (13.2 g, 174 mmol) is added and the reaction mixture is heated to 85° C. and stirred for 1 h. The reaction mixture is stirred overnight at RT, filtered and the solids are washed with 200 mL petroleum ether. The solids are taken up in water, filtered and the filtrate is basified to pH 8 with aqueous ammonia. The precipitated solids are filtered off and dried in vacuo. Yield: 10.0 g. HPLC-MS: $t_R$=0.14 min, (M+H)$^+$=183. $^1$H NMR (DMSO-d6): δ 7.81 (s, 2H), 2.84 (t, 2H), 2.58 (t, 2H), 1.81 (m, 4H).

A-02) N-(8-Oxo-5,6,7,8-tetrahydro-4H-cycloheptathiazol-2-yl)-acetamide

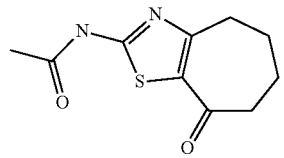

To a solution of A-01 (30.0 g, 165 mmol) in 150 mL acetic acid is added acetic anhydride (16.8 g, 165 mmol). The reaction mixture is heated to 116° C. and stirred for 1 h. The reaction mixture is cooled to RT, poured in 200 mL ice-water and stirred for 10 min. The precipitated solids are filtered off, washed with water and dried in vacuo. Yield: 36.9 g. HPLC-MS: $t_R$=1.09 min, (M+H)$^+$=225. $^1$H NMR (DMSO-d6): δ 3.02 (t, 2H), 2.71 (t, 2H), 2.16 (s, 3H), 1.91 (m, 2H), 1.84 (m, 2H).

A-03) (8-Oxo-5,6,7,8-tetrahydro-4H-cycloheptathiazol-2-yl)-carbamic acid methyl ester

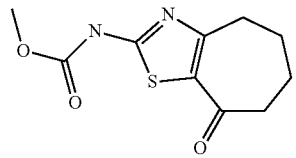

At 0° C. methyl chloroformate (3.60 mL, 46.6 mmol) and DIPEA (10.0 mL, 57.6 mmol) are added to a solution of A-01 (5.00 g, 27.4 mmol) in 40 mL dry THF. The cooling bath is removed and the reaction mixture is stirred overnight at 65°

C. The reaction mixture is cooled to RT, 1 M hydrochloric acid is added and the reaction mixture is extracted with DCM. The combined organic phases are washed with brine, dried over MgSO$_4$ and concentrated under reduced pressure. The residue is triturated with MeOH and dried in vacuo at 40° C. Yield: 4.34 g. HPLC-MS: $t_R$=1.89 min, (M+H)$^+$=241.

A-04) 1,1-Dimethyl-3-(8-oxo-5,6,7,8-tetrahydro-4H-cycloheptathiazol-2-yl)-urea

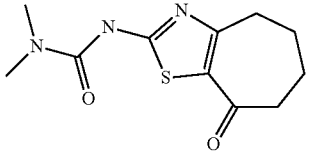

To a solution of A-01 (5.0 g, 27.4 mmol) in 300 mL acetonitrile are added CDI (8.90 g, 54.9 mmol) and DBU (8.21 mL, 54.9 mmol) and the reaction mixture is stirred overnight at 100° C. A solution of dimethylamine (69 mL, 2 M in THF) is added and the reaction mixture is stirred at 100° C. overnight. The reaction mixture is concentrated under reduced pressure, poured in 70 mL ice-water, acidified to pH 5 with 6 M hydrochloric acid and extracted with ethyl acetate. The combined organic phases are washed with brine, dried over MgSO$_4$ and concentrated under reduced pressure. Yield: 5.60 g. HPLC-MS: $t_R$=1.74 min, (M+H)$^+$=254.

A-05) 6-(tert-Butoxycarbonyl-ethyl-amino)-nicotinic acid

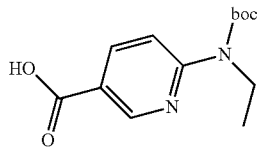

6-Chloro-nicotinic acid methyl ester (60 g, 0.35 mol) is taken up in 500 mL 2 Methyl-amine in THF and stirred at 100° C. in a sealed tube for 16 h. The reaction mixture is cooled to RT and the solvents are removed under reduced pressure. The residue is poured on ice and stirred for 15 min. The precipitate is filtered off, washed with water and dried in vacuo. The dried 6-ethylamino-nicotinic acid methyl ester (30 g, 0.17 mol) is dissolved in 150 mL DCM and triethylamine (29 mL, 0.20 mol), DMAP (4.0 g, 33 mmol) and di-tert-butyl dicarbonate (100 mL, 0.42 mol) are added successively at 0° C. The reaction mixture is allowed to warm up to RT and stirred for 16 h. To the reaction mixture 100 mL of 10% citric acid in water is added and the reaction mixture is stirred for 10 min. The organic phase is separated, dried over Na$_2$SO$_4$ and concentrated under reduced pressure.

Yield: 60 g.

The crude 6-(tert-butoxycarbonyl-ethyl-amino)-nicotinic acid methyl ester is taken up in 100 mL dioxane and a solution of lithium hydroxide monohydrate (13.5 g, 0.32 mol) in 100 mL water is added and the reaction mixture is stirred at RT for 4 h. The dioxane is removed from the reaction mixture under reduced pressure, additional water is added and the reaction mixture is acidified to pH 6 with a solution of 10% citric acid in water. The formed precipitate is filtered off and dried in vacuo. Yield: 36 g. $^1$H NMR (DMSO-d6): δ 13.2 (s, 1H), 8.8 (s, 1H), 8.2 (d, 1H), 7.8 (d, 1H), 4.0 (quart, 2H), 1.5 (s, 9H), 1.2 (t, 3H).

A-06) (5-Chlorocarbonyl-pyridin-2-yl)-ethyl-carbamic acid tert-butyl ester

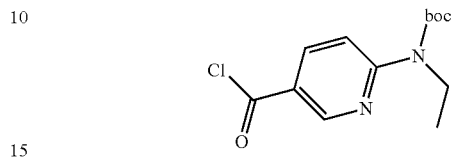

A-05 (6.40 g, 24.0 mmol) is taken up in 150 mL DCE, 1-chloro-N,N-2-trimethylpropenyl-amine (6.42 mL, 48.1 mmol) is added and the reaction mixture is stirred overnight at RT. The reaction mixture is concentrated under reduced pressure and the crude product is used in the next step without purification.

A-07) (5-Chlorocarbonyl-pyridin-2-yl)-methyl-carbamic acid tert-butyl ester

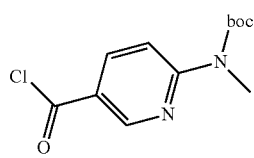

6-(tert-Butoxycarbonyl-methyl-amino)-nicotinic acid (12.5 g, 47.0 mmol) [prepared analogously to A-05 using methylamine in stead of ethylamine] is taken up in 300 mL DCE, 1-chloro-N,N-2-trimethylpropenyl-amine (10.0 mL, 74.8 mmol) is added and the reaction mixture is stirred overnight at RT. The reaction mixture is concentrated under reduced pressure and the crude product is used in the next step without purification.

A-08) 6-[N,N-Di-(tert-butoxycarbonyl)-amino]-nicotinic acid

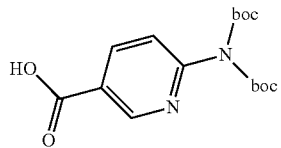

6-Amino-nicotinic acid methyl ester (13.7 g, 90.0 mmol), triethylamine (12.5 mL, 90.0 mmol) and DMAP (3.30 g, 27.0 mmol) are taken up in 200 mL DCM and a solution of di-tert-butyl dicarbonate (41.3 g, 189 mmol) in 40 mL DCM is added drop wise. The reaction mixture is stirred overnight at RT. An aqueous 5% KHSO$_4$ solution is added and the reaction mixture is extracted with DCM. The combined organic phases are washed with an aqueous 50% saturated KHCO$_3$ solution, dried over MgSO$_4$ and concentrated under reduced pressure. Yield: 34.9 g.

Of this residue 17.3 g is taken up in a mixture of 150 mL MeOH and 300 mL water, lithium hydroxide (2.33 g, 97.3 mmol) is added and the reaction mixture is stirred for 3 h at RT. The reaction mixture is acidified to pH 4 with acetic acid and the formed precipitate is filtered off, washed with water and dried in vacuo. Yield: 11.8 g. $^1$H NMR (DMSO-d6): δ 9.0 (s, 1H), 8.2 (d, 1H), 7.2 (d, 2H), 1.4 (s, 18H).

A-09) N-tert-Butoxycarbonyl-(5-chlorocarbonyl-pyridin-2-yl)-carbamic acid tert-butyl ester

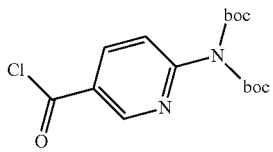

A-08 (5.00 g, 14.8 mmol) is dried by azeotropic distillation with toluene and then taken up in 20 mL dry THF and cooled to 0° C. 1-Chloro-N,N-2-trimethylpropenyl-amine (3.95 g, 30.0 mmol) is added drop wise and the reaction mixture is stirred at RT for 3 h. The reaction mixture is concentrated under reduced pressure and the crude product is used in the next step without purification.

A-10) [5-(2-Acetylamino-8-oxo-5,6,7,8-tetrahydro-4H-cycloheptathiazole-7-carbonyl)-pyridin-2-yl]-methyl-carbamic acid tert-butyl ester

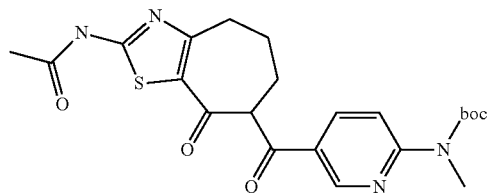

A-10 is prepared using general procedure A1 starting from A-02 (4.68 g, 20.9 mmol) and A-07 (9.04 g, 33.4 mmol). Yield: 4.63 g. HPLC-MS: tR=2.32 min, (M+H)$^+$=459, (M+H—C$_4$H$_8$)$^+$=403.

A-11) [5-(2-Acetylamino-8-oxo-5,6,7,8-tetrahydro-4H-cycloheptathiazole-7-carbonyl)-pyridin-2-yl]-ethyl-carbamic acid tert-butyl ester

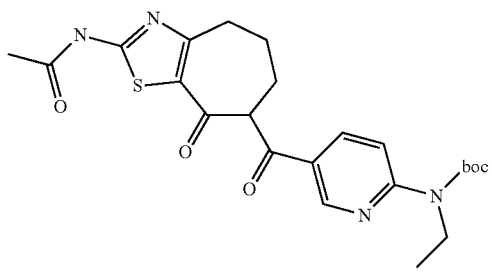

A-11 is prepared using general procedure A1 starting from A-02 (2.25 g, 10.0 mmol) and A-06 (4.27 g, 15.0 mmol). Yield: 3.13 g. HPLC-MS: tR=2.59 min, (M+H)$^+$=473, (M+H—C$_4$H$_8$)$^+$=417.

A-12) N-tert-Butoxy carbonyl-[5-(2-acetylamino-8-oxo-5,6,7,8-tetrahydro-4H-cycloheptathiazole-7-carbonyl)-pyridin-2-yl]-carbamic acid tert-butyl ester

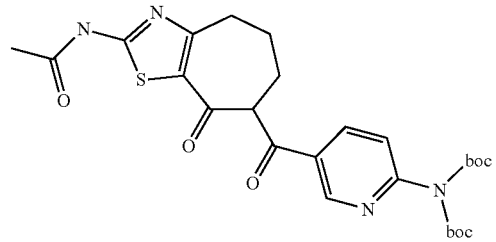

A-12 is prepared using general procedure A1 starting from A-02 (2.08 g, 9.28 mmol) and A-09 (5.30 g, 14.9 mmol). The product is purified by flash column chromatography (silica gel, 50-100% ethyl acetate in cyclohexane). Yield: 3.46 g. HPLC-MS: $t_R$=double peak 2.26/2.36 min, (M+H)$^+$=545, (M+H—CO$_2$—C$_4$H$_8$)$^+$=445, (M+H—CO$_2$-2*C$_4$H$_8$)$^+$=389, (M+H-2*CO$_2$-2*C$_4$H$_8$)$^+$=345.

A-13) (8-Oxo-5,6,7,8-tetrahydro-4H-cycloheptathiazol-2-yl)-thiocarbamic acid S-ethyl ester

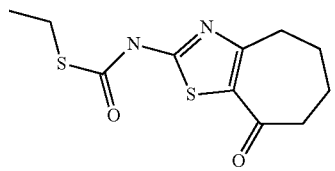

To a mixture of A-01 (5.00 g, 27.4 mmol) in 50 mL pyridine is added ethyl-chlorothioformate (4.17 mL, 387.4 mmol) and the reaction mixture is stirred for 1 h. at 50° C. The reaction mixture is concentrated under reduced pressure, taken up in DCM, washed with 1 M hydrochloric acid and saturated aqueous NaHCO$_3$ water, dried over MgSO$_4$ and concentrated under reduced pressure. The residue is triturated with diethylether. Yield: 5.03 g. HPLC-MS: $t_R$=2.46 min, (M+H)$^+$=271.

A-14) {5-[2-(3,3-Dimethyl-ureido)-8-oxo-5,6,7,8-tetrahydro-4H-cycloheptathiazole-7-carbonyl]-pyridin-2-yl}-methyl-carbamic acid tert-butyl ester

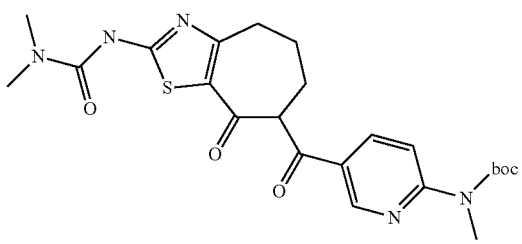

A-14 is prepared using general procedure A1 starting from A-04 (5.60 g, 22.1 mmol) and A-07 (9.58 g, 35.4 mmol). The product is purified by HPLC (C18, 10-98% acetonitrile in water containing 0.1% formic acid). Yield: 2.19 g. HPLC-MS: $t_R$=2.24 min, (M+H)$^+$=488, (M+H—CO$_2$—C$_4$H$_8$)$^+$=388.

A-15) {5-[2-(3,3-Dimethyl-ureido)-8-oxo-5,6,7,8-tetrahydro-4H-cycloheptathiazole-7-carbonyl]-pyridin-2-yl}-ethyl-carbamic acid tert-butyl ester

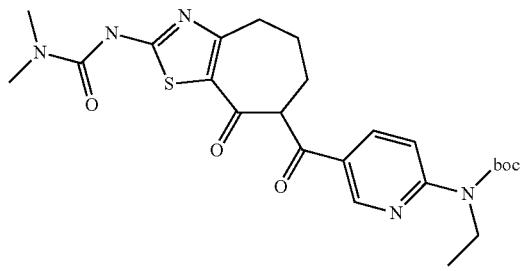

A-15 is prepared using general procedure A1 starting from A-04 (2.00 g, 7.90 mmol) and A-06 (3.60 g, 12.6 mmol). The product is purified by HPLC (C18, 2-98% acetonitrile in water containing 0.1% formic acid). Yield: 0.48 g. HPLC-MS: $t_R$=2.32 min, $(M+H)^+$=502, $(M+H-CO_2-C_4H_8)^+$=402.

A-16) N-tert-Butoxycarbonyl-{5-[2-(3,3-dimethyl-ureido)-8-oxo-5,6,7,8-tetrahydro-4H-cycloheptathiazole-7-carbonyl]-pyridin-2-yl}-ethyl-carbamic acid tert-butyl ester

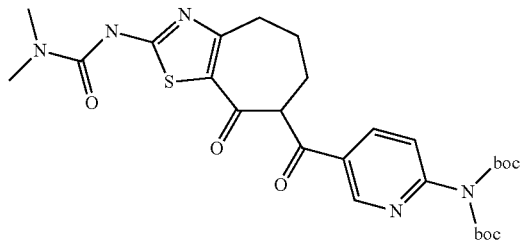

A-16 is prepared using general procedure A1 starting from A-04 (2.50 g, 9.87 mmol) and A-09 (5.63 g, 15.8 mmol). The product is purified by flash column chromatography (silica gel, 50-100% ethyl acetate in cyclohexane). Yield: 2.07 g. HPLC-MS: $t_R$=double peak 2.24/2.39 min, $(M-H)^-$=572.

A-17) {7-[6-(tert-Butoxycarbonyl-methyl-amino)-pyridine-3-carbonyl]-8-oxo-5,6,7,8-tetrahydro-4H-cycloheptathiazol-2-yl}-carbamic acid methyl ester

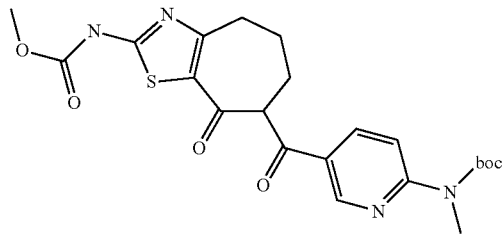

A-17 is prepared using general procedure A1 starting from A-03 (1.00 g, 4.16 mmol) and A-07 (1.80 g, 6.66 mmol). Yield: 1.70 g. HPLC-MS: tR=2.40 min, $(M+H)^+$=475, $(M+H-C_4H_8)^+$=419.

A-18) N-[7-(6-Methyl-pyridine-3-carbonyl)-8-oxo-5,6,7,8-tetrahydro-4H-cycloheptathiazol-2-yl]-acetamide

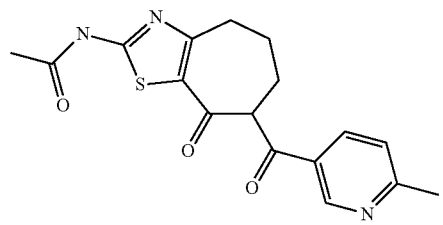

A-18 is prepared using general procedure A3 starting from A-02 (3.47 g, 15.3 mmol) and methyl 6-methylnicotinate (2.78 g, 18.4 mmol). The reaction is worked-up with DCM and the product is purified by flash column chromatography (silica gel, 33-66% ethylacetate in cyclohexane followed by 12% acetonitrile in ethyl acetate). Yield: 1.82 g. HPLC-MS: $t_R$=double peak 1.49/1.67 min, $(M+H)^+$=344.

A-19) [7-(6-Methyl-pyridine-3-carbonyl)-8-oxo-5,6,7,8-tetrahydro-4H-cycloheptathiazol-2-yl]-carbamic acid methyl ester

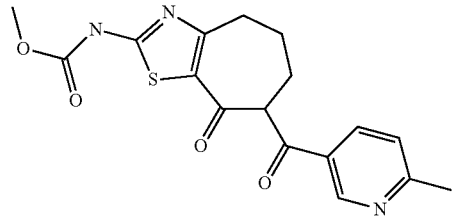

A-19 is prepared using general procedure A2 starting from A-03 (2.0 g, 8.32 mmol) and 6-methylnicotinic acid (5.0 g, 36.5 mmol). Yield: 2.37 g. HPLC-MS: $t_R$=1.90 min, $(M+H)^+$=360.

A-20) N-[7-(6-Fluoro-pyridine-3-carbonyl)-8-oxo-5,6,7,8-tetrahydro-4H-cycloheptathiazol-2-yl]-acetamide

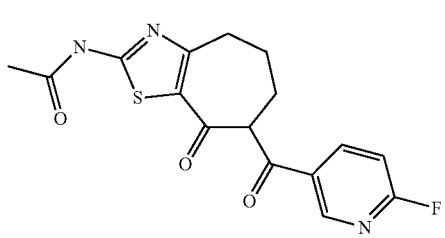

A-20 is prepared using general procedure A1 starting from A-02 (1.64 g, 7.31 mmol) and 6-fluoronicotinic acid chloride (1.56 g, 8.78 mmol). Yield: 1.98 g. HPLC-MS: $t_R$=1.20 min, $(M+H)^+$=348.

A-21) N-[7-(6-Methylamino-pyridine-3-carbonyl)-8-oxo-5,6,7,8-tetrahydro-4H-cycloheptathiazol-2-yl]-acetamide

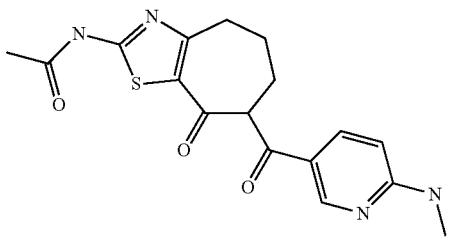

A-21 is prepared using general procedure A4 starting from A-20 (2.67 g, 7.69 mmol) and 41% methylamine in water (2.86 mL, 33.8 mmol). Yield: 1.29 g. HPLC-MS: $t_R$=double peak 1.32/1.65 min, $(M+H)^+$=359.

A-22) N-[7-(6-Ethylamino-pyridine-3-carbonyl)-8-oxo-5,6,7,8-tetrahydro-4H-cycloheptathiazol-2-yl]-acetamide

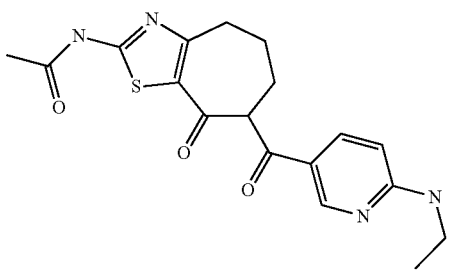

A-22 is prepared using general procedure A4 starting from A-20 (1.46 g, 4.20 mmol) and 2 Methylamine in MeOH (11.3 mL, 22.7 mmol). Yield: 0.56 g. HPLC-MS: $t_R$=double peak 1.49/1.82 min, $(M+H)^+$=373.

A-23) N-(7-Formyl-8-oxo-5,6,7,8-tetrahydro-4H-cycloheptathiazol-2-yl)-acetamide

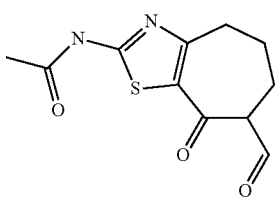

A-23 is prepared using general procedure A3 starting from A-02 (3.70 g, 16.5 mmol) and ethyl formate (3.90 mL, 47.4 mmol). Yield: 2.80 g. HPLC-MS: $t_R$=0.74 min, $(M+H)^+$=253.

A-24) (2-Acetylamino-8-oxo-5,6,7,8-tetrahydro-4H-cycloheptathiazol-7-yl)-oxo-acetic acid

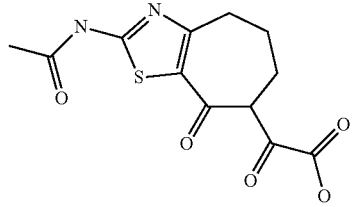

A-02 (8.50 g, 38.0 mmol) is slowly added to a suspension of sodium tert-pentoxide (12.5 g, 114 mmol) in a mixture of 50 mL DMF and 60 mL toluene and the reaction mixture is stirred for 10 min. Dimethyl oxalate (14.3 g, 120 mmol) is slowly added and after complete addition the reaction mixture is stirred at 40° C. for 10 min. The reaction mixture is acidified to pH 3 with 2 M hydrochloric acid, 50 mL water is added and the reaction mixture is stirred for 1 h. The reaction mixture is extracted with ethyl acetate and the combined organic phases are washed with water, dried over $MgSO_4$ and concentrated under reduced pressure. Yield: 9.00 g.

A-25) 2-Amino-7-(6-ethylamino-pyridine-3-carbonyl)-4,5,6,7-tetrahydro-cycloheptathiazol-8-one

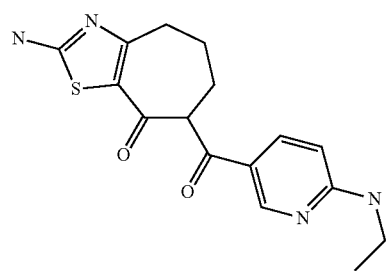

A-22 (2.0 g, 5.37 mmol) is taken up in 6.0 mL dioxane, 4.2 mL conc. hydrochloric acid are added and the reaction mixture is stirred at 95° C. for 2 h. The reaction mixture is concentrated under reduced pressure, taken up in 15 mL water and lyophilized Yield: 1.95 g. HPLC-MS: $t_R$=double peak 1.55/1.64 min, $(M+H)^+$=331.

A-26) 1-[7-(6-Ethylamino-pyridine-3-carbonyl)-8-oxo-5,6,7,8-tetrahydro-4H-cycloheptathiazol-2-yl]-3-methyl-urea

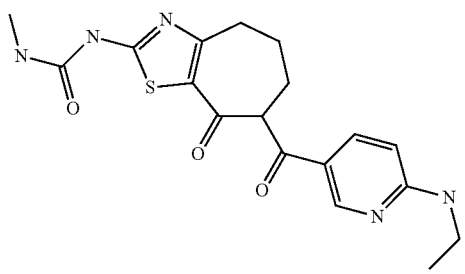

A-25 (0.30 g, 0.91 mmol) is taken up in 15 mL acetonitrile, DBU (0.27 mL, 1.8 mmol) and CDI (0.37 g, 2.3 mmol) are added and the reaction mixture is heated in a closed vial for 7 h at 100° C. The reaction mixture is cooled to RT, methylamine (4.5 mL, 2 M in THF) is added and the reaction mixture is heated overnight at 100° C. The reaction mixture is concentrated under reduced pressure and the product is purified by HPLC (C18, 20-80% acetonitrile in water containing 0.1% formic acid). Yield: 79 mg. HPLC-MS: $t_R$=double peak 1.69/1.78 min, $(M+H)^+$=388.

A-27) {[7-(6-Ethylamino-pyridine-3-carbonyl)-8-oxo-5,6,7,8-tetrahydro-4H-cycloheptathiazol-2-yl-carbamoyl]-methyl}-methyl-carbamic acid tert-butyl ester

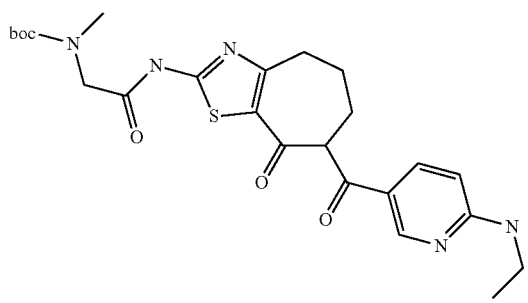

(tert-Butoxycarbonyl-methyl-amino)-acetic acid (0.43 g, 2.3 mmol) is taken up in 50 mL DCM, CDI (0.37 g, 2.3 mmol) is added and the reaction mixture is stirred overnight at RT. The reaction mixture is washed with 20 mL 50% saturated brine, dried over MgSO₄ and concentrated under reduced pressure. The residue is taken up in 2 mL acetonitrile and added to a mixture of A-25 (0.30 g, 0.91 mmol) and DBU (0.20 mL, 1.4 mmol) in 5 mL acetonitrile. The reaction mixture is stirred for 2 h at 100° C. The reaction mixture is concentrated under reduced pressure and the product is purified by flash chromatography (silica gel, 1-6% methanol in DCM). Yield: 0.33 g. HPLC-MS: $t_R$=double peak 1.94/1.97 min, $(M+H)^+$=502.

A-28) 4-Dimethylamino-N-[7-(6-ethylamino-pyridine-3-carbonyl)-8-oxo-5,6,7,8-tetrahydro-4H-cycloheptathiazol-2-yl]-butyramide

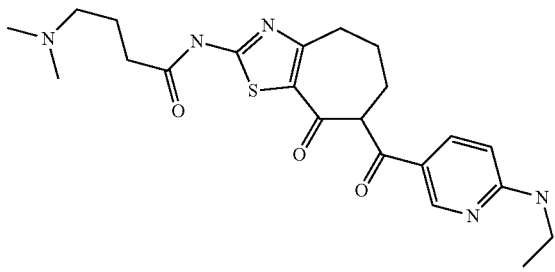

Example A-28 is prepared analogously to example A-27 starting from 4-dimethylbutyric acid hydrochloride (0.38 g, 2.3 mmol) and A-25 (0.30 g, 0.91 mmol). Yield: 0.75 g, content ca. 40%. HPLC-MS: $t_R$=double peak 1.48/1.60 min, $(M+H)^+$=444.

A-29) N-[7-(6-Ethylamino-pyridine-3-carbonyl)-8-oxo-5,6,7,8-tetrahydro-4H-cycloheptathiazol-2-yl]-3-methoxy-propionamide

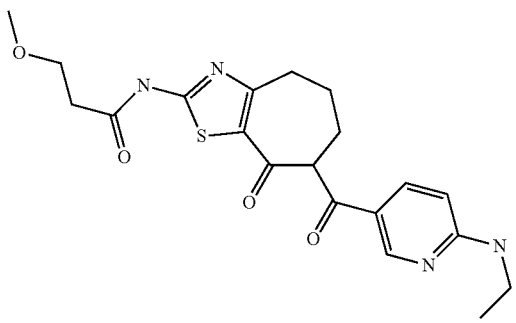

Example A-29 is prepared analogously to example A-27 starting from 3-methoxypropionic acid (0.21 mL, 2.3 mmol) and A-25 (0.30 g, 0.91 mmol). Yield: 0.43 g. HPLC-MS: $t_R$=double peak 1.76/1.82 min, $(M+H)^+$=417.

A-30) N-[7-(6-Ethylamino-pyridine-3-carbonyl)-8-oxo-5,6,7,8-tetrahydro-4H-cycloheptathiazol-2-yl]-3-(1-methyl-1H-imidazol-2-yl)-propionamide

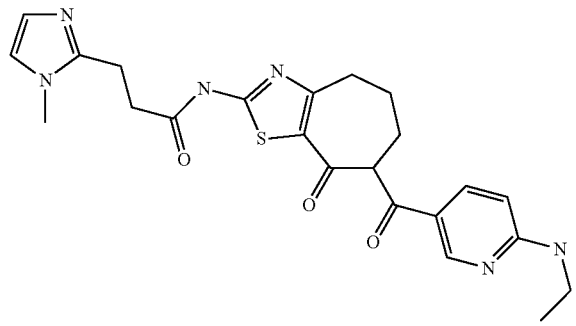

Example A-30 is prepared analogously to example A-27 starting from 3-(1-methyl-1H-imidazol-2-yl)propionic acid (0.35 g, 2.3 mmol) and A-25 (0.30 g, 0.91 mmol). Yield: 0.93 g, content ca. 40%. HPLC-MS: $t_R$=double peak 1.53/1.61 min, $(M+H)^+$=467.

A-31) N-[7-(6-Ethylamino-pyridine-3-carbonyl)-8-oxo-5,6,7,8-tetrahydro-4H-cycloheptathiazol-2-yl]-2-methoxy-acetamide

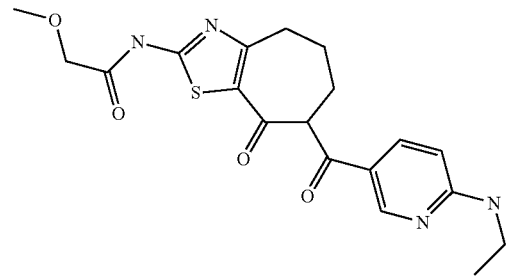

A-25 (0.40 g, 0.91 mmol) is taken up in 5 mL acetonitrile, DBU (0.27 mL, 1.8 mmol) is added and the reaction mixture is stirred for 10 min at RT. A solution of methoxyacetyl chloride (0.28 mL, 3.0 mmol) in 2 mL acetonitril is added and the reaction mixture is stirred for 2 h at 100° C. The reaction mixture is cooled to RT and concentrated under reduced pressure. The product is purified by flash chromatography (silicagel, 0-10% MeOH in DCM). Yield: 0.54 g. HPLC-MS: $t_R$=1.68 min, (M+H)$^+$=403.

A-32) {[7-(6-Ethylamino-pyridine-3-carbonyl)-8-oxo-5,6,7,8-tetrahydro-4H-cycloheptathiazol-2-yl-carbamoyl]-methyl}-carbamic acid tert-butyl ester

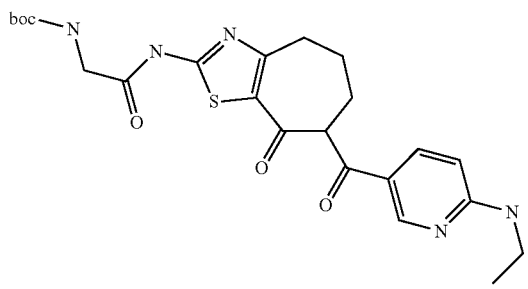

Example A-33 is prepared analogously to example A-27 starting from tert-butoxycarbonylamino-acetic acid (0.75 g, 4.3 mmol) and A-25 (0.40 g, 1.2 mmol). Yield: 0.29 g. HPLC-MS: $t_R$=double peak 1.81/1.85 min, (M+H)$^+$=488.

A-33) N-(7-{6-[(2,6-Dimethoxy-pyridin-3-ylmethyl)-amino]-pyridine-3-carbonyl}-8-oxo-5,6,7,8-tetrahydro-4H-cycloheptathiazol-2-yl)-acetamide

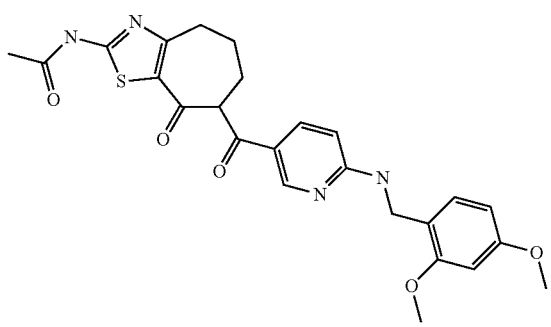

A-33 is prepared using general procedure A4 starting from A-20 (15 g, 43 mmol) and 2,4-dimethoxybenzylamine (16 mL, 108 mmol). Yield: 27 g. HPLC-MS: $t_R$=double peak 2.01/2.04 min, (M+H)$^+$=495, purity 60%.

A-34) 2-Amino-7-(6-amino-pyridine-3-carbonyl)-4,5,6,7-tetrahydro-cycloheptathiazol-8-one

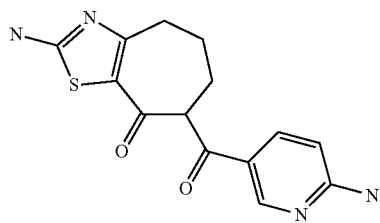

Example A-34 is prepared analogously to example A-25 starting from A-32 (17 g, 21 mmol). Yield: 14 g. HPLC-MS: $t_R$=0.73 min, (M+H)$^+$=303.

A-35) {[7-(6-Amino-pyridine-3-carbonyl)-8-oxo-5,6,7,8-tetrahydro-4H-cycloheptathiazol-2-ylcarbamoyl]-methyl}-carbamic acid tert-butyl ester

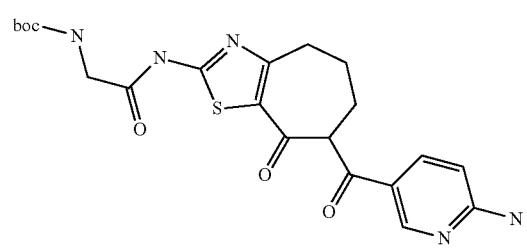

Example A-35 is prepared analogously to example A-27 starting from tert-butoxycarbonylamino-acetic acid (1.5 g, 8.6 mmol) and A-34 (2.3 g, 2.5 mmol). Yield: 0.87 g. HPLC-MS: $t_R$=double peak 1.80/1.84 min, (M+H)$^+$=460.

A-36) N-[7-(6-Amino-pyridine-3-carbonyl)-8-oxo-5,6,7,8-tetrahydro-4H-cycloheptathiazol-2-yl]-3-methoxy-propionamide

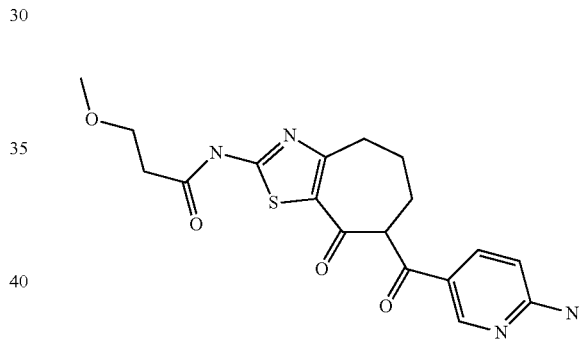

Example A-36 is prepared analogously to example A-27 starting from 3-methoxypropionic acid (0.81 mL, 8.6 mmol) and A-34 (2.3 g, 2.5 mmol). Yield: 0.35 g. HPLC-MS: $t_R$=double peak 1.66/1.73 min, (M+H)$^+$=389.

A-37) 2-Amino-7-(6-methylamino-pyridine-3-carbonyl)-4,5,6,7-tetrahydro-cycloheptathiazol-8-one

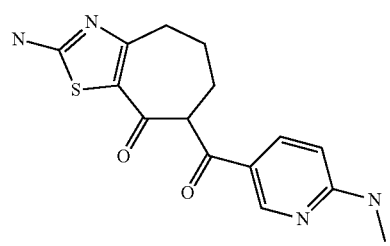

Example A-37 is prepared analogously to example A-25 starting from A-10 (5.8 g, 13 mmol). Yield: 5.3 g. HPLC-MS: $t_R$=0.53 min, (M+H)$^+$=317.

A-38) N-[7-(6-Methylamino-pyridine-3-carbonyl)-8-oxo-5,6,7,8-tetrahydro-4H-cycloheptathiazol-2-yl]-3-methoxy-propionamide

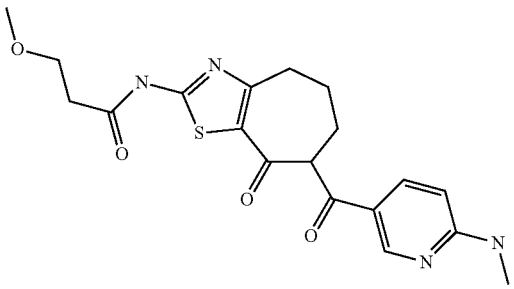

Example A-38 is prepared analogously to example A-27 starting from 3-methoxypropionic acid (0.19 mL, 2.0 mmol) and A-37 (0.50 g, 1.3 mmol). HPLC-MS: $t_R$=double peak 1.51/1.58 min, $(M+H)^+$=403.

A-39) N,N-Dimethyl-N'-[7-(6-methylamino-pyridine-3-carbonyl)-8-oxo-5,6,7,8-tetrahydro-4H-cycloheptathiazol-2-yl]-succinamide

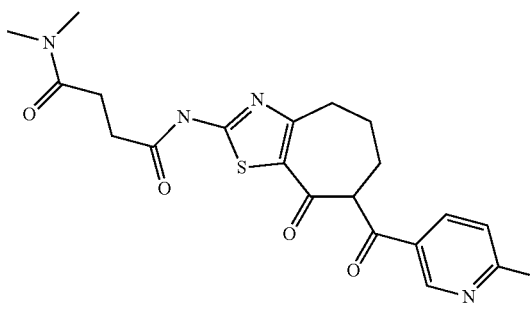

Example A-39 is prepared analogously to example A-27 starting from N,N-dimethyl-succinamic acid (0.39 g, 2.7 mmol) and A-37 (0.50 g, 1.3 mmol). Yield: 0.23 g. HPLC-MS: $t_R$=double peak 1.73/2.00 min, $(M+H)^+$=444.

A-40) 3-(1H-Imidazol-2-yl)-N-[7-(6-methylamino-pyridine-3-carbonyl)-8-oxo-5,6,7,8-tetrahydro-4H-cycloheptathiazol-2-yl]-propionamide

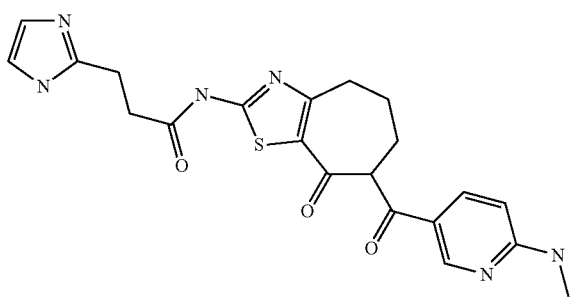

Example A-40 is prepared analogously to example A-27 starting from 3-(1H-Imidazol-2-yl)-propionic acid (0.51 g, 2.9 mmol) and A-37 (0.50 g, 1.3 mmol). Yield: 0.11 g. HPLC-MS: $t_R$=0.17 min, $(M+H)^+$=439.

A-41) 1-Trityl-1H-imidazole-4-carboxylic acid

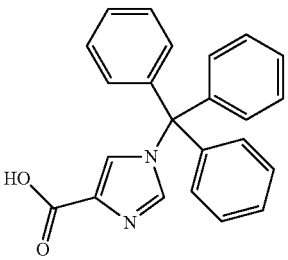

3H-Imidazole-4-carboxylic acid methyl ester (9.86 g, 78.2 mmol) is taken up in 150 mL DCM, triethylamine (11.9 mL, 86.0 mmol) is added and the reaction mixture is stirred for 5 min at RT. Chlorotriphenylmethane (24.0 g, 86.0 mmol) is added and the reaction mixture is stirred overnight at RT. The reaction mixture is extracted with an aqueous 5% $NaHCO_3$ solution, the organic phase is dried over $MgSO_4$ and concentrated under reduced pressure. The residue (20.7 g) is taken up in 100 mL MeOH, a solution of lithium hydroxide (4.80 g, 24.0 mmol) in 20 mL water is added drop wise and the reaction mixture is stirred over weekend at RT. The reaction mixture is acidified to pH 4 with 6N hydrochloric acid, 200 mL DCM is added and the two phase mixture is stirred vigorously. The phases are separated and the organic phase is dried over $MgSO_4$ and concentrated under reduced pressure. Yield: 19.2 g. HPLC-MS: double peak $t_R$=2.55/2.67 min, $(M-H)^-$=353.

A-42) 1-Trityl-1H-imidazole-4-carbonyl chloride

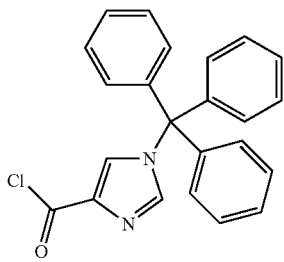

A-42 is prepared analogously to example A-09 starting from A-41 (15.9 g, 45.0 mmol) and 1-chloro-N,N-2-trimethylpropenyl-amine (10 mL, 75 mmol). The crude product is used in the next step without purification.

A-43) N-[8-Oxo-7-(1-trityl-1H-imidazole-4-carbonyl)-5,6,7,8-tetrahydro-4H-cycloheptathiazol-2-yl]-acetamide

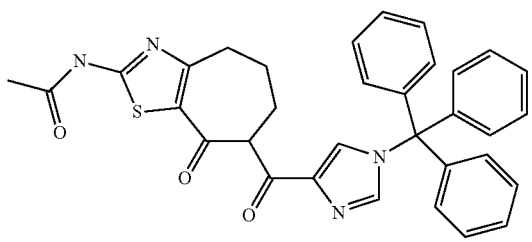

A-43 is prepared using general procedure A1 starting from A-02 (4.00 g, 17.8 mmol) and A-42 (16.6 g, 44.6 mmol). The crude product is used in the next step without purification. HPLC-MS: $t_R$=double peak 2.66/2.80 min, $(M-H)^-$=559.

A-44) 2-Methyl-1-(2-trimethylsilanyl-ethoxymethyl)-1H-imidazole-4-carboxylic acid

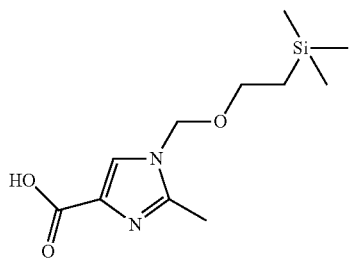

2-Methyl-1H-imidazole-4-carboxylic acid methyl ester (10.4 g, 74.1 mmol) is taken up in 100 mL DMF, sodium hydride (4.15 g, 60% in mineral oil, 104 mmol) is added portion wise and the reaction mixture is stirred at RT until all gas evolution has ceased. (2-Chloromethoxy-ethyl)-trimethyl-silane (14.4 mL, 81.6 mmol) is added and the reaction mixture is stirred at RT for 0.5 h. Water is added and the reaction mixture is extracted with ethylacetate, the combined organic phases are dried over $MgSO_4$ and concentrated under reduced pressure. The residue (20.0 g) is taken up in 20 mL dioxane and a solution of lithium hydroxide (3.54 g, 148 mmol) in 100 mL water is added slowly. The reaction mixture is stirred overnight at RT. The reaction mixture is cooled to 0° C., acidified to pH 4 by the addition of 6 N hydrochloric acid and extracted with DCM. The combined organic phases are dried over $MgSO_4$ and concentrated under reduced pressure. Yield: 7.01 g. HPLC-MS: $t_R$=2.16 min, $(M-H)^-$=257.

A-45) 2-Methyl-1-(2-trimethylsilanyl-ethoxymethyl)-1H-imidazole-4-carboyl chloride

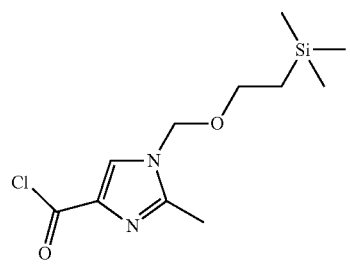

A-45 is prepared analogously to example A-09 starting from A-44 (7.3 g, 28 mmol) and 1-chloro-N,N-2-trimethylpropenyl-amine (6.8 mL, 51 mmol). The crude product is used in the next step without purification.

A-46) N-{7-[2-Methyl-1-(2-trimethylsilanyl-ethoxymethyl)-1H-imidazole-4-carbonyl]-8-oxo-5,6,7,8-tetrahydro-4H-cycloheptathiazol-2-yl}-acetamide

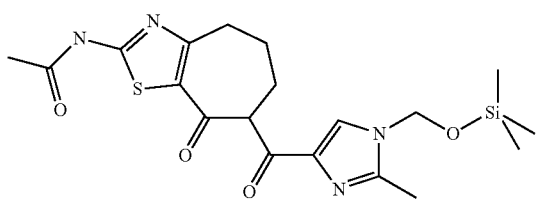

A-46 is prepared using general procedure A1 starting from A-02 (4.20 g, 18.7 mmol) and A-45 (7.72 g, 28.1 mmol). Yield: 1.5 g. HPLC-MS: $t_R$=2.01 min, $(M+H)^+$=463.

A-47) (5-Chlorocarbonyl-pyridin-2-yl)-(2,4-dimethoxy-benzyl)-carbamic acid tert-butyl ester

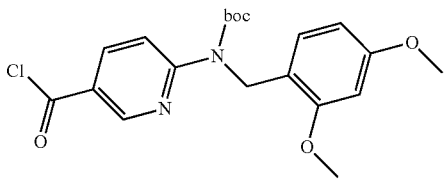

6-(tert-Butoxycarbonyl-(2,4-dimethoxy-benzyl)-amino)-nicotinic acid (23 g, 59 mmol) [prepared analogously to A-05 using 2,4-dimethoxybenzylamine in stead of ethylamine] is taken up in 400 mL dry THF, 1-chloro-N,N-2-trimethylpropenyl-amine (15 mL, 112 mmol) is added and the reaction mixture is stirred at RT for 0.5 h. The reaction mixture is concentrated under reduced pressure and the crude product is used in the next step without purification.

A-48) [5-(2-Acetylamino-8-oxo-5,6,7,8-tetrahydro-4H-cycloheptathiazole-7-carbonyl)-pyridin-2-yl]-(2,4-dimethoxy-benzyl)-carbamic acid tert-butyl ester

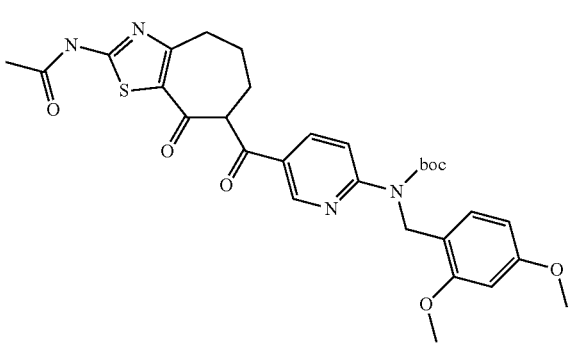

A-48 is prepared using general procedure A1 starting from A-02 (10 g, 45 mmol) and A-47 (27 g, 67 mmol). The crude product is used in the next step without purification. HPLC-MS: $t_R$=double peak 2.31/2.42 min, $(M+H)^+$=595.

A-49) [5-(2-Acetylamino-8-hydroxy-5,6-dihydro-4H-cycloheptathiazole-7-carbonyl)-pyridin-2-yl]-(2,4-dimethoxy-benzyl)-carbamic acid tert-butyl ester trifluoroborate

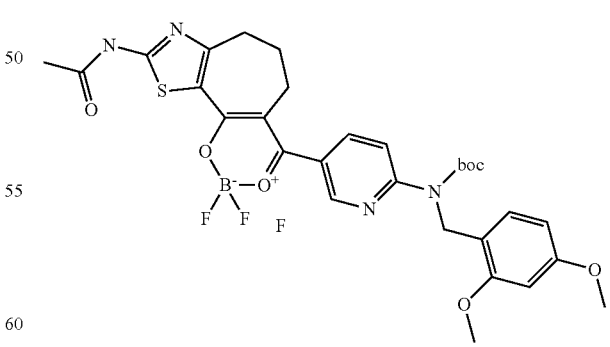

A-48 (4.0 g, 6.3 mmol) is taken up in 50 mL DCM, boron trifluoride diethyletherate (2.6 mL, 20 mmol) is added and the reaction mixture is stirred for 2 h at RT. The reaction mixture is concentrated under reduced pressure and used in the next step without purification. Yield: 4.5 g. HPLC-MS: $t_R$=2.23 min, $(M+H-boc)^+$=543.

A-50) [5-(2-Acetylamino-8-hydroxy-5,6-dihydro-
4H-cycloheptathiazole-7-carbonyl)-pyridin-2-yl]-
methyl-carbamic acid tert-butyl ester trifluoroborate

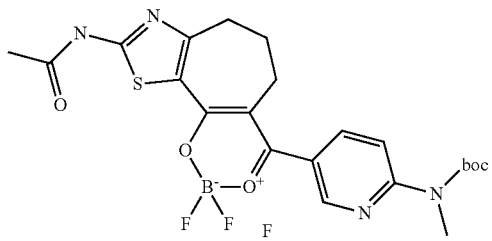

A-10 (10.5 g, 22.9 mmol) is taken up in 50 mL DCM, boron trifluoride diethyletherate (8.13 mL, 68.7 mmol) is added and the reaction mixture is stirred for 1 h at RT. The precipitated product is filtered off, triturated with diethyl ether and dried in vacuo at 40° C. Yield: 11.3 g. HPLC-MS: $t_R$=1.93 min, (M+H-boc)$^+$=407.

A-51) [5-(2-Acetylamino-8-hydroxy-5,6-dihydro-
4H-cycloheptathiazole-7-carbonyl)-pyridin-2-yl]-
ethyl-carbamic acid tert-butyl ester trifluoroborate

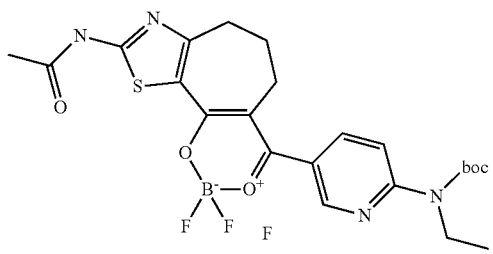

A-11 (5.00 g, 10.6 mmol) is taken up in 100 mL DCM, boron trifluoride diethyletherate (4.02 mL, 31.7 mmol) is added and the reaction mixture is stirred for 0.5 h at RT. The precipitated product is filtered off and dried in vacuo at 40° C. Yield: 6.36 g. HPLC-MS: $t_R$=2.38 min, (M+H)$^+$=521.

A-52) [7-(6-Fluoro-pyridine-3-carbonyl)-8-oxo-5,6,
7,8-tetrahydro-4H-cycloheptathiazol-2-yl]-thiocar-
bamic acid S-ethyl ester

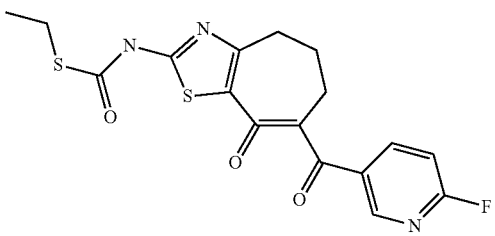

A-52 is prepared using general procedure A1 starting from A-13 (2.00 g, 7.40 mmol) and 6-fluoronicotinic acid chloride (1.53 g, 9.62 mmol). Yield: 2.59 g. HPLC-MS: $t_R$=double peak 2.47/2.68 min, (M+H)$^+$=394.

A-53) {7-[6-(2,4-Dimethoxy-benzylamino)-pyri-
dine-3-carbonyl]-8-oxo-5,6,7,8-tetrahydro-4H-cyclo-
heptathiazol-2-yl}-thiocarbamic acid S-ethyl ester

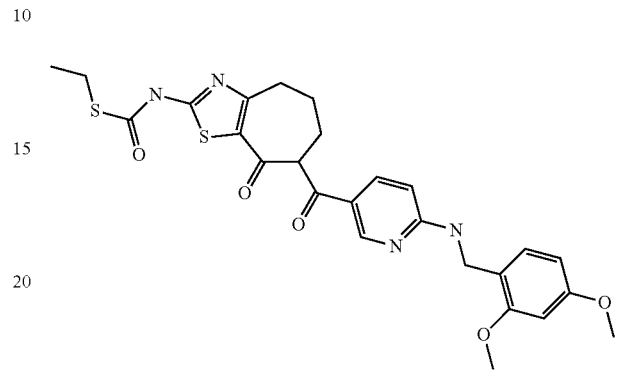

A-53 is prepared using general procedure A4 starting from A-52 (2.59 g, 6.58 mmol) and 2,4-dimethoxybenzylamine (2.47 mL, 16.5 mmol). Yield: 3.08 g. HPLC-MS: $t_R$=double peak 2.49/2.63 min, (M+H)$^+$=541.

A-54) {7-[6-Methylamino)-pyridine-3-carbonyl]-8-
oxo-5,6,7,8-tetrahydro-4H-cycloheptathiazol-2-yl}-
thiocarbamic acid S-ethyl ester

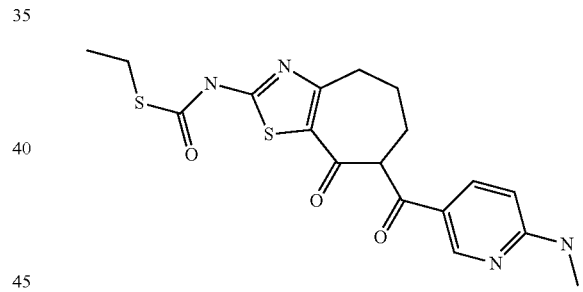

A-54 is prepared using general procedure A4 starting from A-52 (4.00 g, 10.2 mmol) and 40% methylamine in water (3.95 mL, 50.8 mmol). Yield: 1.45 g.

A-55) 1-Methyl-3-[7-(6-methylamino-pyridine-3-
carbonyl)-8-oxo-5,6,7,8-tetrahydro-4H-cyclohep-
tathiazol-2-yl]-urea

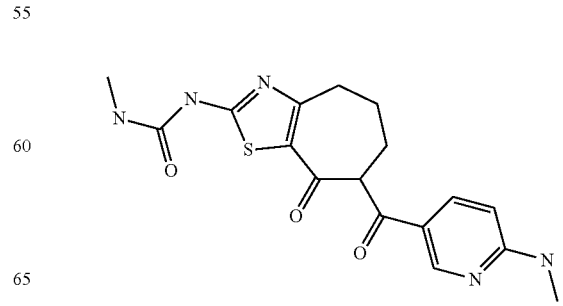

A-54 (0.50 g, 1.2 mmol) is taken up in 5 mL 2M methylamine in MeOH and stirred in a closed vial at 120° C. for 20 min. The reaction mixture is concentrated under reduced pressure. Yield: 0.46 g.

A-56) N-[7-(6-Amino-pyridine-3-carbonyl)-8-oxo-5,6,7,8-tetrahydro-4H-cycloheptathiazol-2-yl]-4-dimethylamino-butyramide

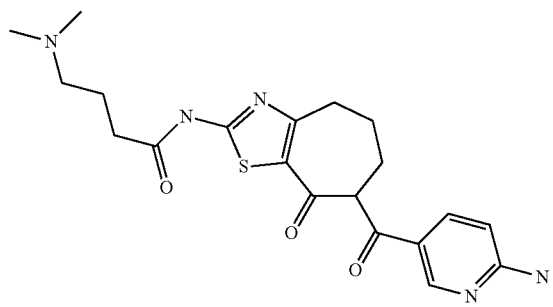

Example A-56 is prepared analogously to example A-27 starting from 4-dimethylamino-butyric acid hydrochloride (1.14 g, 6.81 mmol) and A-34 (1.76 g, 5.82 mmol). Yield: 0.35 g. HPLC-MS: $t_R$=1.41 min, $(M+H)^+$=416.

A-57) [7-(6-Chloro-pyridine-3-carbonyl)-8-oxo-5,6,7,8-tetrahydro-4H-cycloheptathiazol-2-yl]-thiocarbamic acid S-ethyl ester

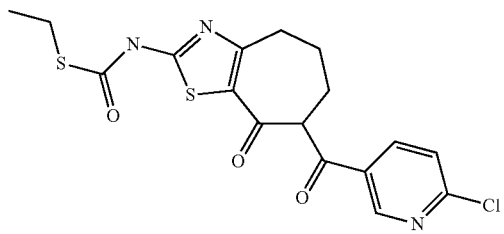

A-57 is prepared using general procedure A1 starting from A-13 (2.90 g, 10.7 mmol) and 6-chloronicotinic acid chloride (2.27 g, 12.9 mmol). Yield: 4.14 g. HPLC-MS: $t_R$=2.72 min, $(M+H)^+$=410/412.

A-58) N-[7-(3-Methyl-3H-imidazole-4-carbonyl)-8-oxo-5,6,7,8-tetrahydro-4H-cycloheptathiazol-2-yl]-acetamide

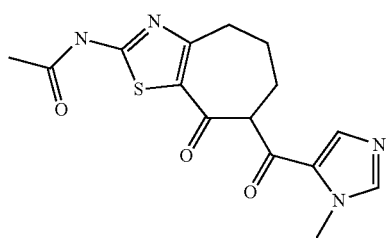

A-58 is prepared using general procedure A2 starting from A-02 (3.5 g, 15.6 mmol) and 3-methyl-3H-imidazole-4-carboxylic acid (3.15 g, 25.0 mmol). Yield: 1.64 g. HPLC-MS: $t_R$=1.68 min, $(M+H)^+$=333.

A-59) N-[7-(6-Amino-pyridine-3-carbonyl)-8-oxo-5,6,7,8-tetrahydro-4H-cycloheptathiazol-2-yl]-2-methoxy-acetamide

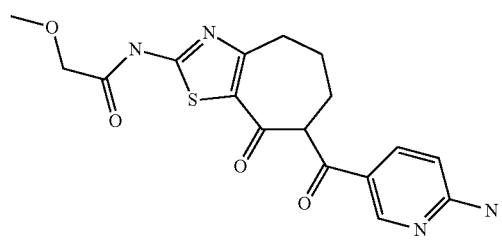

Example A-59 is prepared analogously to example A-31 starting from methoxyacetyl chloride (0.38 mL, 4.1 mmol) and A-37 (0.70 g, 1.6 mmol). Yield: 0.27 g. HPLC-MS: $t_R$=double peak 1.66/1.73 min, $(M+H)^+$=375.

A-60) N-[7-(6-Methylamino-pyridine-3-carbonyl)-8-oxo-5,6,7,8-tetrahydro-4H-cycloheptathiazol-2-yl]-2-methoxy-acetamide

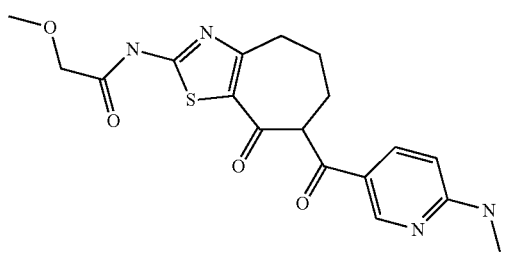

Example A-60 is prepared analogously to example A-31 starting from methoxyacetyl chloride (0.21 g, 1.9 mmol) and A-34 (0.50 g, 1.3 mmol). Yield: 0.72 g. HPLC-MS: $t_R$=1.99 min, $(M+H)^+$=389.

Example B

Examples B-01 to B-147 can be synthesized according to the following general procedures. The appropriate hydrazine and diketone required for synthesis can be deduced from the table of examples.

General Procedure B1:

The appropriate diketone (1 eq) and the appropriate hydrazine or hydrazine salt (1-10 eq) are added to acetic acid and the reaction mixture is heated to 60° C.-90° C. for 1-16 h. The acetic acid is removed under reduced pressure and the residue is taken up in water. The reaction mixture is neutralized to pH 5-6 with aqueous 10 N NaOH and extracted with DCM. The combined organic phases are washed with water and brine, dried over $MgSO_4$ and the solvents are removed under reduced pressure. The product may be purified by NP or RP column chromatography.

General Procedure B2:

The appropriate hydroxyketone trifluoroborate (1 eq) is added to DMSO and heated to 80° C. for 0.5-1 h. The appropriate hydrazine (1-10 eq) or hydrazine salt and potassium carbonate (both 3-10 eq) are added and the reaction mixture is heated at 80° C. for 1-6 h. The reaction mixture can be purified directly by RP column chromatography or can be worked up with water and ethylacetate and, after concentration under reduced pressure, be purified by NP or RP column chromatography.

TABLE 1

Examples B01-B147

| No. | MOLSTRUCTURE | Diketone/Hydrazine | [M + H]+ | $t_R$ (min.) |
| --- | --- | --- | --- | --- |
| B-01 | | A-22/isopropyl-hydrazine hydrochloride | 411 | 1.90 |
| B-02 | | A-21/ethyl-hydrazine hydrochloride | 383 | 1.60 |
| B-03 | | A-21/(2-methoxy-ethyl)-hydrazine hydrochloride | 413 | 1.62 |
| B-04 | | A-21/methyl hydrazine hydrochloride | 369 | 1.60 |
| B-05 | | A-21/isopropyl-hydrazine hydrochloride | 397 | 1.78 |
| B-06 | | A-21/ortho-tolyl-hydrazine hydrochloride | 445 | 1.82 |

TABLE 1-continued

Examples B01-B147

| No. | MOLSTRUCTURE | Diketone/Hydrazine | [M + H]$^+$ | $t_R$ (min.) |
|---|---|---|---|---|
| B-07 | | A-22/ortho-tolyl-hydrazine hydrochloride | 459 | 1.92 |
| B-08 | | A-18/cyclo-pentyl hydrazine hydrochloride | 408 | 2.06 |
| B-09 | | A-18/isopropyl-hydrazine hydrochloride | 382 | 1.86 |
| B-10 | | A-18/(1-prop-2-ynyl-piperidin-4-yl)-hydrazine hydrochloride | 461 | 1.81 |
| B-11 | | A-18/ortho-tolyl-hydrazine hydrochloride | 430 | 1.88 |

TABLE 1-continued

Examples B01-B147

| No. | MOLSTRUCTURE | Diketone/Hydrazine | [M + H]+ | $t_R$ (min.) |
|---|---|---|---|---|
| B-12 | | A-18/(1-cyclopropyl-piperidin-4-yl)-hydrazine hydrochloride | 463 | 1.90 |
| B-13 | | A-23/cyclo-hexyl hydrazine hydrochloride | 331 | 1.95 |
| B-14 | | A-23/isopropyl-hydrazine hydrochloride | 291 | 1.65 |
| B-15 | | A-19/n-propyl-hydrazine hydrochloride | 398 | 1.69 |
| B-16 | | A-19/(1-cyclopropyl-piperidin-4-yl)-hydrazine hydrochloride | 479 | 1.61 |
| B-17 | | A-18/(2-fluoro-phenyl)-hydrazine hydrochloride | 434 | 1.71 |

TABLE 1-continued

Examples B01-B147

| No. | MOLSTRUCTURE | Diketone/Hydrazine | [M + H]⁺ | t_R (min.) |
|---|---|---|---|---|
| B-18 | | A-18/3-chloro-4-hydrazino-N,N-dimethyl-benzamide hydrochloride | 521 | 1.65 |
| B-19 | | A-18/(2-bromo-phenyl)-hydrazine hydrochloride | 494/496 | 1.77 |
| B-20 | | A-18/4-hydrazino-piperidine-1-carboxylic acid ethyl ester hydrochloride | 495 | 1.76 |
| B-21 | | A-18/(2,6-dimethyl-phenyl)-hydrazine hydrochloride | 444 | 1.85 |
| B-22 | | A-18/sec-butyl-hydrazine hydrochloride | 396 | 1.72 |

TABLE 1-continued

Examples B01-B147

| No. | MOLSTRUCTURE | Diketone/Hydrazine | [M + H]⁺ | t_R (min.) |
|---|---|---|---|---|
| B-23 | | A-18/(2-chloro-phenyl)-hydrazine hydrochloride | 450 | 1.80 |
| B-24 | | A-18/(2,6-difluoro-phenyl)-hydrazine hydrochloride | 452 | 1.74 |
| B-25 | | A-18/allyl-hydrazine hydrochloride | 380 | 1.63 |
| B-26 | | A-18/(2-methoxy-ethyl)-hydrazine hydrochloride | 398 | 1.54 |
| B-27 | | A-14/isopropyl-hydrazine hydrochloride | 426 | 1.73 |
| B-28 | | A-21/(2-chloro-phenyl)-hydrazine hydrochloride | 465 | 1.78 |

TABLE 1-continued

Examples B01-B147

| No. | MOLSTRUCTURE | Diketone/Hydrazine | [M + H]$^+$ | $t_R$ (min.) |
|---|---|---|---|---|
| B-29 | | A-16/isopropyl-hydrazine hydrochloride | 412 | 1.34 |
| B-30 | | A-21/bicyclo[2.2.1]hept-2-yl-hydrazine hydrochloride | 449 | 2.12 |
| B-31 | | A-19/sec-butyl-hydrazine hydrochloride | 412 | 1.70 |
| B-32 | | A-19/(2-methyl-allyl)-hydrazine hydrochloride | 410 | 1.56 |
| B-33 | | A-16/n-propyl-hydrazine hydrochloride | 412 | 1.32 |
| B-34 | | A-15/ortho-tolyl-hydrazine hydrochloride | 488 | 1.85 |

TABLE 1-continued
Examples B01-B147
| No. | MOLSTRUCTURE | Diketone/Hydrazine | [M + H]+ | $t_R$ (min.) |
|---|---|---|---|---|
| B-35 | 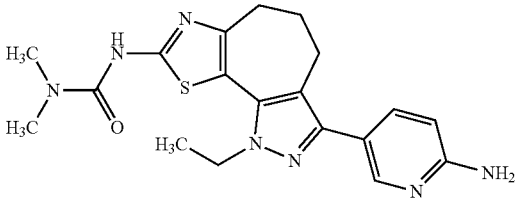 | A-16/ethyl-hydrazine hydrochloride | 398 | 1.22 |
| B-36 | 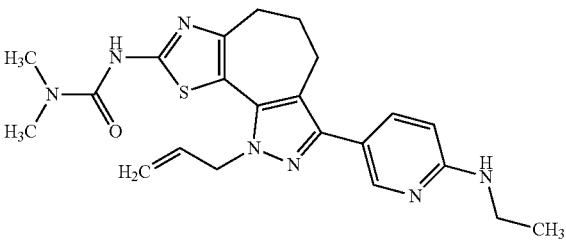 | A-15/allyl-hydrazine hydrochloride | 438 | 1.71 |
| B-37 | 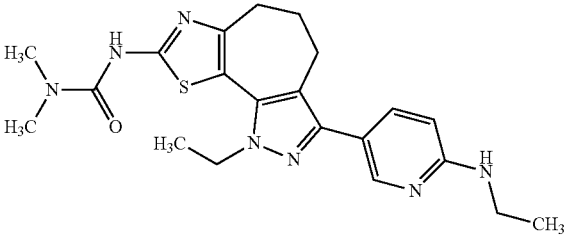 | A-15/ethyl-hydrazine hydrochloride | 426 | 1.71 |
| B-38 | 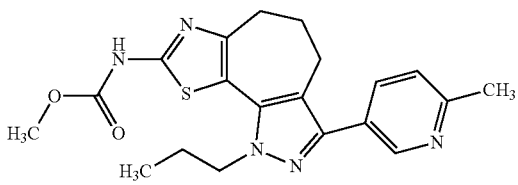 | A-19/allyl-hydrazine hydrochloride | 396 | 1.45 |
| B-39 | 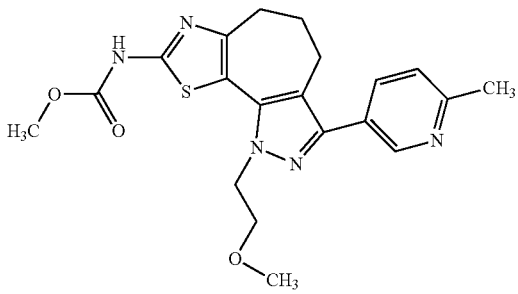 | A-19/(2-methoxy-ethyl)-hydrazine hydrochloride | 414 | 1.44 |
| B-40 | 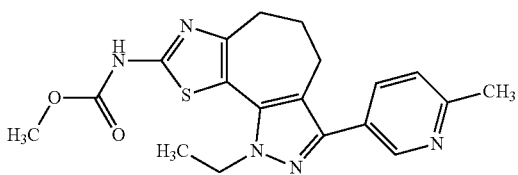 | A-19/ethyl-hydrazine hydrochloride | 384 | 1.49 |

TABLE 1-continued

Examples B01-B147

| No. | MOLSTRUCTURE | Diketone/Hydrazine | [M + H]⁺ | t_R (min.) |
|---|---|---|---|---|
| B-41 | | A-19/(2-chloro-phenyl)-hydrazine hydrochloride | 466 | 1.59 |
| B-42 | | A-19/ortho-tolyl-hydrazine hydrochloride | 446 | 1.67 |
| B-43 | | A-14/(2-fluoro-phenyl)-hydrazine hydrochloride | 478 | 1.72 |
| B-44 | | A-14/(2-bromo-phenyl)-hydrazine hydrochloride | 538 | 1.80 |
| B-45 | | A-14/(2-chloro-phenyl)-hydrazine hydrochloride | 494 | 1.76 |
| B-46 | | A-14/ortho-tolyl-hydrazine hydrochloride | 474 | 1.79 |

TABLE 1-continued

Examples B01-B147

| No. | MOLSTRUCTURE | Diketone/Hydrazine | [M + H]⁺ | t_R (min.) |
|---|---|---|---|---|
| B-47 | | A-14/allyl-hydrazine hydrochloride | 424 | 1.62 |
| B-48 | | A-14/ethyl-hydrazine hydrochloride | 412 | 1.58 |
| B-49 | | A-16/(1-cyclopropyl-piperidin-4-yl)-hydrazine hydrochloride | 493 | 1.42 |
| B-50 | | A-17/ortho-tolyl-hydrazine hydrochloride | 461 | 1.39 |
| B-51 | | A-16/(2-methoxy-ethyl)-hydrazine hydrochloride | 428 | 1.17 |
| B-52 | | A-16/allyl-hydrazine hydrochloride | 410 | 1.25 |

TABLE 1-continued

Examples B01-B147

| No. | MOLSTRUCTURE | Diketone/Hydrazine | [M + H]+ | $t_R$ (min.) |
|---|---|---|---|---|
| B-53 | | A-16/(1-methyl-piperidin-4-yl)-hydrazine hydrochloride | 467 | 1.26 |
| B-54 | | A-16/(2-chloro-phenyl)-hydrazine hydrochloride | 480/482 | 1.43 |
| B-55 | | A-16/ortho-tolyl-hydrazine hydrochloride | 460 | 1.48 |
| B-56 | | A-14/(1-methyl-piperidin-4-yl)-hydrazine hydrochloride | 481 | 1.36 |
| B-57 | | A-14/(1-cyclopropyl-piperidin-4-yl)-hydrazine hydrochloride | 507 | 1.51 |
| B-58 | | A-19/methyl-hydrazine hydrochloride | 370 | 1.43 |

TABLE 1-continued

Examples B01-B147

| No. | MOLSTRUCTURE | Diketone/Hydrazine | [M + H]$^+$ | $t_R$ (min.) |
|---|---|---|---|---|
| B-59 | | A-15/(2-methoxy-ethyl)-hydrazine hydrochloride | 456 | 1.43 |
| B-60 | | A-11/(tetrahydro-pyran-3-yl)-hydrazine hydrochloride | 453 | 1.72 |
| B-61 | | A-12/ortho-tolyl-hydrazine hydrochloride | 431 | 1.43 |
| B-62 | | A-12/(2-fluoro-phenyl)-hydrazine hydrochloride | 435 | 1.35 |
| B-63 | | A-12/(2-bromo-phenyl)-hydrazine hydrochloride | 495/497 | 1.41 |

TABLE 1-continued
Examples B01-B147
| No. | MOLSTRUCTURE | Diketone/Hydrazine | [M + H]⁺ | $t_R$ (min.) |
|---|---|---|---|---|
| B-64 | 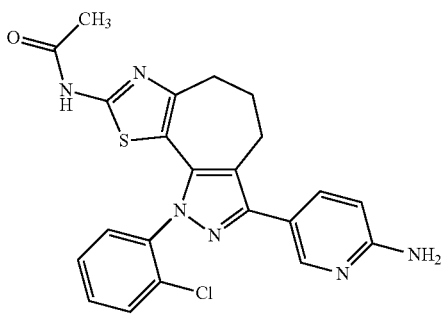 | A-12/(2-chloro-phenyl)-hydrazine hydrochloride | 451 | 1.39 |
| B-65 | 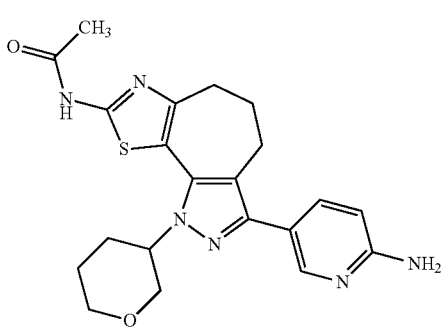 | A-12/(tetrahydro-pyran-3-yl)-hydrazine-hydrazine hydrochloride | 425 | 1.30 |
| B-66 | 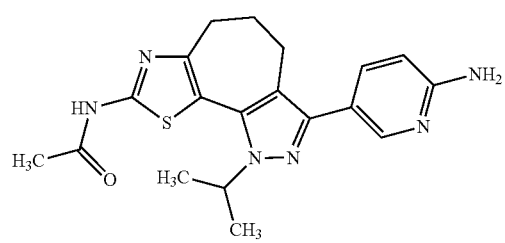 | A-12/isopropyl-hydrazine hydrochloride | 383 | 1.35 |
| B-67 | 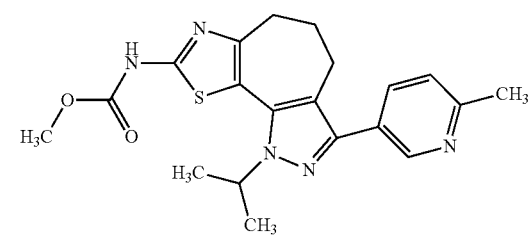 | A-19/isopropyl-hydrazine hydrochloride | 398 | 1.63 |
| B-68 | 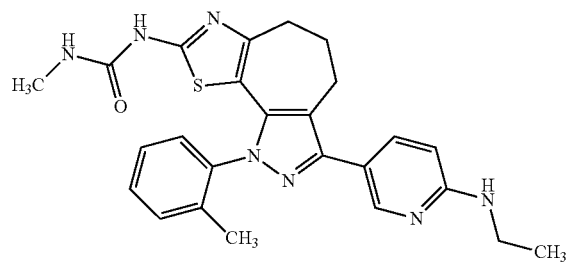 | A-26/ortho-tolyl-hydrazine hydrochloride | 474 | 1.72 |

TABLE 1-continued

Examples B01-B147

| No. | MOLSTRUCTURE | Diketone/Hydrazine | [M + H]+ | t_R (min.) |
|---|---|---|---|---|
| B-69 | | A-27/ortho-tolyl-hydrazine hydrochloride | 488 | 1.60 |
| B-70 | | A-28/ortho-tolyl-hydrazine hydrochloride | 530 | 1.82 |
| B-71 | | A-29/ortho-tolyl-hydrazine hydrochloride | 503 | 1.79 |
| B-72 | | A-30/ortho-tolyl-hydrazine hydrochloride | 553 | 1.68 |
| B-73 | | A-24/isopropyl-hydrazine hydrochloride | 335 | 0.84 |

TABLE 1-continued

Examples B01-B147

| No. | MOLSTRUCTURE | Diketone/Hydrazine | [M + H]$^+$ | t$_R$ (min.) |
|---|---|---|---|---|
| B-74 | | A-22/(2-bromo-phenyl)-hydrazine hydrochloride | 523/525 | 1.72 |
| B-75 | | A-22/(2-chloro-phenyl)-hydrazine hydrochloride | 479/481 | 1.71 |
| B-76 | | A-22/(2-fluoro-phenyl)-hydrazine hydrochloride | 463 | 1.67 |
| B-77 | | A-51/(3-methyl-pyridin-4-yl)-hydrazine | 460 | 1.55 |
| B-78 | | A-51/(2-methoxymethyl-phenyl)-hydrazine | 475 | 1.55 |

TABLE 1-continued

Examples B01-B147

| No. | MOLSTRUCTURE | Diketone/Hydrazine | [M + H]+ | $t_R$ (min.) |
|---|---|---|---|---|
| B-79 | | A-51/(2-ethyl-phenyl)-hydrazine | 473 | 1.73 |
| B-80 | | A-50/pyridin-3-ylmethyl-hydrazine | 446 | 1.39 |
| B-81 | | A-50/(2-fluoro-phenyl)-hydrazine | 449 | 1.45 |
| B-82 | | A-50/(2-morpholin-4-yl-ethyl)-hydrazine | 468 | 1.36 |
| B-83 | | A-50/(tetrahydro-pyran-3-yl)-hydrazine hydrochloride | 439 | 1.40 |

TABLE 1-continued

Examples B01-B147

| No. | MOLSTRUCTURE | Diketone/Hydrazine | [M + H]+ | $t_R$ (min.) |
|---|---|---|---|---|
| B-84 | | A-50/pyridin-3-yl-hydrazine | 432 | 1.28 |
| B-85 | | A-50/(3-methyl-pyridin-4-yl)-hydrazine | 446 | 0.15 |
| B-86 | | A-50/isobutyl-hydrazine | 411 | 1.52 |
| B-87 | | A-50/phenyl-hydrazine | 431 | 1.49 |
| B-88 | | A-50/(2-ethyl-phenyl)-hydrazine | 459 | 1.62 |

TABLE 1-continued

Examples B01-B147

| No. | MOLSTRUCTURE | Diketone/Hydrazine | [M + H]⁺ | $t_R$ (min.) |
|---|---|---|---|---|
| B-89 | | A-50/(3-methoxy-phenyl)-hydrazine | 461 | 1.52 |
| B-90 | | A-18/(3-methyl-pyridin-4-yl)-hydrazine | 431 | 1.41 |
| B-91 | | A-18/(3-methoxy-phenyl)-hydrazine | 446 | 1.63 |
| B-92 | | A-18/n-propyl-hydrazine hydrochloride | 382 | 1.53 |
| B-93 | | A-58/ortho-tolyl-hydrazine hydrochloride | 419 | 1.42 |

TABLE 1-continued

Examples B01-B147

| No. | MOLSTRUCTURE | Diketone/Hydrazine | [M + H]+ | $t_R$ (min.) |
|---|---|---|---|---|
| B-94 | | A-58/phenyl-hydrazine | 405 | 1.46 |
| B-95 | | A-18/pyridin-3-yl-hydrazine | 417 | 1.34 |
| B-96 | | A-16/phenyl-hydrazine | 446 | 1.50 |
| B-97 | | A-16/(2-fluoro-phenyl)-hydrazine hydrochloride | 464 | 1.47 |
| B-98 | | A-14/(2-morpholin-4-yl-ethyl)-hydrazine | 497 | 1.36 |
| B-99 | | A-32/ortho-tolyl-hydrazine hydrochloride | 474 | 1.64 |

TABLE 1-continued

Examples B01-B147

| No. | MOLSTRUCTURE | Diketone/Hydrazine | [M + H]⁺ | t_R (min.) |
|---|---|---|---|---|
| B-100 | | A-31/ortho-tolyl-hydrazine hydrochloride | 489 | 1.82 |
| B-101 | | A-35/(2-fluoro-phenyl)-hydrazine hydrochloride | 450 | 1.05 |
| B-102 | | A-35/ortho-tolyl-hydrazine hydrochloride | 446 | 1.16 |
| B-103 | | A-36/ortho-tolyl-hydrazine hydrochloride | 475 | 1.43 |
| B-104 | | A-59/ortho-tolyl-hydrazine hydrochloride | 461 | 1.28 |
| B-105 | | A-33/(2-morpholin-4-yl-ethyl)-hydrazine | 454 | 1.17 |

TABLE 1-continued

Examples B01-B147

| No. | MOLSTRUCTURE | Diketone/Hydrazine | [M + H]⁺ | t_R (min.) |
|---|---|---|---|---|
| B-106 | | A-38/ortho-tolyl-hydrazine hydrochloride | 489 | 1.58 |
| B-107 | | A-60/ortho-tolyl-hydrazine hydrochloride | 475 | 1.42 |
| B-108 | | A-39/ortho-tolyl-hydrazine hydrochloride | 530 | 1.38 |
| B-109 | | A-40/ortho-tolyl-hydrazine hydrochloride | 525 | 1.43 |
| B-110 | | A-43/(2-dimethylamino-ethyl)-hydrazine hydrochloride | 386 | 1.10 |
| B-111 | | A-43/(2-fluoro-phenyl)-hydrazine hydrochloride | 409 | 1.15 |

TABLE 1-continued

Examples B01-B147

| No. | MOLSTRUCTURE | Diketone/Hydrazine | [M + H]⁺ | $t_R$ (min.) |
|---|---|---|---|---|
| B-112 | | A-43/ortho-tolyl-hydrazine hydrochloride | 405 | 1.24 |
| B-113 | | A-43/isobutyl-hydrazine hydrochloride | 371 | 1.24 |
| B-114 | | A-43/3-chloro-4-hydrazino-N,N-dimethyl-benzamide | 496/498 | 1.18 |
| B-115 | | A-43/[1-(4-hydrazino-phenyl)-cyclopropyl]-dimethyl-amine | 474 | 1.32 |
| B-116 | | A-43e/(2-chloro-phenyl)-hydrazine hydrochloride | 425 | 1.22 |

TABLE 1-continued

Examples B01-B147

| No. | MOLSTRUCTURE | Diketone/Hydrazine | [M + H]⁺ | t_R (min.) |
|-----|---|---|---|---|
| B-117 | | A-43/(2-methoxy-phenyl)-hydrazine hydrochloride | 421 | 1.25 |
| B-118 | | A-43/(2-ethyl-phenyl)-hydrazine hydrochloride | 419 | 1.34 |
| B-119 | | A-46/(2-dimethylamino-ethyl)-hydrazine hydrochloride | 400 | 1.18 |
| B-120 | | A-46/ortho-tolyl-hydrazine hydrochloride | 419 | 1.30 |
| B-121 | | A-46/isobutyl-hydrazine hydrochloride | 385 | 1.30 |

TABLE 1-continued

Examples B01-B147

| No. | MOLSTRUCTURE | Diketone/Hydrazine | [M + H]⁺ | $t_R$ (min.) |
|---|---|---|---|---|
| B-122 | | A-51/phenyl-hydrazine | 445 | 1.61 |
| B-123 | | A-51/tert-butyl-hydrazine | 425 | 1.72 |
| B-124 | | A-51/(2-morpholin-4-yl-ethyl)-hydrazine | 482 | 1.47 |
| B-125 | | A-51/(2-methoxy-ethyl)-hydrazine | 427 | 1.40 |
| B-126 | | A-51/(2-methoxy-1-methyl-ethyl)-hydrazine | 441 | 1.51 |

TABLE 1-continued

Examples B01-B147

| No. | MOLSTRUCTURE | Diketone/Hydrazine | [M + H]+ | $t_R$ (min.) |
|---|---|---|---|---|
| B-127 | | A-51/pyridin-3-yl-hydrazine | 446 | 1.30 |
| B-128 | | A-51/(3-methoxy-phenyl)-hydrazine | 475 | 1.64 |
| B-129 | | A-51/allyl-hydrazine hydrochloride | 409 | 1.48 |
| B-130 | | A-49/ethyl-hydrazine | 369 | 1.21 |
| B-131 | | A-49/n-propyl-hydrazine | 383 | 1.19 |
| B-132 | | A-49/(2-methoxy-ethyl)-hydrazine | 399 | 1.18 |

US 8,288,379 B2
TABLE 1-continued
Examples B01-B147
| No. | MOLSTRUCTURE | Diketone/Hydrazine | [M + H]+ | $t_R$ (min.) |
|---|---|---|---|---|
| B-133 | 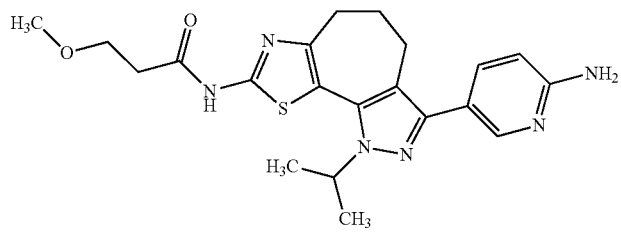 | A-36/isopropyl-hydrazine hydrochloride | 427 | 1.36 |
| B-134 | 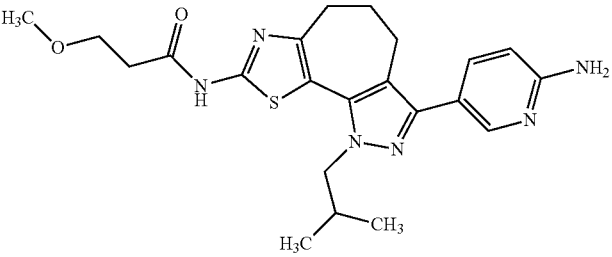 | A-36/isobutyl-hydrazine hydrochloride | 441 | 0.16 |
| B-135 | 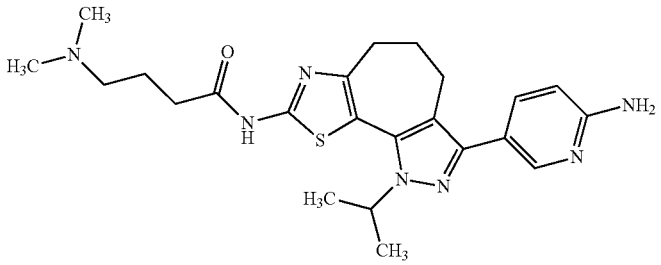 | A-56/isopropyl-hydrazine hydrochloride | 454 | 1.57 |
| B-136 | 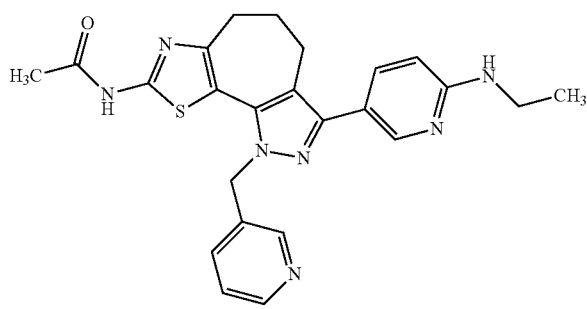 | A-11/pyridin-3-ylmethyl-hydrazine | 460 | 1.44 |
| B-137 | 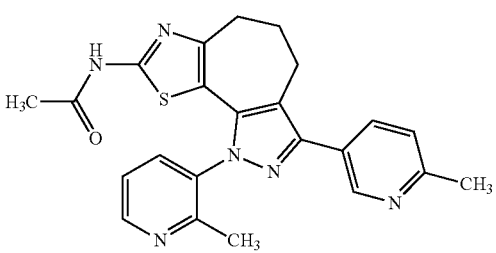 | A-18/(2-methyl-pyridin-3-yl)-hydrazine hydrochloride | 431 | 1.33 |

TABLE 1-continued

Examples B01-B147

| No. | MOLSTRUCTURE | Diketone/Hydrazine | [M + H]+ | $t_R$ (min.) |
|---|---|---|---|---|
| B-138 | | A-33/(2-methyl-pyridin-3-yl)-hydrazine hydrochloride | 432 | 0.27 |
| B-139 | | A-10/(2-methyl-pyridin-3-yl)-hydrazine hydrochloride | 446 | 1.28 |
| B-140 | | A-26/isopropyl-hydrazine hydrochloride | 426 | 1.67 |
| B-141 | | A-15/(2-methyl-pyridin-3-yl)-hydrazine hydrochloride | 489 | 1.56 |
| B-142 | | A-55/ortho-tolyl-hydrazine hydrochloride | 460 | 1.58 |

TABLE 1-continued

Examples B01-B147

| No. | MOLSTRUCTURE | Diketone/Hydrazine | [M + H]+ | t_R (min.) |
|---|---|---|---|---|
| B-143 | | A-55/(2-methyl-pyridin-3-yl)-hydrazine hydrochloride | 461 | 1.39 |
| B-144 | | A-55/isopropyl-hydrazine hydrochloride | 412 | 1.54 |
| B-145 | | A-34/(2-fluoro-phenyl)-hydrazine hydrochloride | 393 | 0.89 |
| B-146 | | A-53/ortho-tolyl-hydrazine hydrochloride | 477 | 2.19 |
| B-147 | | A-57/(2-fluoro-phenyl)-hydrazine hydrochloride | 500/502 | 2.68 |

B-148) 1-[3-(6-Amino-pyridin-3-yl)-1-o-tolyl-1,4,5,6-tetrahydro-9-thia-1,2,7-triaza-cyclopenta[e]azulen-8-yl]-3-methyl-urea

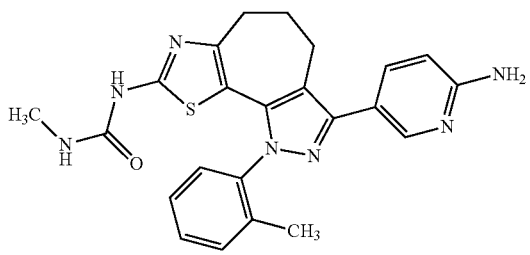

Example B-146 (0.13 g, 0.26 mmol) is taken up in 1 mL NMP, 40% methylamine in THF (0.52 mL, 1.0 mmol) is added and the reaction mixture is heated to 120° C. for 10 min using microwave irradiation. The product is purified by HPLC (C18, 50-98% MeOH in water containing 0.1% formic acid). Yield: 70 mg. HPLC-MS: $t_R$=1.95 min, (M+H)$^+$=446.

B-149) 1-[3-(6-Chloro-pyridin-3-yl)-1-o-tolyl-1,4,5,6-tetrahydro-9-thia-1,2,7-triaza-cyclopenta[e]azulen-8-yl]-3-methyl-urea

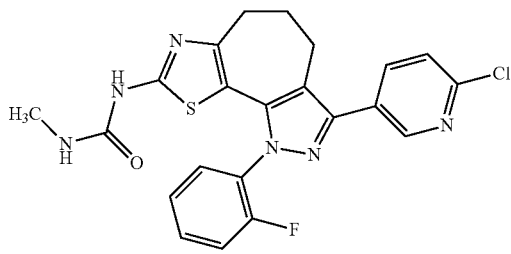

Example B-147 (0.20 g, 0.40 mmol) is taken up in 2 mL NMP, 40% methylamine in THF (0.40 mL, 0.80 mmol) is added and the reaction mixture is heated to 120° C. for 10 min using microwave irradiation. The product is purified by HPLC (C18, 50-98% MeOH in water containing 0.1% formic acid). Yield: 105 mg. HPLC-MS: $t_R$=2.54 min, (M+H)$^+$=469/471.

B-150) 1-[1-(2-Fluoro-phenyl)-3-(6-methylamino-pyridin-3-yl)-1,4,5,6-tetrahydro-9-thia-1,2,7-triaza-cyclopenta[e]azulen-8-yl]-3-methyl-urea

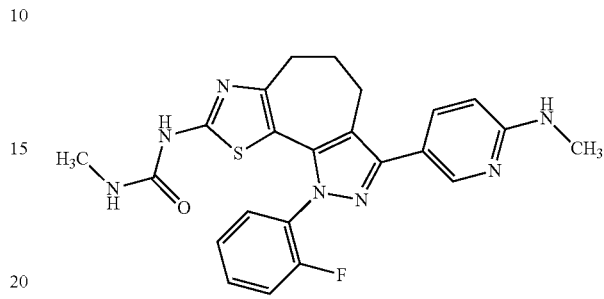

Example B-149 (0.11 g, 0.22 mmol), 40% methylamine in THF (0.56 mL, 1.1 mmol), palladium(II) acetate (1 mg), (R)-1-[(1S)-2-(diphenylphosphino)ferrocenyl]-ethyl-di-tert-butyl phosphine (1.2 mg) and sodium tert-butoxide (24 mg) are added to 1 mL dimethoxyethane and stirred overnight under an argon atmosphere at 100° C. The reaction mixture is poured in water and extracted with ethylacetate. The combined organic phases are dried over MgSO$_4$ and concentrated under reduced pressure. The residue is purified by HPLC (C18, 50-98% MeOH in water containing 0.1% formic acid). Yield: 23 mg. HPLC-MS: $t_R$=1.46 min, (M+H)$^+$=464.

Example C

Examples C-01 to C-07 can be synthesized from examples B according to the following general procedure. The appropriate example B required for synthesis can be deduced from the table of examples.

General Procedure C:

The appropriate example B (1 eq) is taken up in dioxane, concentrated hydrochloric acid (10 eq) are added and the reaction mixture is stirred at 95° C. for 1-3 h. The reaction mixture is concentrated under reduced pressure and the product is purified by HPLC (C18, 5-98% acetonitrile in water containing 0.1% formic acid).

TABLE 2

Examples C01-C07

| No. | MOLSTRUCTURE | Example B | [M + H]$^+$ | $t_R$ [min] |
|---|---|---|---|---|
| C-01 | | B-09 | 340 | 1.51 |

TABLE 2-continued

Examples C01-C07

| No. | MOLSTRUCTURE | Example B | [M + H]⁺ | $t_R$ [min] |
|---|---|---|---|---|
| C-02 | | B-11 | 388 | 1.57 |
| C-03 | | B-07 | 417 | 1.73 |
| C-04 | | B-61 | 389 | 1.30 |
| C-05 | | B-14 | 249 | 1.51 |
| C-06 | | B-139 | 404 | 1.30 |
| C-07 | | B-77 | 418 | 1.55 |

C-08) 1-Isopropyl-1,4,5,6-tetrahydro-9-thia-1,2,7-triaza-cyclopent[e]azulene

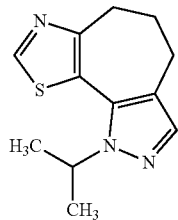

A mixture of C-05 (0.10 g, 0.40 mmol), tert-butylnitrite (65 µL, 0.49 mmol) and methanol (0.10 mL) is taken up in 2 mL acetonitrile and stirred for 1 h. at 60° C. The reaction mixture is concentrated under reduced pressure and the product is purified by HPLC (C18, 5-98% acetonitrile in water containing 0.1% trifluoroacetic acid). HPLC-MS: $t_R$=1.72 min, $(M+H)^+$=234. $^1$H NMR (DMSO-d6): δ 9.1 (s, 1H), 7.4 (s, 1H), 4.9 (m, 1H), 3.1 (t, 2H), 2.7 (t, 2H), 2.0 (quint, 2H), 1.4 (2, 6H).

Example D

Examples D-01 to D-07 can be synthesized from examples C according to the following general procedure. The appropriate amine and example C required for synthesis can be deduced from the table of examples.

General Procedure D:

The appropriate example C (1 eq) is taken up in acetonitrile, DBU (2 eq) and CDI (2 eq) are added and the reaction mixture is stirred overnight at 100° C. Amine is added and the reaction mixture is again stirred overnight at 100° C. The reaction mixture is concentrated under reduced pressure and the product is purified by HPLC (C18, 5-98% acetonitrile in water containing 0.1% formic acid)

TABLE 3

| | Examples D01-D07 | | | |
|---|---|---|---|---|
| No. | MOLSTRUCTURE | Example C/Amine | $[M + H]^+$ | $t_R$ [min] |
| D-01 | | C-01/dimethyl-amine | 411 | 1.79 |
| D-02 | | C-01/methyl amine | 397 | 1.80 |
| D-03 | | C-01/O-methyl-hydroxylamine | 413 | 1.55 |
| D-04 | | C-02/ammonia | 431 | 1.45 |

TABLE 3-continued

Examples D01-D07

| No. | MOLSTRUCTURE | Example C/Amine | [M + H]+ | $t_R$ [min] |
|---|---|---|---|---|
| D-05 | | C-02/methyl-amine | 445 | 1.57 |
| D-06 | | C-02/2-methoxy-ethyl-amine | 489 | 1.61 |
| D-07 | | C-02/N¹,N¹-dimethyl-ethane-1,2-diamine | 502 | 1.60 |

Example E

Examples E-01 to E-18 can be synthesized from examples B-73, B-14 or C according to the following general procedures. The appropriate amine or acid required for synthesis can be deduced from the table of examples.

General Procedure E1:

The example B-73 (1 eq) is taken up in DMA, DIPEA (2.5 eq) and HATU (1.3 eq) are added and the reaction mixture is stirred for 10 min at RT. Amine is added and the reaction mixture is stirred overnight at RT followed by 1 h at 55° C. The product can be purified by HPLC (C18, 5-98% acetonitrile in water containing 0.1% formic acid).

General Procedure E2:

The acid (1-3 eq) is taken up in NMP, DIPEA (3.5 eq) and HATU (2-4 eq) are added and the reaction mixture is stirred for 10 min at RT. Example B-145 or C (1 eq.) is added and the reaction mixture is stirred overnight at 60° C. The product can be purified by HPLC (C18, 5-98% acetonitrile in water containing 0.1% formic acid).

TABLE 4

Examples E01-E18

| No. | MOLSTRUCTURE | Amine or acid | [M + H]+ | $t_R$ [min] |
|---|---|---|---|---|
| E-01 | | methyl-amine | 348 | 1.44 |

TABLE 4-continued

Examples E01-E18

| No. | MOLSTRUCTURE | Amine or acid | [M + H]+ | $t_R$ [min] |
|---|---|---|---|---|
| E-02 | | dimethyl-amine | 362 | 1.47 |
| E-03 | | N,N,N'-trimethyl-ethane-1,2-diamine | 419 | 1.47 |
| E-04 | | 2-amino-ethanol | 378 | 1.18 |
| E-05 | | 2-methylamino-ethanol | 392 | 1.20 |
| E-06 | | 3-amino-propan-1-ol | 392 | 1.23 |

TABLE 4-continued

Examples E01-E18

| No. | MOLSTRUCTURE | Amine or acid | [M + H]⁺ | t_R [min] |
|---|---|---|---|---|
| E-07 | | 2-methoxy-ethylamine | 392 | 1.38 |
| E-08 | | (2-methoxy-ethyl)-methyl-amine | 406 | 1.46 |
| E-09 | | phenylamine | 410 | 1.79 |
| E-10 | | 1H-pyrazol-3-ylamine | 400 | 1.45 |
| E-11 | | 3-amino-propionic acid methyl ester | 420 | 1.43 |

TABLE 4-continued
Examples E01-E18
| No. | MOLSTRUCTURE | Amine or acid | [M + H]+ | t_R [min] |
|---|---|---|---|---|
| E-12 | 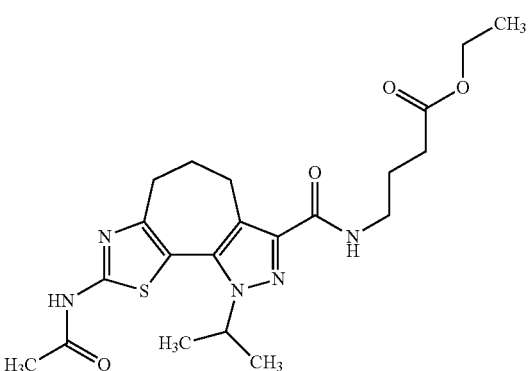 | 4-amino-butyric acid ethyl ester | 448 | 1.61 |
| E-13 | 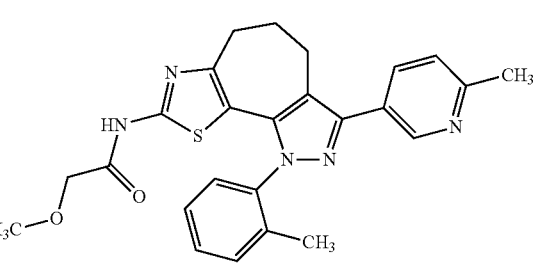 | 2-methoxy-acetic acid | 460 | 1.43 |
| E-14 | 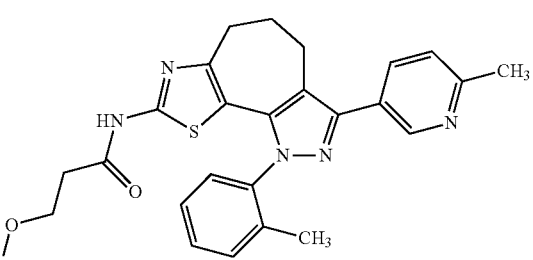 | 3-methoxy-propionic acid | 474 | 1.59 |
| E-15 | 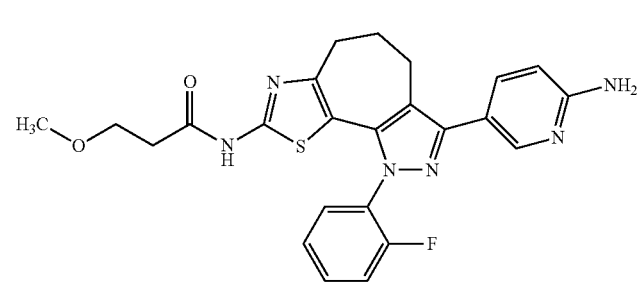 | 3-methoxy-propionic acid | 479 | 1.34 |
| E-16 | 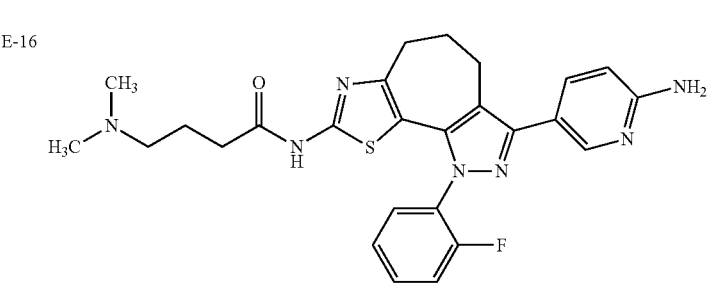 | 4-dimethylamino-butyric acid | 506 | 1.53 |

TABLE 4-continued

Examples E01-E18

| No. | MOLSTRUCTURE | Amine or acid | [M + H]⁺ | $t_R$ [min] |
|---|---|---|---|---|
| E-17 | | N,N-dimethyl-glycine | 478 | 1.42 |
| E-18 | | 2-methoxy-acetic acid | 465 | 1.22 |

Example F

F-01) 8-Bromo-1-methyl-1,4,5,6-tetrahydro-9-thia-1,2,7-triaza-cyclopent[e]azulene A mixture of A-23 (5.0 g, 20 mmol) and methyl hydrazine sulfate (14 g, 0.10 mol) in acetic acid is stirred overnight at RT. The reaction mixture is filtered and the solids are dried in vacuo. Yield: 7.0 g. $R_f$ (silica on alumina, ethylacetate)=0.40. MS (M+H)=263. ¹H NMR to (DMSO-d6): δ 7.2 (s, 1H), 4.0 (s, 3H), 3.0 (m, 2H), 2.7 (m, 2H), 2.2 (s, 3H), 1.9 (m, 2H).

F-01a) N-(1-Methyl-1,4,5,6-tetrahydro-9-thia-1,2,7-triaza-cyclopent[e]azulen-8-yl)-acetamide

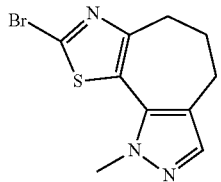

F-01b) 1-Methyl-1,4,5,6-tetrahydro-9-thia-1,2,7-triaza-cyclopent[e]azulen-8-ylamine

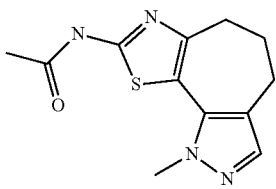

To a mixture of F-01a (7.0 g, 20 mmol) in 100 mL water is added 20 mL conc. hydrochloric acid and the reaction mixture is stirred overnight at 80° C. The reaction mixture is cooled to 0° C., neutralized with saturated aqueous NaHCO₃ and extracted with DCM. The combined organic phases are dried over MgSO₄ and concentrated under reduced pressure. Yield: 3.5 g. $R_f$ (silica on alumina, 10% MeOH in CHCl₃) =0.30. MS (M+H)=221. ¹H NMR (DMSO-d6): δ 7.2 (s, 1H), 7.1 (s, 2H), 3.9 (s, 3H), 2.8 (m, 2H), 2.6 (m, 2H), 1.8 (m, 2H).

At 0° C. tert-butylnitrite (2.1 mL, 18 mmol) and CuBr₂ (3.6 g, 16 mmol) is added to a mixture of F-01b (3.0 g, 14 mmol) in 25 mL acetonitrile and the reaction mixture is stirred for 2 h. The reaction is quenched by the addition of 10% sulfuric acid in water and extracted with DCM. The combined organic phases are dried over MgSO₄ and concentrated under reduced pressure. The product is purified by flash column chromatography (silica gel, 20% ethyl acetate in petroleum ether). Yield: 2.0 g. $R_f$ (silica on alumina, 10% MeOH in CHCl₃)=0.88. MS (M+H)=284/286. ¹H NMR (DMSO-d6): δ 7.3 (s, 1H), 4.0 (s, 3H), 3.2 (m, 2H), 2.8 (m, 2H), 1.9 (m, 2H).

Examples F-02 to F-10 can be synthesized from example F-01 according to the following general procedure. The appropriate amine required for synthesis can be deduced from the table of examples.

General Procedure F:

F-01 (1 eq) is taken up in NMP, potassium carbonate (2.5 eq) and amine (1.5 eq) are added and the reaction mixture is stirred overnight at 80° C. The product can be purified by HPLC (C18, 5-98% acetonitrile in water containing 0.1% formic acid).

TABLE 5

Examples F02-F10

| No. | MOLSTRUCTURE | Amine | [M + H]$^+$ | $t_R$ [min] |
|---|---|---|---|---|
| F-02 | | 3-pyrrolidinol | 291 | 1.16 |
| F-03 | | morpholine | 291 | 1.36 |
| F-04 | Chiral | (S)-1-pyrrolidin-2-yl-methanol | 305 | 1.31 |
| F-05 | Chiral | (1S,4S)-2oxa-5-aza-bicyclo[2.2.1]heptane | 303 | 1.27 |
| F-06 | | N-pyrrolidin-3-yl-acetamide | 332 | 1.15 |
| F-07 | Chiral | (R)-pyrrolidin-3-yl-carbamic acid tert-butyl ester | 390 | 1.62 |
| F-08 | | 3,3-difluoro-pyrrolidine | 311 | 1.57 |

TABLE 5-continued

Examples F02-F10

| No. | MOLSTRUCTURE | Amine | [M + H]⁺ | $t_R$ [min] |
|---|---|---|---|---|
| F-09 | 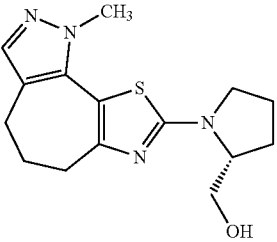 Chiral | (R)-1-pyrrolidin-2-yl-methanol | 305 | 1.32 |
| F-10 | 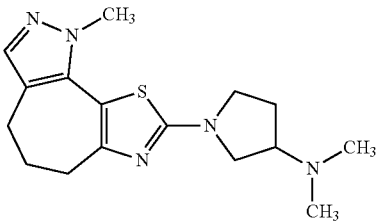 | dimethyl-pyrrolidin-3-yl-amine | 318 | 1,37 |

Example G

Examples G-01 to G-03 can be synthesized from example F-01 according to the following general procedure. The appropriate boronic acid required for synthesis can be deduced from the table of examples.

General Procedure G:

F-01 (1 eq), boronic acid (1.3 eq), tetrakis(triphenylphosphine)palladium (0.1 eq) and potassium carbonate (4 eq) are taken up in 1,2-dimethoxyethane and stirred overnight at 70° C. The reaction mixture is filtered and the filtrate is concentrated under reduced pressure. The product is purified by HPLC (C18, 5-98% acetonitrile in water containing 0.1% formic acid).

TABLE 6

G01-G03

| No. | MOLSTRUCTURE | Boronic acid | [M + H]⁺ | $t_R$ [min] |
|---|---|---|---|---|
| G-01 | 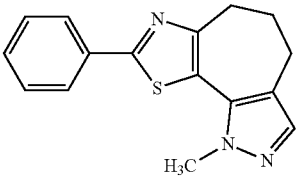 | phenyl-boronic acid | 282 | 1.93 |
| G-02 | 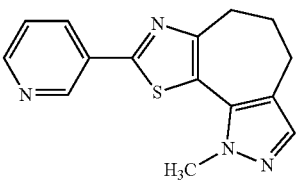 | pyridine-3-boronic acid | 283 | 1.50 |
| G-03 | 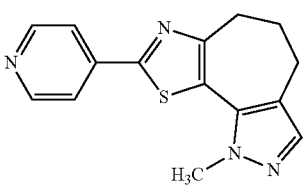 | pyridine-4-boronic acid | 283 | 1.56 |

Example H

Examples H-01 and H-02 can be synthesized from example F-01 according to the following general procedure. The appropriate amide required for synthesis can be deduced from the table of examples.

General Procedure H:

F-01 (2 eq), amide (1 eq), potassium carbonate (4 eq), CuI (0.1 eq) and 2-dimethylamino-ethylamine (0.2 eq) are taken up in toluene and stirred at 100° C. for 4 d. Water is added and the reaction mixture is extracted with ethyl acetate. The combined organic phases are washed with brine, dried over $MgSO_4$ and concentrated under reduced pressure. The product is purified by HPLC (C18, 5-98% acetonitrile in water containing 0.1% formic acid).

TABLE 7

H01-H02

| No. | MOLSTRUCTURE | Amide | $[M + H]^+$ | $t_R$ |
|---|---|---|---|---|
| H-01 | | 2-pyrrolidone | 289 | 1.43 |
| H-02 | | 2-piperidone | 303 | 1.61 |

Analytical Method 1
HPLC: Agilent 1100 Series
MS: Agilent LC/MSD SL
column: Waters, XBridge™ C18, 2.5 μm, 2.1×20 mm
solvent A=water+0.1% $NH_3$ (pH 9-10), B=acetonitrile HPLC grade
detection: MS positive and negative, mass range 120-800 m/z, fragmentor 70, gain EMV 1 threshold 150, stepsize 0.25 UV 315 nm, bandwidth 170 nm, reference off, range 210-400 nm, range step 2.00 nm, peakwidth 0.01 min, slit 2 nm
injection: 5 μL
flow: 1.00 mL/min
column temperature: 60° C.
gradient:

| 0.00 min | 5% B |
|---|---|
| 0.00-2.50 min | 5% -> 95% B |
| 2.50-2.80 min | 95% B |
| 2.81-3.10 min | 95% -> 5% B |

Analytical Method 2
HPLC: Agilent 1100/1200 Series
MS: Agilent LC/MSD SL
column: Waters, Sunfire, C18, 5 μm, 2.1×50 mm
solvent A=$H_2O$+0.1% formic acid, B=acetonitrile HPLC grade
detection: MS positive and negative, mass range 100-750 m/z, fragmentor 70, gain EMV 1, threshold 150, stepsize 0.30 UV 254/210 nm, bandwidth 8 nm, reference: off, range 190-400 nm, range step 4.00 nm, peakwidth<0.01 min, slit 4 nm
injection: 1-5 μL
flow: 1.00 mL/min
column temperature: 40° C.
gradient:

| 0.00-0.10 min | 5% B |
|---|---|
| 0.10-1.50 min | 5% → 95% B |
| 1.50-2.10 min | 95% B |
| 2.10-2.20 min | 95% → 5% B |

TABLE 8

Abbreviations used

| | | | |
|---|---|---|---|
| bu | butyl | tert | Tertiary |
| d | day(s) | THF | Tetrahydrofuran |
| DC | thin layer chromatography | LiHMDS | Lithium hexamethyl disilazide |
| DCM | dichloromethane | iPr | Isopropyl |
| DMF | N,N-dimethylformamide | MTBE | tertiary butylmethylether |
| DMSO | dimethylsulphoxide | NP | normal phase |
| et | ethyl | CDI | carbonyl diimidazole |
| h | hour(s) | ACN | Acetonitrile |
| HPLC | high performance liquid chromatography | BINAP | 2R,3S,2,2'-bis-(diphenyl-phosphino)-1,1'-binapthyl |
| M | molar | DIPEA | diisopropylethyl amine |
| me | methyl | | |
| min | minute(s) | DCE | 1,2-dichloroethane |
| mL | millilitre | NMP | N-methylpyrrolindinone |
| MS | mass spectrometry | prep | Preparative |
| N | normal | conc. | Concentrated |
| NMR | nuclear resonance spectroscopy | TFA | trifluoroacetic acid |
| ppm | part per million | HATU | N-[(dimethylamino)-(1H-1,2,3-triazolo[4,5-b]pyridin-1-yl)-methylene]-N-methylmethan-aminium hexafluorophosphate N-oxide |
| $R_f$ | retention factor | DMA | N,N-dimethylacetamide |
| RP | reversed phase | TBTU | O-(Benzotriazol-1-yl)-N,N,N',N'-tetramethyluronium tetrafluoroborate |

TABLE 8-continued

| Abbreviations used | | | |
|---|---|---|---|
| RT | room temperature | PEPPSI | [1,3-Bis(2,6-Diisopropylphenyl)-imidazol-2-ylidene](3-chloro-pyridyl)palladium(II) dichloride |
| $t_R$ | retention time | m.p. | melting point |
| DMAP | dimethyl-pyridin-4-yl-amine | DBU | 1,8-diazabicyclo[5.4.0]undec-7-ene |

The Examples that follow describe the biological activity of the compounds according to the invention without restricting the invention to these Examples.
Inhibition of mTOR-Induced p-4E-BP1 Phosphorylation (TR-FRET mTOR Activity Kit; Invitrogen)
Materials:
GFP-4E-BP1 substrate; Invitrogen order no. PV4759
Lanthascreen Tb-anti-p4E-BP1 (pThr46) Antibody Kit; Invitrogen order no. PV4758
FRAP1 (mTOR) kinase; Invitrogen order no. PV4753
ATP 10 mM
5× Assay Buffer (250 mM HEPES pH7.5, 0.05% Polysorbate 20, 5 mM EGTA, 50 mM MnCl2)
EDTA 500 mM
Determining IC50 Values for Test Compounds:
Kinase Reaction Conditions:
400 nM GFP-4E-BP1, 8 n1V1 ATP, ~150 ng/mL mTOR, 50 mM HEPES
pH 7.5, 0.01% Polysorbate 20, 1 mM EGTA, 10 mM MnCl2, and variable amounts of test compounds.
Preparation of Reagents:
Note: Thaw and keep mTOR, the substrate, ATP, and the antibody on ice prior to making working dilutions. Working dilutions of these components can be kept at room temperature for short periods of time the day of use.
1. Add 2 ml of 5× Assay Buffer to 8 ml water to prepare 10 ml of 1× Assay Buffer.
Note: The concentration of 1× Assay Buffer is 50 mM HEPES pH 7.5, 0.01% Polysorbate 20, 1 mM EGTA, and 10 mM MnCl2.
2. Prepare Antibody/EDTA Solution by first adding 2.75 nl of Tb-anti p4E-BP1 Antibody to 2397 nl of LanthaScreen™ TR-FRET Dilution Buffer. Then, add 100 nl of 0.5 M EDTA.
3. Prepare 4× Substrate/Enzyme Solution by first adding 72 nl of GFP-4E-BP1 (22 nM) to 926 nl of 1× Assay Buffer. Then, add 1.6 nl of mTOR (0.45 mg/mL).
4. Prepare ATP Solution by adding 3.2 nl of 10 mM ATP to 1997 nl of 1× Assay Buffer.
Serial Dilution of Inhibitors (16 Point Curve):
Note: It is recommended that inhibitors be serially diluted in DMSO, then diluted to a 4× working concentration with 1× Assay Buffer. The below procedure describes dilution of compounds in a 96-well format prior to transfer to a 384-well format for kinase assays. This procedure calls for dilution of the compounds in 2 adjacent columns of a 96-well plate, which upon transfer to a single column of a 384-well plate with an 8-channel pipette will align the samples in order of concentration.
1. Dispense 40 nl of DMSO to two adjacent columns of a 96 well plate per compound (e.g. columns 1 and 2).
2. Add 10 nl of inhibitor stock (10 mM) to the first well of the first column (A1) and mix.
3. Remove 10 nl from A1 and transfer to the adjacent well in the next column (B1) and mix.
4. Remove 10 nl from B1 and transfer to the next well in the first column (B2) and mix.
5. Repeat this dilution pattern through well H1 and leave the last well (H2) as DMSO only.
6. Remove 4 nl of diluted compounds and add to 96 nl of 1× Assay Buffer in a 96-well plate making 4× compound dilutions.
Kinase Reaction:
1. Add 2.5 μl of 4× compound dilutions from the first column of the 96-well plate to every other well of column 1 of a 384-well plate with an 8-channel pipette. Repeat for columns 2 and 3.
2. Add 2.5 nl of 4× compound dilutions from the second column of the 96-well plate to the empty wells of column 1 of the 384-well plate with an 8-channel pipette. Repeat for columns 2 and 3.
Note: This procedure aligns the compound dilutions in order of concentration.
3. Add 2.5 nl of 4× Enzyme/Substrate Solution to all columns 1-6.
4. Preincubate for 30 min. at RT (shaker).
5. Add 5 nl of ATP Solution to all wells to start reactions.
6. Shake the assay plate on a plate shaker for 30 seconds.
7. Incubate the assay plate for one hour at room temperature (20-25° C.).
Stop Step and Fluorescence Detection:
1. Add 10 nl of Antibody/EDTA Solution to each well in columns 1-9.
2. Shake the assay plate on a plate shaker for 30 seconds.
3. Incubate the assay plate for one hour at room temperature (20-25° C.).
4. Measure the GFP (FRET) and terbium (reference) emission signals on a fluorescence plate reader (e.g. Perkin Elmer Envision).
Data Analysis:
1. Calculate the emission ratio for each sample by dividing the GFP (FRET) signal by the terbium (reference) signal.
2. Plot the concentration of each compound versus the emission ratio. Determine the concentration of compound required to reach 50% of the maximum signal (IC50). Determination of IC50 values can be obtained by curve fitting (sigmoidal dose response, variable slope) using Prism software from GraphPad).
Inhibition of Proliferation: CyQuant PC-3
Description:
The CyQuant NF assay is based on measurement of cellular DNA content via fluorescent dye binding. Because cellular DNA content is highly regulated, it is closely proportional to cell number. The extent of proliferation is determined by comparing cell counts for samples treated with drugs with untreated controls. The assay is not dependent on physiological activities that may exhibit cell number-independent variability.
In the assay, a DNA-binding dye in combination with a plasma membrane permeabilization reagent is used. The medium is aspirated, replaced with dye binding solution, cells are incubated for 30-60 min, then fluorescence is measured (excitation at 485 nm, emission detection at 530 nm). Data are expressed as fluorescence emission intensity units as a function of time of incubation.

Cells and Reagents:
- PC-3 cells Human prostate carcinoma cells (ATCC CRL-1435)
- CyQuant NF assay Invitrogen Cat. # C35006
- PBS (w/o Ca, Mg) Life Technologies, Gibco BRL (Cat. No. 4190-094)
- F-12K Medium Life Technologies, Gibco BRL (Cat. No. 21127-022)
- Fetal calf serum Life Technologies, Gibco BRL (Cat. No. 10270-106)

Equipment:
- 96-well plates, flat bottom (Falcon, Cat. No.: 353072)
- 96-well plates, U-shaped (Costar, Cat. No.: 3799)
- $CO_2$-Incubator
- Microplate Reader, Wallac Victor Procedure:
Day 0: Seed 3000 PC-3 cells (cultured in F-12K/10% FCS) in 150 µl medium into a 96-well plate, flat bottom (include mediumblank). Incubate plates at 37° C. in a $CO_2$ incubator overnight.

Day 1: Dilute compounds to a concentration 80 µM->1:5 in medium, 7 dilution steps, in 96-well plates.
Add 50 µl per well of each dilution (total volume per well 200 µl; final conc. of cpds: 20 µM->1:5). If required, test further dilutions. All concentrations are tested in duplicates or triplicates.

Controls: Cells w/o cpd. (+50 µl medium+DMSO).
Cells are incubated with compounds for 3 days.

Day 4: Aspirate off medium and replace with 100 µl of 1× dye binding solution (22 µl CyQuant NF dye reagent added to 11 ml of 1×HBSS buffer). Cover the microplate and incubate for 30-60 min for equilibration of dye-DNA binding. Measure the fluorescence intensity in a microplate reader (excitation at 485 nm, emission detection at 530 nm).

Evaluation:
Calculate IC50 using GraphPad Prism (Fifty)

TABLE 9

Biological data

| Example No. | IC50 mTOR-FRET | EC50 CyQuant PC-3 |
|---|---|---|
| B-01 | 151 | 308 |
| B-03 | 87 | 263 |
| B-05 | 24 | 95 |
| B-06 | 36 | 66 |
| B-07 | 55 | 128 |
| B-09 | 266 | 334 |
| B-100 | 286 | |
| B-101 | 22 | 96 |
| B-102 | 32 | |
| B-103 | 37 | 87 |
| B-104 | 72 | |
| B-105 | 1385 | |
| B-106 | 69 | 178 |
| B-107 | 427 | |
| B-108 | 102 | 106 |
| B-109 | 49 | 162 |
| B-11 | 805 | 476 |
| B-110 | 840 | |
| B-111 | 4 | 38 |
| B-112 | 39 | 110 |
| B-113 | 9 | 29 |
| B-114 | 4 | 382 |
| B-115 | 2 | 16 |
| B-116 | 29 | 148 |
| B-117 | 35 | 306 |
| B-118 | 17 | 55 |

TABLE 9-continued

Biological data

| Example No. | IC50 mTOR-FRET | EC50 CyQuant PC-3 |
|---|---|---|
| B-119 | 1883 | |
| B-12 | 31 | 127 |
| B-120 | 65 | 250 |
| B-121 | 35 | 73 |
| B-122 | 32 | 79 |
| B-123 | 1137 | |
| B-124 | 994 | |
| B-125 | 114 | 253 |
| B-126 | 84 | |
| B-127 | 83 | 137 |
| B-128 | 108 | 119 |
| B-129 | 93 | 265 |
| B-130 | 19 | 178 |
| B-131 | 17 | 57 |
| B-132 | 52 | 326 |
| B-133 | 65 | 152 |
| B-134 | 60 | 143 |
| B-135 | 44 | 79 |
| B-137 | 422 | 1239 |
| B-138 | 38 | 236 |
| B-139 | 21 | 71 |
| B-140 | 182 | |
| B-141 | 512 | |
| B-142 | 92 | |
| B-143 | 71 | 424 |
| B-144 | 113 | |
| B-148 | 15 | 104 |
| B-17 | 53 | 114 |
| B-25 | 899 | 437 |
| B-27 | 501 | 328 |
| B-28 | 50 | 70 |
| B-29 | 200 | 276 |
| B-33 | 116 | 310 |
| B-35 | 219 | 408 |
| B-43 | 141 | 191 |
| B-45 | 782 | 375 |
| B-46 | 1204 | 447 |
| B-47 | 734 | 703 |
| B-48 | 451 | 710 |
| B-49 | 41 | 156 |
| B-50 | 30 | 209 |
| B-51 | 187 | 523 |
| B-52 | 146 | 326 |
| B-54 | 570 | 390 |
| B-55 | 170 | 450 |
| B-56 | 379 | 579 |
| B-57 | 70 | 147 |
| B-60 | 109 | 170 |
| B-61 | 15 | 69 |
| B-62 | 10 | 47 |
| B-63 | 27 | 143 |
| B-64 | 9 | 82 |
| B-65 | 13 | 75 |
| B-66 | 12 | 90 |
| B-68 | 166 | 604 |
| B-69 | 145 | 229 |
| B-70 | 62 | 284 |
| B-71 | 138 | 318 |
| B-72 | 84 | 298 |
| B-74 | 168 | |
| B-75 | 49 | 113 |
| B-76 | 31 | 79 |
| B-77 | 34 | 126 |
| B-78 | 136 | 249 |
| B-79 | 65 | 62 |
| B-81 | 41 | 23 |
| B-82 | 33 | 49 |
| B-83 | 65 | 41 |
| B-84 | 50 | |
| B-85 | 24 | 76 |
| B-86 | 32 | 47 |
| B-87 | 55 | 21 |
| B-88 | 269 | |
| B-89 | 57 | 72 |
| B-90 | 118 | 422 |
| B-92 | 152 | 221 |

TABLE 9-continued

Biological data

| Example No. | IC50 mTOR-FRET | EC50 CyQuant PC-3 |
|---|---|---|
| B-93 | 1111 | |
| B-94 | 8361 | |
| B-95 | 74 | |
| B-96 | 67 | 289 |
| B-97 | 175 | |
| B-98 | 737 | |
| B-99 | 53 | 168 |
| C-03 | 3336 | |
| C-07 | 2189 | |
| C-08 | 2441 | |
| C-09 | 960 | |
| D-04 | 402 | |
| D-05 | 358 | |
| D-06 | 1599 | |
| D-07 | 1277 | |
| E-01 | 5181 | |
| E-02 | 16000 | |
| E-03 | 4849 | |
| E-04 | 4891 | |
| E-05 | 20000 | |
| E-06 | 18000 | |
| E-07 | 11410 | |
| E-08 | 20000 | |
| E-09 | 8451 | |
| E-10 | 1580 | |
| E-11 | 6264 | |
| E-12 | 5413 | |
| E-13 | 524 | |
| E-14 | 698 | |
| E-15 | 47 | 138 |
| E-16 | 13 | 32 |
| E-17 | 65 | 171 |
| E-18 | 59 | 87 |
| G-02 | 20000 | |

The substances of the present invention are PI3 kinase pathway inhibitors, in particular of the serine/threonine kinase mTOR and/or members of the lipid kinase family Pi3K. On account of their biological properties, the novel compounds of the general formula (1) and their isomers and their physiologically tolerated salts are suitable for treating diseases which are characterized by excessive or anomalous cell proliferation. These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancers may be treated with compounds according to the invention, without being restricted thereto: brain tumours such as for example acoustic neurinoma, astrocytomas such as fibrillary, protoplasmic, gemistocytary, anaplastic, pilocytic astrocytomas, glioblastoma, gliosarcoma, pleomorphic xanthoastrocytoma, subependymal large-cell giant cell astrocytoma and desmoplastic infantile astrocytoma; brain lymphomas, brain metastases, hypophyseal tumour such as prolactinoma, hypophyseal incidentaloma, HGH (human growth hormone) producing adenoma and corticotrophic adenoma, craniopharyngiomas, medulloblastoma, meningeoma and oligodendroglioma; nerve tumours such as for example tumours of the vegetative nervous system such as neuroblastoma, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus and duodenum; eyelid tumours (basalioma or adenocarcinoma of the eyelid apparatus); retinoblastoma; carcinoma of the pancreas; carcinoma of the bladder; lung tumours (bronchial carcinoma-small-cell lung cancer (SCLC), non-small-cell lung cancer (NSCLC) such as for example spindle-cell plate epithelial carcinomas, adenocarcinomas (acinary, paillary, bronchiolo-alveolar) and large-cell bronchial carcinoma (giant cell carcinoma, clear-cell carcinoma)); breast cancer such as ductal, lobular, mucinous or tubular carcinoma, Paget's carcinoma; non-Hodgkin's lymphomas (B-lymphatic or T-lymphatic NHL) such as for example hair cell leukaemia, Burkitt's lymphoma or mucosis fungoides; Hodgkin's disease; uterine cancer (corpus carcinoma or endometrial carcinoma); CUP syndrome (Cancer of Unknown Primary); ovarian cancer (ovarian carcinoma-mucinous or serous cystoma, endometriodal tumours, clear cell tumour, Brenner's tumour); gall bladder cancer; bile duct cancer such as for example Klatskin tumour; testicular cancer (germinal or non-germinal germ cell tumours); laryngeal cancer such as for example supra-glottal, glottal and subglottal tumours of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocyoma, osteoclastoma or giant cell tumour, Ewing's sarcoma, and plasmocytoma, head and neck tumours (HNO tumours) such as for example tumours of the lips, and oral cavity (carcinoma of the lips, tongue, oral cavity), nasopharyngeal carcinoma (tumours of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumours of the paranasal sinuses and nasal cavity, tumours of the salivary glands and ears; liver cell carcinoma (hepatocellular carcinoma (HCC); leukaemias, such as for example acute leukaemias such as acute lymphatic/lymphoblastic leukaemia (ALL), acute myeloid leukaemia (AML); chronic lymphatic leukaemia (CLL), chronic myeloid leukaemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumour); oesophageal cancer; penile cancer; prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), to inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib, Erbitux® and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, meclorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or to polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities. In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or polyfunctional alcohols (e.g. EtOH or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinylpyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the above-mentioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
|---|---|
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
|---|---|
| Active compound in accordance with formula (1) | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, microcrystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
|---|---|
| Active compound in accordance with formula (1) | 50 mg |
| Sodium chloride | 50 mg |
| Water for injection | 5 mL |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

B-01 N-[3-(6-Ethylamino-pyridin-3-yl)-1-isopropyl-1,4,5,6-tetrahydro-9-thia-1,2,7-triaza-cyclopenta[e]azulen-8-yl]-acetamide B-02 N-[1-Ethyl-3-(6-methylamino-pyridin-3-yl)-1,4,5,6-tetrahydro-9-thia-1,2,7-triaza-cyclopenta[e]azulen-8-yl]-acetamide B-03 N-[1-(2-Methoxy-ethyl)-3-(6-methylamino-pyridin-3-yl)-1,4,5,6-tetrahydro-9-thia-1,2,7-triaza-cyclopenta[e]azulen-8-yl]-acetamide B-05 N-[1-Isopropyl-3-(6-methylamino-pyridin-3-yl)-1,4,5,6-tetrahydro-9-thia-1,2,7-triaza-cyclopenta[e]azulen-8-yl]-acetamide B-06 N-[3-(6-Methylamino-pyridin-3-yl)-1-o-tolyl-1,4,5,6-tetrahydro-9-thia-1,2,7-triaza-cyclopenta[e]azulen-8-yl]-acetamide B-07 N-[3-(6-Ethylamino-pyridin-3-yl)-1-o-tolyl-1,4,5,6-tetrahydro-9-thia-1,2,7-triaza-cyclopenta[e]azulen-8-yl]-acetamide B-09 N-[1-Isopropyl-3-(6-methyl-pyridin-3-yl)-1,4,5,6-tetrahydro-9-thia-1,2,7-triaza-cyclopent[e]azulen-8-yl]acetamide B-100 N-[3-(6-Ethylamino-pyridin-3-yl)-1-o-tolyl-1,4,5,6-tetrahydro-9-thia-1,2,7-triaza-cyclopenta[e]azulen-8-yl]-2-methoxy-acetamide B-103 N-[3-(6-Amino-pyridin-3-yl)-1-o-tolyl-1,4,5,6-tetrahydro-9-thia-1,2,7-triaza-cyclopenta[e]azulen-8-yl]-3-methoxy-propionamide B-104 N-[3-(6-Amino-pyridin-3-yl)-1-o-tolyl-1,4,5,6-tetrahydro-9-thia-1,2,7-triaza-cyclopenta[e]azulen-8-yl]-2-methoxy-acetamide B-106 3-Methoxy-N-[3-(6-methylamino-pyridin-3-yl)-1-o-tolyl-1,4,5,6-tetrahydro-9-thia-1,2,7-triaza-cyclopenta[e]azulen-8-yl]-propionamide B-107 2-Methoxy-N-[3-(6-methylamino-pyridin-3-yl)-1-o-tolyl-1,4,5,6-tetrahydro-9-thia-1,2,7-triaza-cyclopenta[e]azulen-8-yl]-acetamide B-11 N-[3-(6-Methyl-pyridin-3-yl)-1-o-tolyl-1,4,5,6-tetrahydro-9-thia-1,2,7-triaza-cyclopent[e]azulen-8-yl]-acetamide B-111 N-[1-(2-Fluoro-phenyl)-3-(1H-imidazol-4-yl)-1,4,5,6-tetrahydro-9-thia-1,2,7-triaza-cyclopenta[e]azulen-8-yl]-acetamide B-112 N-[3-(1H-imidazol-4-yl)-1-o-tolyl-1,4,5,6-tetrahydro-9-thia-1,2,7-triaza-cyclopenta[e]azulen-8-yl]-acetamide B-118 N-[1-(2-Ethyl-phenyl)-3-(1H-imidazol-4-yl)-1,4,5,6-tetrahydro-9-thia-1,2,7-triaza-cyclopenta[e]azulen-8-yl]-acetamide B-12 N-[1-(1-Cyclopropyl-piperidin-4-yl)-3-(6-methyl-pyridin-3-yl)-1,4,5,6-tetrahydro-9-thia-1,2,7-triaza-cyclopent[e]azulen-8-yl]acetamide B-120 N-[3-(2-Methyl-1H-imidazol-4-yl)-1-o-tolyl-1,4,5,6-tetrahydro-9-thia-1,2,7-triaza-cyclopenta[e]azulen-8-yl]-acetamide B-121 N-[1-Isobutyl-3-(2-methyl-1H-imidazol-4-yl)-1,4,5,6-tetrahydro-9-thia-1,2,7-triaza-cyclopenta[e]azulen-8-yl]-acetamide B-122 N-[3-(6-Ethylamino-pyridin-3-yl)-1-phenyl-1,4,5,6-tetrahydro-9-thia-1,2,7-triaza-cyclopenta[e]azulen-8-yl]-acetamide B-130 N-[3-(6-Amino-pyridin-3-yl)-1-ethyl-1,4,5,6-tetrahydro-9-thia-1,2,7-triaza-cyclopenta[e]azulen-8-yl]-acetamide B-131 N-[3-(6-Amino-pyridin-3-yl)-1-propyl-1,4,5,6-tetrahydro-9-thia-1,2,7-triaza-cyclopenta[e]azulen-8-yl]-acetamide B-132 N-[3-(6-Amino-pyridin-3-yl)-1-(2-methoxy-ethyl)-1,4,5,6-tetrahydro-9-thia-1,2,7-triaza-cyclopenta[e]azulen-8-yl]-acetamide B-133 N-[3-(6-Amino-pyridin-3-yl)-1-isopropyl-1,4,5,6-tetrahydro-9-thia-1,2,7-triaza-cyclopenta[e]azulen-8-yl]-3-methoxy-propionamide B-135 N-[3-(6-Amino-pyridin-3-yl)-1-isopropyl-1,4,5,6-tetrahydro-9-thia-1,2,7-triaza-cyclopenta[e]azulen-8-yl]-4-dimethylamino-butyramide B-137 N-[1-(2-Methyl-pyridin-3-yl)-3-(6-methyl-pyridin-3-yl)-1,4,5,6-tetrahydro-9-thia-1,2,7-triaza-cyclopent[e]azulen-8-yl]acetamide B-138 N-[3-(6-Amino-pyridin-3-yl)-1-(2-methyl-pyridin-3-yl)-1,4,5,6-tetrahydro-9-thia-1,2,7-triaza-cyclopent[e]azulen-8-yl]acetamide B-139 N-[3-(6-Methylamino-pyridin-3-yl)-1-(2-methyl-pyridin-3-yl)-1,4,5,6-tetrahydro-9-thia-1,2,7-triaza-cyclopent[e]azulen-8-yl]acetamide B-142 1-Methyl-3-[3-(6-methylamino-pyridin-3-yl)-1-o-tolyl-1,4,5,6-tetrahydro-9-thia-1,2,7-triaza-cyclopent[e]azulen-8-yl]-urea B-143 1-Methyl-3-[3-(6-methylamino-pyridin-3-yl)-1-(2-methyl-pyridin-3-yl)-1,4,5,6-tetrahydro-9-thia-1,2,7-triaza-cyclopent[e]azulen-8-yl]-urea B-144 1-[1-Isopropyl-3-(6-methylamino-pyridin-3-yl)-1,4,5,6-tetrahydro-9-thia-1,2,7-triaza-cyclopent[e]azulen-8-yl]-3-methyl-urea B-17 N-[1-(2-Fluoro-phenyl)-3-(6-methylamino-pyridin-3-yl)-1,4,5,6-tetrahydro-9-thia-1,2,7-triaza-cyclopenta[e]azulen-8-yl]-acetamide B-28 N-[1-(2-Chloro-phenyl)-3-(6-methylamino-pyridin-3-yl)-1,4,5,6-tetrahydro-9-thia-1,2,7-triaza-cyclopenta[e]azulen-8-yl]-acetamide B-49 3-[3-(6-Amino-pyridin-3-yl)-1-(1-cyclopropyl-piperidin-4-yl)-1,4,5,6-tetrahydro-9-thia-1,2,7-triaza-cyclopenta[e]azulen-8-yl]-1,1-dimethyl-urea B-50 [3-(6-Methylamino-pyridin-3-yl)-1-o-tolyl-1,4,5,6-tetrahydro-9-thia-1,2,7-triaza-cyclopenta[e]azulen-8-yl]-carbamic acid methyl ester B-61 N-[3-(6-Amino-pyridin-3-yl)-1-o-tolyl-1,4,5,6-tetrahydro-9-thia-1,2,7-triaza-cyclopenta[e]azulen-8-yl]-acetamide B-62 N-[3-(6-Amino-pyridin-3-yl)-1-(2-fluoro-phenyl)-1,4,5,6-tetrahydro-9-thia-1,2,7-triaza-cyclopenta[e]azulen-8-yl]-acetamide B-63 N-[3-(6-Amino-pyridin-3-yl)-1-(2-bromo-phenyl)-1,4,5,6-tetrahydro-9-thia-1,2,7-triaza-cyclopenta[e]azulen-8-yl]-acetamide B-64 N-[3-(6-Amino-pyridin-3-yl)-1-(2-chloro-phenyl)-1,4,5,6-tetrahydro-9-thia-1,2,7-triaza-cyclopenta[e]azulen-8-yl]-acetamide B-65 N-[3-(6-Amino-pyridin-3-yl)-1-(tetrahydro-pyran-3-yl)-1,4,5,6-tetrahydro-9-thia-1,2,7-triaza-cyclopenta[e]azulen-8-yl]-acetamide B-66 N-[3-(6-Amino-pyridin-3-yl)-1-isopropyl-1,4,5,6-tetrahydro-9-thia-1,2,7-triaza-cyclopenta[e]azulen-8-yl]-acetamide B-76 N-[3-(6-Ethylamino-pyridin-3-yl)-1-(2-fluoro-phenyl)-1,4,5,6-tetrahydro-9-thia-1,2,7-triaza-cyclopenta[e]azulen-8-yl]-acetamide B-77 N-[3-(6-Ethylamino-pyridin-3-yl)-1-(3-methyl-pyridin-4-yl)-1,4,5,6-tetrahydro-9-thia-1,2,7-triaza-cyclopenta[e]azulen-8-yl]-acetamide B-81 N-[1-(2-Fluoro-phenyl)-3-(6-methylamino-pyridin-3-yl)-1,4,5,6-tetrahydro-9-thia-1,2,7-triaza-cyclopenta[e]azulen-8-yl]-acetamide B-82 N-[3-(6-Methylamino-pyridin-3-yl)-1-(2-morpholin-4-yl-ethyl)-1,4,5,6-tetrahydro-9-thia-1,2,7-triaza-cyclopenta[e]azulen-8-yl]-acetamide B-83 N-[3-(6-Methylamino-pyridin-3-yl)-1-(tetrahydro-pyran-3-yl)-1,4,5,6-tetrahydro-9-thia-1,2,7-triaza-cyclopenta[e]azulen-8-yl]-acetamide B-85 N-[3-(6-Methylamino-pyridin-3-yl)-1-(3-methyl-pyridin-4-yl)-1,4,5,6-tetrahydro-9-thia-1,2,7-triaza-cyclopenta[e]azulen-8-yl]-acetamide B-86 N-[1-isobutyl-3-(6-methylamino-pyridin-3-yl)-1,4,5,6-tetrahydro-9-thia-1,2,7-triaza-cyclopenta[e]azulen-8-yl]-acetamide B-87 N-[3-(6-Methylamino-pyridin-3-yl)-1-phenyl-1,4,5,6-tetrahydro-9-thia-1,2,7-triaza-cyclopenta[e]azulen-8-yl]-acetamide B-88 N-[1-(2-Ethyl-phenyl)-3-(6-methylamino-pyridin-3-yl)-1,4,5,6-tetrahydro-9-thia-1,2,7-triaza-cyclopenta[e]azulen-8-yl]-acetamide B-96 3-[3-(6-Amino-pyridin-3-yl)-1-phenyl-1,4,5,6-tetrahydro-9-thia-1,2,7-triaza-cyclopenta[e]azulen-8-yl]-1,1-dimethyl-urea B-99 2-Amino-N-[3-(6-ethylamino-pyridin-3-yl)-1-o-tolyl-1,4,5,6-tetrahydro-9-thia-1,2,7-triaza-cyclopenta[e]azulen-8-yl]-acetamide E-15 N-[3-(6-Amino-pyridin-3-yl)-1-(2-fluoro-phenyl)-1,4,5,6-tetrahydro-9-thia-1,2,7-triaza-cyclopenta[e]azulen-8-yl]-3-methoxy-propionamide E-16 N-[3-(6-Amino-pyridin-3-yl)-1-(2-fluoro-phenyl)-1,4,5,6-tetrahydro-9-thia-1,2,7-triaza-cyclopenta[e]azulen-8-yl]-4-dimethylamino-butyramide E-17 N-[3-(6-Amino-pyridin-3-yl)-1-(2-fluoro-phenyl)-1,4,5,6-tetrahydro-9-thia-1,2,7-triaza-cyclopenta[e]azulen-8-yl]-2-dimethylamino-acetamide E-18 N-[3-(6-Amino-pyridin-3-yl)-1-(2-fluoro-phenyl)-1,4,5,6-tetrahydro-9-thia-1,2,7-triaza-E-18 cyclopenta[e]azulen-8-yl]-2-methoxy-acetamide

The invention claimed is:
1. A compound of the formula (1),

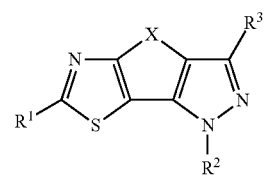

wherein

X is an unsubstituted C3 alkylidene chain; and $R^1$ denotes —NHR$^c$, —NHC(O)R$^c$, —NHC(O)OR$^c$, —NHC(O)NR$^c$R$^c$ or —NHC(O)N(R$^g$)OR$^c$; and $R^2$ denotes $C_{1-6}$alkyl, $C_{1-6}$alkenyl, $C_{1-6}$alkynyl, $C_{3-10}$cycloalkyl, $C_{6-10}$aryl, 5-12 membered heteroaryl or 3-14 membered heterocycloalkyl, optionally substituted by one or more R$^5$; and $R^3$ denotes a pyridin-3-yl group substituted by —NH$_2$, NH($C_{1-6}$)alkyl or halogen; and each R$^5$ independently of one another denotes a group selected from among R$^a$, R$^b$ and R$^a$ substituted by one or more identical or different R$^b$ and/or R$^c$; and each R$^a$ independently of one another denotes a group optionally substituted by one or more identical or different R$^b$ and/or R$^c$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each R$^b$ denotes a suitable group and is selected independently of one another from among =O, —OR$^c$, $C_{1-3}$haloalkyloxy, —OCF$_3$, =S, —SR$^c$, =NR$^c$, =NOR$^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^c$OR$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$, —N(R$^g$)C(NR$^g$)NR$^c$R$^c$, —N=R$^c$R$^c$ and —N=C(R$^g$)NR$^c$R$^c$ and each R$^c$ independently of one another denotes hydrogen or a group optionally substituted by one or more identical or different R$^d$ and/or R$^e$, selected from among C$_{1-6}$alkyl, C$_{1-6}$alkenyl, C$_{1-6}$alkynyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, and each R$^d$ denotes a suitable group and is selected independently of one another from among =O, —OR$^e$, C$_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$—N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^e$OR$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$, —N(R$^g$)C(NR$^g$)NR$^e$R$^e$, —N=R$^e$R$^e$ and —N=C(R$^g$)NR$^e$R$^e$ each R$^e$ independently of one another denotes hydrogen or a group optionally substituted by one or more identical or different R$^f$ and/or R$^g$, selected from among C$_{1-6}$alkyl, C$_{1-6}$alkenyl, C$_{1-6}$alkynyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, and each R$^f$ denotes a suitable group and in each case is selected independently of one another from among =O, —OR$^g$, C$_{1-3}$haloalkyloxy, —OCF$_3$, =S, —SR$^g$, =NR$^g$, =NOR$^g$, =NNR$^g$R$^g$, =NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, =N$_2$, —N$_3$, —S(O)R$^g$, —S(O)OR$^g$, —S(O)$_2$R$^g$, —S(O)$_2$OR$^g$, —S(O)NR$^g$R$^g$, —S(O)$_2$NR$^g$R$^g$, —OS(O)R$^g$, —OS(O)$_2$R$^g$, —OS(O)$_2$OR$^g$, —OS(O)NR$^g$R$^g$, —OS(O)$_2$NR$^g$R$^g$, —C(O)R$^g$, —C(O)OR$^g$, —C(O)SR$^g$, —C(O)NR$^g$R$^g$, —C(O)N(R$^h$)NR$^g$R$^g$, —C(O)N(R$^h$)OR$^g$, —C(NR$^h$)NR$^g$R$^g$, —C(NOH)R$^g$, —C(NOH)NR$^g$R$^g$, —OC(O)R$^g$, —OC(O)OR$^g$, —OC(O)SR$^g$, —OC(O)NR$^g$R$^g$, —OC(NR$^h$)NR$^g$R$^g$, —SC(O)R$^g$, —SC(O)OR$^g$, —SC(O)NR$^g$R$^g$, —SC(NR$^h$)NR$^g$R$^g$, —N(R$^h$)C(O)R$^g$, —N[C(O)R$^g$]$_2$, —N(OR$^h$)C(O)R$^g$, —N(R$^h$)C(NR$^h$)R$^g$, —N(R$^h$)N(R$^h$)C(O)R$^g$, —N[C(O)R$^g$]NR$^g$R$^g$, —N(R$^h$)C(S)R$^g$, —N(R$^h$)S(O)R$^g$, —N(R$^h$)S(O)OR$^g$, —N(R$^h$)S(O)$_2$R$^g$, —N[S(O)$_2$R$^g$]$_2$, —N(R$^h$)S(O)$_2$OR$^g$, —N(R$^h$)S(O)$_2$NR$^g$R$^g$, —N(R$^h$)[S(O)$_2$]$_2$R$^g$, —N(R$^h$)C(O)OR$^g$, —N(R$^h$)C(O)SR$^g$, —N(R$^h$)C(O)NR$^g$R$^g$, —N(R$^h$)C(O)NR$^g$OR$^g$, —N(R$^h$)C(O)NR$^h$NR$^g$R$^g$, —N(R$^h$)N(R$^h$)C(O)NR$^g$R$^g$, —N(R$^h$)C(S)NR$^g$R$^g$, —[N(R$^h$)C(O)]$_2$R$^g$, —N(R$^h$)[C(O)]$_2$R$^g$, —N{[C(O)]$_2$R$^g$}$_2$, —N(R$^h$)[C(O)]$_2$OR$^g$, —N(R$^h$)[C(O)]$_2$NR$^g$R$^g$, —N{[C(O)]$_2$OR$^g$}$_2$, —N{[C(O)]$_2$NR$^g$R$^g$}$_2$, —[N(R$^h$)C(O)]$_2$OR$^g$, —N(R$^h$)C(NR$^h$)OR$^g$, —N(R$^h$)C(NOH)R$^g$, —N(R$^h$)C(NR$^h$)SR$^g$, —N(R$^h$)C(NR$^h$)NR$^g$R$^g$, —N=R$^h$R$^h$ and —N=C(R$^h$)NR$^h$R$^h$; and each R$^g$ independently of one another denotes hydrogen or a group optionally substituted by one or more identical or different R$^h$, selected from among C$_{1-6}$alkyl, C$_{1-6}$alkenyl, C$_{1-6}$alkynyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero aryl, 6-18 membered heteroarylalkyl, 3-14 membered heterocycloalkyl and 4-14 membered heterocycloalkylalkyl; and each R$^h$ is selected independently of one another from among hydrogen, C$_{1-6}$alkyl, C$_{1-6}$alkenyl, C$_{1-6}$alkynyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$ arylalkyl, 5-12 membered heteroaryl, 6-18 membered heteroarylalkyl, 3-14 membered heterocycloalkyl and 4-14 membered heterocycloalkylalkyl, or a tautomer or salt thereof.

2. A compound according to claim 1, wherein R$^1$ is selected from the group consisting of hydrogen, —NH$_2$,

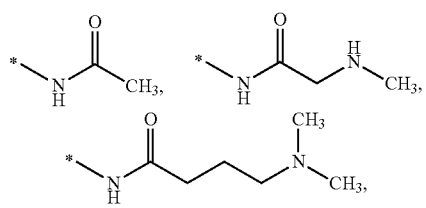

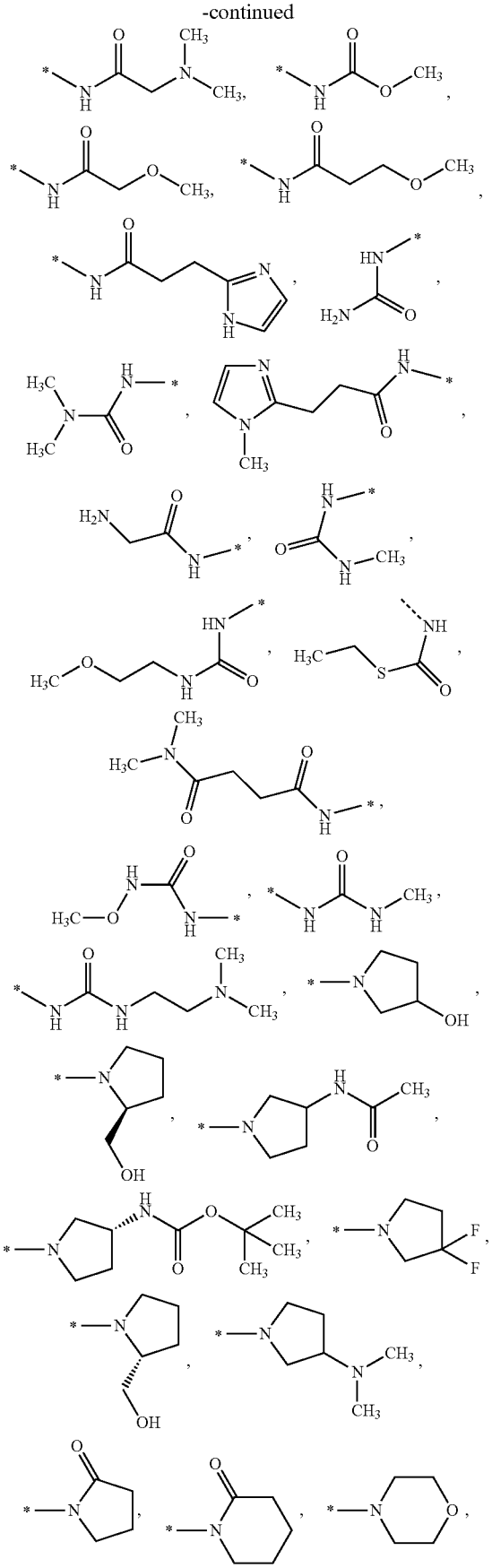
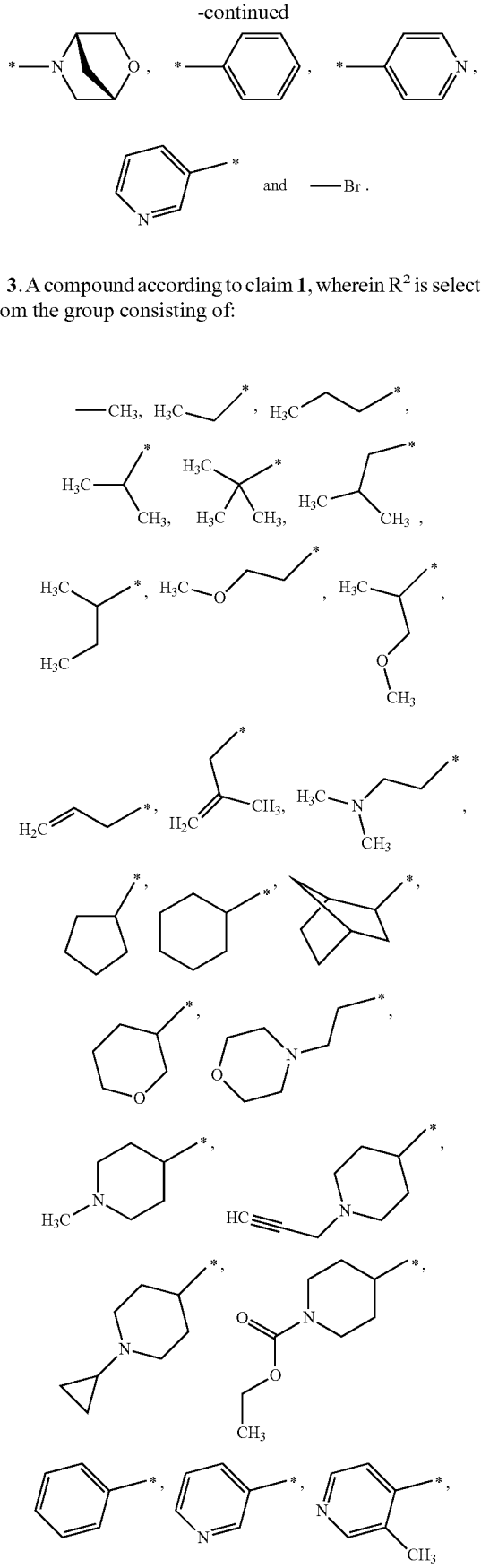
3. A compound according to claim 1, wherein $R^2$ is selected from the group consisting of:

-continued

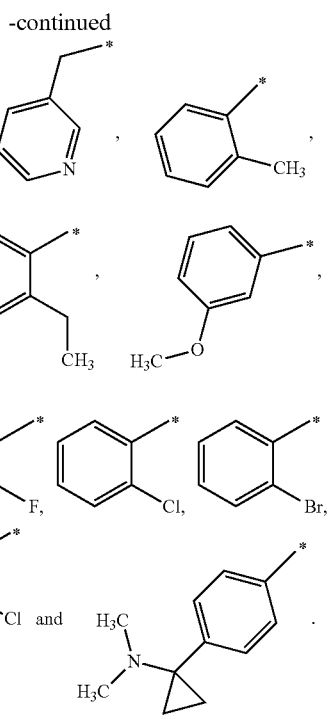

4. A compound according to claim 1, wherein R³ is selected from the

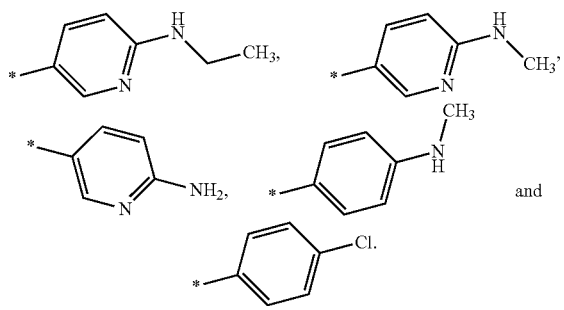

5. A compound selected from:
N-[3-(6-Ethylamino-pyridin-3-yl)-1-isopropyl-1,4,5,6-tetrahydro-9-thia-1,2,7-triaza-cyclopenta[e]azulen-8-yl]-acetamide
N-[1-Ethyl-3-(6-methylamino-pyridin-3-yl)-1,4,5,6-tetrahydro-9-thia-1,2,7-triaza-cyclopenta[e]azulen-8-yl]-acetamide
N-[1-(2-Methoxy-ethyl)-3-(6-methylamino-pyridin-3-yl)-1,4,5,6-tetrahydro-9-thia-1,2,7-triaza-cyclopenta[e]azulen-8-yl]-acetamide
N-[1-Isopropyl-3-(6-methylamino-pyridin-3-yl)-1,4,5,6-tetrahydro-9-thia-1,2,7-triaza-cyclopenta[e]azulen-8-yl]-acetamide
N-[3-(6-Methylamino-pyridin-3-yl)-1-o-tolyl-1,4,5,6-tetrahydro-9-thia-1,2,7-triaza-cyclopenta[e]azulen-8-yl]-acetamide
N-[3-(6-Ethylamino-pyridin-3-yl)-1-o-tolyl-1,4,5,6-tetrahydro-9-thia-1,2,7-triaza-cyclopenta[e]azulen-8-yl]-acetamide
N-[3-(6-Ethylamino-pyridin-3-yl)-1-o-tolyl-1,4,5,6-tetrahydro-9-thia-1,2,7-triaza-cyclopenta[e]azulen-8-yl]-2-methoxy-acetamide
N-[3-(6-Amino-pyridin-3-yl)-1-o-tolyl-1,4,5,6-tetrahydro-9-thia-1,2,7-triaza-cyclopenta[e]azulen-8-yl]-3-methoxy-propionamide
N-[3-(6-Amino-pyridin-3-yl)-1-o-tolyl-1,4,5,6-tetrahydro-9-thia-1,2,7-triaza-cyclopenta[e]azulen-8-yl]-2-methoxy-acetamide
3-Methoxy-N-[3-(6-methylamino-pyridin-3-yl)-1-o-tolyl-1,4,5,6-tetrahydro-9-thia-1,2,7-triaza-cyclopenta[e]azulen-8-yl]-propionamide
2-Methoxy-N-[3-(6-methylamino-pyridin-3-yl)-1-o-tolyl-1,4,5,6-tetrahydro-9-thia-1,2,7-triaza-cyclopenta[e]azulen-8-yl]-acetamide
N-[3-(6-Ethylamino-pyridin-3-yl)-1-phenyl-1,4,5,6-tetrahydro-9-thia-1,2,7-triaza-cyclopenta[e]azulen-8-yl]-acetamide
N-[3-(6-Amino-pyridin-3-yl)-1-ethyl-1,4,5,6-tetrahydro-9-thia-1,2,7-triaza-cyclopenta[e]azulen-8-yl]-acetamide
N-[3-(6-Amino-pyridin-3-yl)-1-propyl-1,4,5,6-tetrahydro-9-thia-1,2,7-triaza-cyclopenta[e]azulen-8-yl]-acetamide
N-[3-(6-Amino-pyridin-3-yl)-1-(2-methoxy-ethyl)-1,4,5,6-tetrahydro-9-thia-1,2,7-triaza-cyclopenta[e]azulen-8-yl]-acetamide
N-[3-(6-Amino-pyridin-3-yl)-1-isopropyl-1,4,5,6-tetrahydro-9-thia-1,2,7-triaza-cyclopenta[e]azulen-8-yl]-3-methoxy-propionamide
N-[3-(6-Amino-pyridin-3-yl)-1-isopropyl-1,4,5,6-tetrahydro-9-thia-1,2,7-triaza-cyclopenta[e]azulen-8-yl]-4-dimethylamino-butyramide
N-[3-(6-Amino-pyridin-3-yl)-1-(2-methyl-pyridin-3-yl)-1,4,5,6-tetrahydro-9-thia-1,2,7-triaza-cyclopent[e]azulen-8-yl]-acetamide
N-[3-(6-Methylamino-pyridin-3-yl)-1-(2-methyl-pyridin-3-yl)-1,4,5,6-tetrahydro-9-thia-1,2,7-triaza-cyclopent[e]azulen-8-yl]-acetamide
1-Methyl-3-[3-(6-methylamino-pyridin-3-yl)-1-o-tolyl-1,4,5,6-tetrahydro-9-thia-1,2,7-triaza-cyclopent[e]azulen-8-yl]-urea
1-Methyl-3-[3-(6-methylamino-pyridin-3-yl)-1-(2-methyl-pyridin-3-yl)-1,4,5,6-tetrahydro-9-thia-1,2,7-triaza-cyclopent[e]azulen-8-yl]-urea
1-[1-Isopropyl-3-(6-methylamino-pyridin-3-yl)-1,4,5,6-tetrahydro-9-thia-1,2,7-triaza-cyclopent[e]azulen-8-yl]-3-methyl-urea
N-[1-(2-Chloro-phenyl)-3-(6-methylamino-pyridin-3-yl)-1,4,5,6-tetrahydro-9-thia-1,2,7-triaza-cyclopenta[e]azulen-8-yl]-acetamide
3-[3-(6-Amino-pyridin-3-yl)-1-(1-cyclopropyl-piperidin-4-yl)-1,4,5,6-tetrahydro-9-thia-1,2,7-triaza-cyclopenta[e]azulen-8-yl]-1,1-dimethyl-urea
[3-(6-Methylamino-pyridin-3-yl)-1-o-tolyl-1,4,5,6-tetrahydro-9-thia-1,2,7-triaza-cyclopenta[e]azulen-8-yl]-carbamic acid methyl ester
N-[3-(6-Amino-pyridin-3-yl)-1-o-tolyl-1,4,5,6-tetrahydro-9-thia-1,2,7-triaza-cyclopenta[e]azulen-8-yl]-acetamide
N-[3-(6-Amino-pyridin-3-yl)-1-(2-fluoro-phenyl)-1,4,5,6-tetrahydro-9-thia-1,2,7-triaza-cyclopenta[e]azulen-8-yl]-acetamide
N-[3-(6-Amino-pyridin-3-yl)-1-(2-bromo-phenyl)-1,4,5,6-tetrahydro-9-thia-1,2,7-triaza-cyclopenta[e]azulen-8-yl]-acetamide N-[3-(6-Amino-pyridin-3-yl)-1-(2-chloro-phenyl)-1,4,5,6-tetrahydro-9-thia-1,2,7-triaza-cyclopenta[e]azulen-8-yl]-acetamide N-[3-(6-Amino-pyridin-3-yl)-1-(tetrahydro-pyran-3-yl)-1,4,5,6-tetrahydro-9-thia-1,2,7-triaza-cyclopenta[e]azulen-8-yl]-acetamide N-[3-(6-Amino-pyridin-3-yl)-1-isopropyl-1,4,5,6-tetrahydro-9-thia-1,2,7-triaza-cyclopenta[e]azulen-8-yl]-acetamide N-[3-(6-Ethylamino-pyridin-3-yl)-1-(2-fluoro-phenyl)-1,4,5,6-tetrahydro-9-thia-1,2,7-triaza-cyclopenta[e]azulen-8-yl]-acetamide N-[3-(6-Ethylamino-pyridin-3-yl)-1-(3-methyl-pyridin-4-yl)-1,4,5,6-tetrahydro-9-thia-1,2,7-triaza-cyclopenta[e]azulen-8-yl]-acetamide N-[1-(2-Fluoro-phenyl)-3-(6-methylamino-pyridin-3-yl)-1,4,5,6-tetrahydro-9-thia-1,2,7-triaza-cyclopenta[e]azulen-8-yl]-acetamide N-[3-(6-Methylamino-pyridin-3-yl)-1-(2-morpholin-4-yl-ethyl)-1,4,5,6-tetrahydro-9-thia-1,2,7-triaza-cyclopenta[e]azulen-8-yl]-acetamide N-[3-(6-Methylamino-pyridin-3-yl)-1-(tetrahydro-pyran-3-yl)-1,4,5,6-tetrahydro-9-thia-1,2,7-triaza-cyclopenta[e]azulen-8-yl]-acetamide N-[3-(6-Methylamino-pyridin-3-yl)-1-(3-methyl-pyridin-4-yl)-1,4,5,6-tetrahydro-9-thia-1,2,7-triaza-cyclopenta[e]azulen-8-yl]-acetamide N-[1-Isobutyl-3-(6-methylamino-pyridin-3-yl)-1,4,5,6-tetrahydro-9-thia-1,2,7-triaza-cyclopenta[e]azulen-8-yl]-acetamide N-[3-(6-Methylamino-pyridin-3-yl)-1-phenyl-1,4,5,6-tetrahydro-9-thia-1,2,7-triaza-cyclopenta[e]azulen-8-yl]-acetamide N-[1-(2-Ethyl-phenyl)-3-(6-methylamino-pyridin-3-yl)-1,4,5,6-tetrahydro-9-thia-1,2,7-triaza-cyclopenta[e]azulen-8-yl]-acetamide 3-[3-(6-Amino-pyridin-3-yl)-1-phenyl-1,4,5,6-tetrahydro-9-thia-1,2,7-triaza-cyclopenta[e]azulen-8-yl]-1,1-dimethyl-urea 2-Amino-N-[3-(6-ethylamino-pyridin-3-yl)-1-o-tolyl-1,4,5,6-tetrahydro-9-thia-1,2,7-triaza-cyclopenta[e]azulen-8-yl]-acetamide N-[3-(6-Amino-pyridin-3-yl)-1-(2-fluoro-phenyl)-1,4,5,6-tetrahydro-9-thia-1,2,7-triaza-cyclopenta[e]azulen-8-yl]-3-methoxy-propionamide N-[3-(6-Amino-pyridin-3-yl)-1-(2-fluoro-phenyl)-1,4,5,6-tetrahydro-9-thia-1,2,7-triaza-cyclopenta[e]azulen-8-yl]-4-dimethylamino-butyramide N-[3-(6-Amino-pyridin-3-yl)-1-(2-fluoro-phenyl)-1,4,5,6-tetrahydro-9-thia-1,2,7-triaza-cyclopenta[e]azulen-8-yl]-2-dimethylamino-acetamide N-[3-(6-Amino-pyridin-3-yl)-1-(2-fluoro-phenyl)-1,4,5,6-tetrahydro-9-thia-1,2,7-triaza-cyclopenta[e]azulen-8-yl]-2-methoxy-acetamide.

6. A pharmaceutically acceptable salt of a compound according to anyone of claim 1 or 2 to 5.

7. A pharmaceutical composition comprising a compound according to anyone of claim 1 or 2 to 5, or a pharmaceutically acceptable salt thereof, and a carrier or diluent.

8. Pharmaceutical preparations, containing as active substance one or more compounds of general formula (1) according to anyone of claim 1 or 2 to 5 or the pharmacologically effective salts thereof, optionally in combination with conventional excipients and/or carriers.

* * * * *